United States Patent
Jennings

(10) Patent No.: US 12,329,766 B2
(45) Date of Patent: *Jun. 17, 2025

(54) COMPOUNDS, METHODS, AND TREATMENTS FOR ABNORMAL SIGNALING PATHWAYS FOR PRENATAL AND POSTNATAL DEVELOPMENT

(71) Applicant: Barbara Brooke Jennings, Juno Beach, FL (US)

(72) Inventor: Barbara Brooke Jennings, Juno Beach, FL (US)

( * ) Notice: Subject to any disclaimer, the term of this patent is extended or adjusted under 35 U.S.C. 154(b) by 127 days.

This patent is subject to a terminal disclaimer.

(21) Appl. No.: 17/445,449

(22) Filed: Aug. 19, 2021

(65) Prior Publication Data

US 2022/0110954 A1    Apr. 14, 2022

Related U.S. Application Data

(63) Continuation of application No. 14/979,202, filed on Dec. 22, 2015, now Pat. No. 11,096,950, which is a continuation of application No. 14/487,284, filed on Sep. 16, 2014, now abandoned, which is a continuation of application No. 13/102,696, filed on May 6, 2011, now abandoned, which is a continuation-in-part of application No. 12/387,239, filed on Apr. 30, 2009, now abandoned, which is a continuation-in-part of application No. 12/001,869, filed on Dec. 13, 2007, now abandoned, which is a continuation-in-part of application No. 11/591,398, filed on Nov. 1, 2006, now abandoned.

(51) Int. Cl.
| | | |
|---|---|---|
| A61K 31/6615 | (2006.01) | |
| A61K 31/265 | (2006.01) | |
| A61K 31/357 | (2006.01) | |
| C07C 69/96 | (2006.01) | |
| C07D 317/34 | (2006.01) | |
| C07F 9/06 | (2006.01) | |

(52) U.S. Cl.
CPC ........ *A61K 31/6615* (2013.01); *A61K 31/265* (2013.01); *A61K 31/357* (2013.01); *C07C 69/96* (2013.01); *C07D 317/34* (2013.01); *C07F 9/06* (2013.01); *C07F 9/062* (2013.01)

(58) Field of Classification Search
CPC .......................... A61K 31/6615; A61P 35/00
See application file for complete search history.

(56) References Cited

PUBLICATIONS

Gura et al. (Science 1997).*
Johnson et al., (British J. of Cancer 2001).*
Cecil Textbook of Medicine, 20th Edition, vol. 1, 1996.*

* cited by examiner

*Primary Examiner* — Shobha Kantamneni
(74) *Attorney, Agent, or Firm* — ArentFox Schiff LLP

(57) ABSTRACT

The present invention relates to prevention of congenital deformations. The invention further relates to cancer inhibition and prevention. The invention further relates to methods and compositions to modulate, antagonize, or agonize disparate signaling pathways that may converge to regulate patterning events and gene expression during prenatal development, postnatal development, and during development in the adult, organism. The invention also relates to activators or deactivators of pyruvate kinase M2 (PKM2) for the treatment, prevention, or amelioration of diseases related to PKM2 function.

9 Claims, No Drawings

COMPOUNDS, METHODS, AND TREATMENTS FOR ABNORMAL SIGNALING PATHWAYS FOR PRENATAL AND POSTNATAL DEVELOPMENT

CROSS-REFERENCE TO RELATED APPLICATIONS

This application is a Continuation of 14/979,202, filed Dec. 22, 2015, now U.S. Pat. No. 11,096,950, issued Aug. 24, 2021, which is a Continuation of 14/487,284, filed Sep. 16, 2014, now abandoned, which is a Continuation of 13/102,696, filed May 6, 2011, now abandoned, which is a Continuation-in-part of 12/387,239, filed Apr. 30, 2009, now abandoned, which is a Continuation-in-part of 12/001,869, filed Dec. 13, 2007, now abandoned, which is a Continuation-in-part of 11/591,398, filed Nov. 1, 2006, now abandoned, the disclosures of which are incorporated herein by reference in their entireties.

STATEMENT REGARDING FEDERALLY SPONSORED RESEARCH OR DEVELOPMENT

Not Applicable

FIELD OF THE INVENTION

The present invention relates to the field use of inositol stereoisomers and derivatives thereof, especially phosphorylated and carboxylated derivatives thereof (the invention compounds, some of which are novel compounds) in a wide range of disease states and medical conditions. The invention further relates to use of the invention compounds to modulate signaling pathways in the development and growth of various cells. Still further, the invention relates to reducing the incidence of fetal defects due to aberrant pattern formation during gestation. Still further, the invention relates to prevention of fetal alcohol syndrome with invention compounds and combinations. This invention also relates to novel inhibitors of alpha Tumor Necrosis Factor and protein kinases, pharmaceutical compounds containing inhibitors, and methods for preparing these inhibitors. They can be useful for the treatment of hepatitis A, B, C, D, the treatments of chronic inflammation, chronic inflammatory arthritis such as rheumatoid arthritis, other chronic active diseases, chrohn's disease, inflammatory bowel disease, cancer, autoimmune diseases like lupus, sjrogren's, mixed connective tissue disease, and other pro-inflammatory cytokine-mediated diseases.

The invention still further relates to combination therapy of one or more of the invention compounds with a substantial range of additional compounds, such as anti-cancer therapeutic agents; etc. as further detailed herein (generally as means of reducing tumor load or distant metastasis, or as a synergistic inhibitor) as well as agents which prevent or diminish the aberrant cell from obtaining drug resistance; estrogenic or antiandrogenic therapeutic substances (generally as a means of inhibiting the response of breast tissue to estrogen excess insult (absolute or relative estrogen excess as compared to normal estrogenic/androgenic substance balance); folic acid or other folate sources (primarily with respect to reducing the incidence of fetal malformations), etc. as further detailed herein.

Still further, the invention relates to reducing the emergence of resistance to interferon alpha therapy, to normalizing abnormal activity of TNF as well as kinases active in chronic-active hepatitis (Janus Kinase [JAK] and TYK2) activated upon INF-alpha binding, as well as conditions resulting from such abnormal kinase activity. The methods and compositions can also be used to treat abnormal kinase activity in cancers. These include, phosphatidylinositol 3-kinase (PI3K-AKT Mtor signaling pathway)Ras/MAPK-erk ½ pathway, Rapamycin pathway, Insulin like growth factor (S) signaling, protein kinases including serine/threonine kinases such as Raf kinases, such as aurora kinases, protein kinase such as MEK, and tyrosine kinases, epidermal growth factor receptor family (KGFR), platelet-derived growth factor receptor family (PDGFR), vascular endothelial growth factor receptor (VEGFR) family, nerve growth factor receptor family (NGFR), fibroblast growth factor receptor family (FGFR) insulin receptor family, ephrin receptor family, Met family, Ror family, c-kit family, Src family, Fes family, Fak family, Syk/ZAP-70 family, Tec family and Ab1 family. Furthermore, these compounds and methods can be used to upregulate the p27kip1 and P21cip1 and to down regulate or inhibit Ap-1 and ppRb.

More specifically, in some embodiments, the present invention further relates to the phosphatidylinositol/PI3K signaling pathways for prevention or correction of improper signaling in these pathways. In still other embodiments, the invention relates to compositions for the prevention and/or minimization of fetal malformations, some of which are due to sonic hedgehog (Shh) and/or other hedgehog variants such as Indian (Ihh) and Desert (Dhh), etc. signaling defects; for the prevention and/or inhibition of breast cancer and metastases thereof some of which are due to one or more of sequela of estrogen exposure or estrogen surplus exposure (whether during hormonal therapy (males or females) or birth control use) or super-active estrogen receptors, or due to excess number of estrogen receptors (receptor expansion), or excessively sensitive estrogen receptors in mammary epithelial breast tissue (whether due to derangements in signaling pathways or other bases such as estrogen receptor overexpression in certain predisposed phenotypes, whether due to developmental, or to environmental, or endogenous exposures). The invention further relates to increasing the therapeutic efficacy of anti-cancer agents, especially those related to the prevention or treatment of breast and prostate cancers, and the prevention or reduction of aberrant cells becoming resistant to one or more anti-cancer agents.

Still further, the invention relates to the Warburg effect on proliferating cells without limitation. The energy that stimulates cancer cells is derived from glycolysis which is the Warburg effect, the metabolic change, the primary alteration in cancer cells which confers survival advantage of cancer cells over normal proliferating cells in animals. One of the most frequently mutated genes in cancer is p53 which appears to modulate the balance between the utilization of respiration and glycolytic pathways. Cytochrome C oxidase (SCO2) appears to be the downstream mediator of this effect. This SCO2 protein enzyme is crucial for regulating the cytochrome c oxidase (cox complex) which is the major site of oxygen use in animals. By disrupting the SCO2 gene or upregulating tumor suppressor gene p53, without being bound to theory, the inventor believes that some of the compounds will turn off the metabolic switch towards glycolysis and deactivate phosphotyrosine binding or signaling cascades.

The invention also relates to activators or deactivators of pyruvate kinase M2 (PKM2) for the treatment, prevention, or amelioration of diseases related to PKM2 function. Pyruvate kinase (PK) is a metabolic enzyme that converts phosphoenolpyruvate to pyruvate during glycolysis. Four PK isoforms exist in mammals: the L and R isoforms are expressed in liver and red blood cells, respectively, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediates, whereas M1 is a constitutively active enzyme.

All tumor cells exclusively express the embryonic M2 isoform of pyruvate kinase. PKM2 can serve as a target in cancer therapy. PKM2 is also expressed in adipose tissue and activated T-cells and thus activators of PKM2 can be used to treat disorders that are dependent on such cells.

While not wishing to be bound by theory, it is believed that PKM2-dependent cells, e.g., cancer cells, must regulate PKM2, activating it when the cell's need for completion of glycolysis and maximal ATP production is relatively greater and inhibiting it when the cell's need for anabolic processes (growth) is relatively greater. Thus, the endogenous ability to modulate the activity of PKM2 is critically important to the cell. Therapeutic or exogenous modulation of PKM2 by inhibition or activation, e.g., constitutive activation or inhibition, defeats the endogenous modulation or regulation by the cell. Activators can be used to treat disorders related to PKM2 metabolism, e.g., disorders characterized by unwanted cell proliferation, e.g., cancer, obesity, diabetes, atherosclerosis, restenosis, and autoimmune conditions. Selective activators are preferred. Thus, activating PKM2 can mean depriving or compromising the ability of a cell to inactivate PKM2. An activator can reduce the cell's ability to down regulate PKM2 and can, for example, turn regulated PKM2 activity into constitutive PKM2 activity.

The invention further relates to signaling cascades such as Receptor tyrosine kinase/PI3K/AKT/mamammlian target of rapamycin (Mtor) on proliferating and tumor cells as an activator of PKM2 or in tumor metabolism and growth. Because of the fact that receptor tyrosine kinase/PI3K/AKT/mammalian target of rapamycin (RTK/PI3K/AKT/mTOR) signaling cascade is a frequently altered pathway in cancer as previously described in the parent application. The inventor believes that receptor tyrosine kinase/PI3K/AKT/mammalian target of rapamycin (RTK/PI3K/AKT/mTOR) may also play a pivotal role as an activator of the Warburg effect by inducing PKM2 and other glycolytic enzymes under normoxic conditions. By disrupting these pathways that may also have a critical role in cancer cell metabolism, PKM2 upregulation may be suppressed by inhibiting signaling pathways that are addicted to aerobic glycolysis. By dual suppression of signaling pathways, without being bound to theory, the inventor believes that hyperactive states of certain signaling pathways, contributes to the development of the Warburg effect in many cancers. For inhibiting PI3K/mTOR/HIF/MYC-hnRNPS/PKM2 and PKM2 glycolysis signaling network, we have found utility for the following classes of compounds, including, albeit not limited to any inositol, derivative, or analog. While the D-Chiro inositol analogs are exemplified here, it is understood that all species of inositols, their isomeric analogous phosphate derivatives, and/or their phosphatidyl inositol phosphate derivatives are included herein without limitation.

Tetraphosphates
1. D-chiro-inositol 1,2,3,4-tetraphosphate
2. D-chiro-inositol 1,2,3,5-tetraphosphate
3. D-chiro-inositol 1,2,3,6-tetraphosphate
4. D-chiro-inositol 1,2,4,5-tetraphosphate
5. D-chiro-inositol 1,2,4,6-tetraphosphate
6. D-chiro-inositol 1,2,5,6-tetraphosphate
7. D-chiro-inositol 1,3,4,5-tetraphosphate
8. D-chiro-inositol 1,3,4,6-tetraphosphate
9. D-chiro-inositol 1,3,5,6-tetraphosphate
10. D-chiro-inositol 1,4,5,6-tetraphosphate
11. D-chiro-inositol 2,3,4,5-tetraphosphate
12. D-chiro-inositol 2,3,4,6-tetraphosphate
13. D-chiro-inositol 2,3,5,6-tetraphosphate
14. D-chiro-inositol 2,4,5,6-tetraphosphate
15. D-chiro-inositol 3,4,5,6-tetraphosphate Pentaphosphates
1. D-chiro-inositol 1,2,3,4,5-pentaphosphate
2. D-chiro-inositol 1,2,3,4,6-pentaphosphate
3. D-chiro-inositol 1,2,3,5,6-pentaphosphate
4. D-chiro-inositol 1,2,4,5,6-pentaphosphate
5. D-chiro-inositol 1,3,4,5,6-pentaphosphate
6. D-chiro-inositol 2,3,4,5,6-pentaphosphate Hexaphosphates
1. D-chiro-inositol 1,2,3,4,5,6-hexaphosphate Heptaphosphates
1. D-chiro-inositol 1,2,3,4,5-pentaphosphate-6-pyrophosphate
2. D-chiro-inositol 1,2,3,4,6-pentaphosphate-5-pyrophosphate
3. D-chiro-inositol 1,2,3,5,6-pentaphosphate-4-pyrophosphate
4. D-chiro-inositol 1,2,4,5,6-pentaphosphate-3-pyrophosphate
5. D-chiro-inositol 1,3,4,5,6-pentaphosphate-2-pyrophosphate
6. D-chiro-inositol 2,3,4,5,6-pentaphosphate-1-pyrophosphate
7. D-chiro-inositol 1,2,3-triphosphate-4,5-dipyrophosphate
8. D-chiro-inositol 1,2,3-triphosphate-4,6-dipyrophosphate
9. D-chiro-inositol 1,2,3-triphosphate-5,6-dipyrophosphate
10. D-chiro-inositol 1,2,4-triphosphate-3,5-dipyrophosphate
11. D-chiro-inositol 1,2,4-triphosphate-3,6-dipyrophosphate
12. D-chiro-inositol 1,2,4-triphosphate-5,6-dipyrophosphate
13. D-chiro-inositol 1,2,5-triphosphate-3,4-dipyrophosphate
14. D-chiro-inositol 1,2,5-triphosphate-3,6-dipyrophosphate
15. D-chiro-inositol 1,2,5-triphosphate-4,6-dipyrophosphate
16. D-chiro-inositol 1,2,6-triphosphate-3,4-dipyrophosphate
17. D-chiro-inositol 1,2,6-triphosphate-3,5-dipyrophosphate
18. D-chiro-inositol 1,2,6-triphosphate-4,6-dipyrophosphate
19. D-chiro-inositol 1,3,4-triphosphate-2,5-dipyrophosphate
20. D-chiro-inositol 1,3,4-triphosphate-2,6-dipyrophosphate
21. D-chiro-inositol 1,3,4-triphosphate-5,6-dipyrophosphate
22. D-chiro-inositol 1,3,5-triphosphate-2,4-dipyrophosphate
23. D-chiro-inositol 1,3,5-triphosphate-2,6-dipyrophosphate
24. D-chiro-inositol 1,3,5-triphosphate-4,6-dipyrophosphate
25. D-chiro-inositol 1,3,6-triphosphate-2,4-dipyrophosphate
26. D-chiro-inositol 1,3,6-triphosphate-2,5-dipyrophosphate
27. D-chiro-inositol 1,3,6-triphosphate-4,5-dipyrophosphate
28. D-chiro-inositol 1,4,5-triphosphate-2,3-dipyrophosphate
29. D-chiro-inositol 1,4,5-triphosphate-2,6-dipyrophosphate
30. D-chiro-inositol 1,4,5-triphosphate-3,6-dipyrophosphate
31. D-chiro-inositol 1,4,6-triphosphate-2,3-dipyrophosphate
32. D-chiro-inositol 1,4,6-triphosphate-2,5-dipyrophosphate
33. D-chiro-inositol 1,4,6-triphosphate-3,5-dipyrophosphate
34. D-chiro-inositol 1,5,6-triphosphate-2,3-dipyrophosphate
35. D-chiro-inositol 1,5,6-triphosphate-2,4-dipyrophosphate
36. D-chiro-inositol 1,5,6-triphosphate-3,4-dipyrophosphate
37. D-chiro-inositol 2,3,4-triphosphate-1,5-dipyrophosphate
38. D-chiro-inositol 2,3,4-triphosphate-1,6-dipyrophosphate
39. D-chiro-inositol 2,3,4-triphosphate-5,6-dipyrophosphate
40. D-chiro-inositol 2,3,5-triphosphate-1,4-dipyrophosphate
41. D-chiro-inositol 2,3,5-triphosphate-1,6-dipyrophosphate 42. D-chiro-inositol 2,3,5-triphosphate-4,6-dipyrophosphate
43. D-chiro-inositol 2,3,6-triphosphate-1,4-dipyrophosphate
44. D-chiro-inositol 2,3,6-triphosphate-1,5-dipyrophosphate
45. D-chiro-inositol 2,3,6-triphosphate-4,5-dipyrophosphate
46. D-chiro-inositol 2,4,5-triphosphate-1,3-dipyrophosphate
47. D-chiro-inositol 2,4,5-triphosphate-1,6-dipyrophosphate
48. D-chiro-inositol 2,4,5-triphosphate-3,6-dipyrophosphate
49. D-chiro-inositol 2,4,6-triphosphate-1,3-dipyrophosphate
50. D-chiro-inositol 2,4,6-triphosphate-1,5-dipyrophosphate
51. D-chiro-inositol 2,4,6-triphosphate-3,5-dipyrophosphate
52. D-chiro-inositol 2,5,6-triphosphate-1,3-dipyrophosphate
53. D-chiro-inositol 2,5,6-triphosphate-1,4-dipyrophosphate
54. D-chiro-inositol 2,5,6-triphosphate-3,4-dipyrophosphate
55. D-chiro-inositol 3,4,5-triphosphate-1,2-dipyrophosphate
56. D-chiro-inositol 3,4,5-triphosphate-1,6-dipyrophosphate
57. D-chiro-inositol 3,4,5-triphosphate-2,6-dipyrophosphate
58. D-chiro-inositol 3,5,6-triphosphate-1,2-dipyrophosphate
59. D-chiro-inositol 3,5,6-triphosphate-1,4-dipyrophosphate
60. D-chiro-inositol 3,5,6-triphosphate-2,4-dipyrophosphate
61. D-chiro-inositol 4,5,6-triphosphate-1,2-dipyrophosphate
62. D-chiro-inositol 4,5,6-triphosphate-1,3-dipyrophosphate
63. D-chiro-inositol 4,5,6-triphosphate-2,3-dipyrophosphate
64. D-chiro-inositol 1-phosphate-2,3,4-tripyrophosphate
65. D-chiro-inositol 1-phosphate-2,3,5-tripyrophosphate
66. D-chiro-inositol 1-phosphate-2,3,6-tripyrophosphate
67. D-chiro-inositol 1-phosphate-2,4,5-tripyrophosphate
68. D-chiro-inositol 1-phosphate-2,4,6-tripyrophosphate
69. D-chiro-inositol 1-phosphate-2,3,6-tripyrophosphate
70. D-chiro-inositol 1-phosphate-3,4,5-tripyrophosphate
71. D-chiro-inositol 1-phosphate-3,4,6-tripyrophosphate
72. D-chiro-inositol 1-phosphate-3,5,6-tripyrophosphate
73. D-chiro-inositol 1-phosphate-4,5,6-tripyrophosphate
74. D-chiro-inositol 2-phosphate-1,3,4-tripyrophosphate
75. D-chiro-inositol 2-phosphate-1,3,5-tripyrophosphate
76. D-chiro-inositol 2-phosphate-1,3,6-tripyrophosphate
77. D-chiro-inositol 2-phosphate-1,4,5-tripyrophosphate
78. D-chiro-inositol 2-phosphate-1,4,6-tripyrophosphate
79. D-chiro-inositol 2-phosphate-1,5,6-tripyrophosphate
80. D-chiro-inositol 2-phosphate-3,4,5-tripyrophosphate
81. D-chiro-inositol 2-phosphate-3,4,6-tripyrophosphate
82. D-chiro-inositol 2-phosphate-3,5,6-tripyrophosphate
83. D-chiro-inositol 2-phosphate-4,5,6-tripyrophosphate
84. D-chiro-inositol 3-phosphate-1,2,4-tripyrophosphate
85. D-chiro-inositol 3-phosphate-1,2,5-tripyrophosphate
86. D-chiro-inositol 3-phosphate-1,2,6-tripyrophosphate
87. D-chiro-inositol 3-phosphate-1,4,5-tripyrophosphate
88. D-chiro-inositol 3-phosphate-1,4,6-tripyrophosphate
89. D-chiro-inositol 3-phosphate-1,5,6-tripyrophosphate
90. D-chiro-inositol 3-phosphate-3,4,5-tripyrophosphate
91. D-chiro-inositol 3-phosphate-3,4,6-tripyrophosphate
92. D-chiro-inositol 3-phosphate-3,5,6-tripyrophosphate
93. D-chiro-inositol 3-phosphate-4,5,6-tripyrophosphate Other Derivatives of Inositol as PI3K/AKT/Inhibitors
1. D-1-deoxy-2-O-methyl-D-chiroinositol-[1-(R)-2-methoxy-3-(octadecyloxy)propyl hydrogen phosphate]
2. D-1-deoxy-3-O-methyl-D-chiroinositol-[1-(R)-2-methoxy-3-(octadecyloxy)propyl hydrogen phosphate]
3. D-1-deoxy-4-O-methyl-D-chiroinositol-[1-(R)-2-methoxy-3-(octadecyloxy)propyl hydrogen phosphate]
4. D-1-deoxy-5-O-methyl-D-chiroinositol-[1-(R)-2-methoxy-3-(octadecyloxy)propyl hydrogen phosphate]
5. D-1-deoxy-6-O-methyl-D-chiroinositol-[1-(R)-2-methoxy-3-(octadecyloxy)propyl hydrogen phosphate]
6. D-2-deoxy-1-O-methyl-D-chiroinositol-[1-(R)-2-methoxy-3-(octadecyloxy)propyl hydrogen phosphate]
7. D-2-deoxy-3-O-methyl-D-chiroinositol-[1-(R)-2-methoxy-3-(octadecyloxy)propyl hydrogen phosphate]
8. D-2-deoxy-4-O-methyl-D-chiroinositol-[1-(R)-2-methoxy-3-(octadecyloxy)propyl hydrogen phosphate]
9. D-2-deoxy-5-O-methyl-D-chiroinositol-[1-(R)-2-methoxy-3-(octadecyloxy)propyl hydrogen phosphate]
10. D-2-deoxy-6-O-methyl-D-chiroinositol-[1-(R)-2-methoxy-3-(octadecyloxy)propyl hydrogen phosphate]
11. D-Chiro phosphatidyl inositol D-3-deoxy-1-O-methyl-D-chiroinositol-[1-(R)-2-methoxy-3-(octadecyloxy)propyl hydrogen phosphate]
12. D-Chiro phosphatidyl inositol D-3-deoxy-2-O-methyl-D-chiroinositol-[1-(R)-2-methoxy-3-(octadecyloxy)propyl hydrogen phosphate]
13. D-Chiro phosphatidyl inositol D-3-deoxy-4-O-methyl-D-chiroinositol-[1-(R)-2-methoxy-3-(octadecyloxy)propyl hydrogen phosphate]
14. D-Chiro phosphatidyl inositol D-3-deoxy-5-O-methyl-D-chiroinositol-[1-(R)-2-methoxy-3-(octadecyloxy)propyl hydrogen phosphate]
15. D-chiro phosphatidyl inositol D-3-deoxy-6-O-methyl-D-chiroinositol-[1-(R)-2-methoxy-3-(octadecyloxy)propyl hydrogen phosphate]
16. D-4-deoxy-1-O-methyl-D-chiroinositol-[1-(R)-2-methoxy-3-(octadecyloxy)propyl hydrogen phosphate]
17. D-4-deoxy-2-O-methyl-D-chiroinositol-[1-(R)-2-methoxy-3-(octadecyloxy)propyl hydrogen phosphate]
18. D-4-deoxy-3-O-methyl-D-chiroinositol-[1-(R)-2-methoxy-3-(octadecyloxy)propyl hydrogen phosphate]
19. D-4-deoxy-5-O-methyl-D-chiroinositol-[1-(R)-2-methoxy-3-(octadecyloxy)propyl hydrogen phosphate]
20. D-4-deoxy-6-O-methyl-D-chiroinositol-[1-(R)-2-methoxy-3-(octadecyloxy)propyl hydrogen phosphate]
21. D-5-deoxy-1-O-methyl-D-chiroinositol-[1-(R)-2-methoxy-3-(octadecyloxy)propyl hydrogen phosphate]
22. D-5-deoxy-2-O-methyl-D-chiroinositol-[1-(R)-2-methoxy-3-(octadecyloxy)propyl hydrogen phosphate]
23. D-5-deoxy-3-O-methyl-D-chiroinositol-[1-(R)-2-methoxy-3-(octadecyloxy)propyl hydrogen phosphate]
24. D-5-deoxy-4-O-methyl-D-chiroinositol-[1-(R)-2-methoxy-3-(octadecyloxy)propyl hydrogen phosphate]
25. D-5-deoxy-6-O-methyl-D-chiroinositol-[1-(R)-2-methoxy-3-(octadecyloxy)propyl hydrogen phosphate]
26. D-6-deoxy-1-O-methyl-D-chiroinositol-[1-(R)-2-methoxy-3-(octadecyloxy)propyl hydrogen phosphate]
27. D-6-deoxy-2-O-methyl-D-chiroinositol-[1-(R)-2-methoxy-3-(octadecyloxy)propyl hydrogen phosphate]
28. D-6-deoxy-3-O-methyl-D-chiroinositol-[1-(R)-2-methoxy-3-(octadecyloxy)propyl hydrogen phosphate]
29. D-6-deoxy-4-O-methyl-D-chiroinositol-[1-(R)-2-methoxy-3-(octadecyloxy)propyl hydrogen phosphate]
30. D-6-deoxy-5-O-methyl-D-chiroinositol-[1-(R)-2-methoxy-3-(octadecyloxy)propyl hydrogen phosphate]
1. 1D-6-hydroxymethyl-chiro-inositol-1-(R)-2-methoxy-3-O-octadecyl-sn-glycerocarbonate
2. 1D-6-hydroxymethyl-chiro-inositol-2-(R)-2-methoxy-3-O-octadecyl-sn-glycerocarbonate
3. 1D-6-hydroxymethyl-chiro-inositol-3-(R)-2-methoxy-3-O-octadecyl-sn-glycerocarbonate
4. 1D-6-hydroxymethyl-chiro-inositol-4-(R)-2-methoxy-3-O-octadecyl-sn-glycerocarbonate
5. 1D-6-hydroxymethyl-chiro-inositol-5-(R)-2-methoxy-3-O-octadecyl-sn-glycerocarbonate
6. 1D-5-hydroxymethyl-chiro-inositol-1-(R)-2-methoxy-3-O-octadecyl-sn-glycerocarbonate
7. 1D-5-hydroxymethyl-chiro-inositol-2-(R)-2-methoxy-3-O-octadecyl-sn-glycerocarbonate
8. 1D-5-hydroxymethyl-chiro-inositol-3-(R)-2-methoxy-3-O-octadecyl-sn-glycerocarbonate 9. 1D-5-hydroxymethyl chiro-inositol-4-(R)-2-methoxy-3-O-octadecyl-sn-glycerocarbonate
10. 1D-5-hydroxymethyl-chiro-inositol-6-(R)-2-methoxy-3-O-octadecyl-sn-glycerocarbonate
11. 1D-4-hydroxymethyl-chiro-inositol-1-(R)-2-methoxy-3-O-octadecyl-sn-glycerocarbonate
12. 1D-4-hydroxymethyl-chiro-inositol-2-(R)-2-methoxy-3-O-octadecyl-sn-glycerocarbonate
13. 1D-4-hydroxymethyl-chiro-inositol-3-(R)-2-methoxy-3-O-octadecyl-sn-glycerocarbonate
14. 1D-4-hydroxymethyl-chiro-inositol-5-(R)-2-methoxy-3-O-octadecyl-sn-glycerocarbonate
15. 1D-4-hydroxymethyl-chiro-inositol-6-(R)-2-methoxy-3-O-octadecyl-sn-glycerocarbonate
16. 1D-3-hydroxymethyl-chiro-inositol-1-(R)-2-methoxy-3-O-octadecyl-sn-glycerocarbonate
17. 1D-3-hydroxymethyl-chiro-inositol-2-(R)-2-methoxy-3-O-octadecyl-sn-glycerocarbonate
18. 1D-3-hydroxymethyl-chiro-inositol-4-(R)-2-methoxy-3-O-octadecyl-sn-glycerocarbonate
19. 1D-3-hydroxymethyl-chiro-inositol-5-(R)-2-methoxy-3-O-octadecyl-sn-glycerocarbonate
20. 1D-3-hydroxymethyl-chiro-inositol-6-(R)-2-methoxy-3-O-octadecyl-sn-glycerocarbonate
21. 1D-2-hydroxymethyl chiro-inositol-1-(R)-2-methoxy-3-O-octadecyl-sn-glycerocarbonate
22. 1D-2-hydroxymethyl-chiro-inositol-3-(R)-2-methoxy-3-O-octadecyl-sn-glycerocarbonate
23. 1D-2-hydroxymethyl-chiro-inositol-4-(R)-2-methoxy-3-O-octadecyl-sn-glycerocarbonate
24. 1D-2-hydroxymethyl-chiro-inositol-5-(R)-2-methoxy-3-O-octadecyl-sn-glycerocarbonate
25. 1D-2-hydroxymethyl-chiro-inositol-6-(R)-2-methoxy-3-O-octadecyl-sn-glycerocarbonate
26. 1D-1-hydroxymethyl-chiro-inositol-2-(R)-2-methoxy-3-O-octadecyl-sn-glycerocarbonate
27. 1D-1-hydroxymethyl-chiro-inositol-3-(R)-2-methoxy-3-O-octadecyl-sn-glycerocarbonate
28. 1D-1-hydroxymethyl-chiro-inositol-4-(R)-2-methoxy-3-O-octadecyl-sn-glycerocarbonate
29. 1D-1-hydroxymethyl-chiro-inositol-5-(R)-2-methoxy-3-O-octadecyl-sn-glycerocarbonate
30. 1D-1-hydroxymethyl-chiro-inositol-6-(R)-2-methoxy-3-O-octadecyl-sn-glycerocarbonate Another aspect of the invention is to regulate metabolic pathways in rapidly growing tissues. This relates to all cancer cells, obesity, diabetes, neurodegenerative diseases, and inflammation without limitation to inflammatory conditions or autoimmune. The inventions also show methods, compositions, and kits for the use of activators or deactivators of PKM2 or PKM1 for increasing tumor suppressor genes, specifically P53 or deactivating a wild type p53 (defective tumor suppressor gene).

Another aspect of the invention is to activate or upregulate P53 tumor suppressor with inositol and or phosphates (but not limited in any way). P53 is one of the most frequently mutated genes in cancer. P53 appears to modulate the balance between the utilization of respiration and glycolytic pathways and Cytochrome C oxidase (SCO2) appears to be the downstream mediator of this effect. This SCO2 protein enzyme is crucial for regulating the cytochrome c oxidase (cox complex) which is the major site of oxygen use in animals. By disrupting the SCO2 gene or upregulating tumor suppressor gene p53 with inositol phosphates, the inventor believes that the compounds will turn off the metabolic switch towards glycolysis and deactivate phosphotyrosine binding or signaling.

In yet other aspects of the invention, it relates to manipulating cell growth and differentiation in culture for implantation of such cells. In this context, the invention relates to treatments for regenerating neural tissue, hepatic tissue, pancreatic tissue, intestinal tissue, spleenic tissue, cardiac tissue, among others. In still other embodiments, the invention relates to regulating or inhibiting growth of cells and therefore finds use in the treatment of excessive or inappropriate hair growth conditions, psoriasis, actinic keratosis, acne, miscellaneous dermatitis conditions, etc. In yet other embodiments, the invention relates to inducing an anti-angiogenic state in local and distant metastatic tumors.

The invention further relates to correcting the inherent mechanism of tumor stem cell autoregulation. Yet another embodiment of the invention relates to decreasing the risk of deep vein thrombosis (DVT's) and Pulmonary emboli (PE's) while using chemotherapeutic agents, antiestrogens such as tamoxifen etc., hormonal therapies such as androgen ablative therapies, or estrogenic hormone therapy. The invention still further relates to reducing the numbers and size of tumors locally or distant especially in breast cancers, but also cancers originating from blood, colon, lung, liver, pancreas, cervix, prostate, skin, and soft tissue.

The invention further relates to preventing breast cancer or precursors thereof in utero.

BACKGROUND OF THE INVENTION

The present invention relates to compounds that are of the inositol family and for many of the uses set forth herein specifically the D-chiroinositol family of compounds. Most are derivatives of the basic parent of the family, but in some indications, even the basic parent was not previously known or thought to be useful in the contexts indicated. As indicated in the above fields of the invention, the invention is applicable to a wide array of utilities a number of which are addressed separately in this background section below.

I. Fetal Malformation

Fetal malformations are a continuing medical problem in serious need of prevention and treatment. These malformations can result in innocuous defects that pose no health or psychological issues, to those that pose primarily social or psychological issues (such as webbed digits, etc.), to those that pose medical issues of varying degrees of severity. Some of the more medically severe malformations include neural tube defects (such as, among others, anencephaly where the brain is underdeveloped or there is an incomplete skull, encephalocele, where there is a hole in the skull through which tissue protrudes, and spina bifida, where a portion of the spine is exposed) to cranio-facial defects (such as, among others, cleft lip and cleft palate) to imperforate anus (where the anal opening doesn't form properly leaving no exit for intestinal contents, or intestinal/rectal emptying into inappropriate structures such as the bladder, ureter, uterus or vagina). Other birth defects like neural derived brain tumors are not so evident immediately after birth and rarely if ever seen at birth. For example, the onset of pediatric tumors like primitive neuroectodermal tumors of the central nervous system (PNET'S) is insidious. There is considerable controversy regarding the histiogenesis of these tumors, but a genetic loci of interest in the pathnogenesis of these central nervous system derived tumors includes Shh gene pathways.

Cleft palate children were found to have low red blood cell zinc levels and low myo-inositol levels (Krapels, et al: *Myo-inositol, glucose and zinc status as risk factors for non-syndromic cleft lip with or without cleft palate in* offspring: a case-control study, BJOG, 2004 July; 111(7): 661-8). Impairment of the Folbp1 gene function adversely impacts the expression of several critical signaling molecules. Mis-expression of these molecules, perhaps mediated by Shh may potentially contribute to the observed failure of the neural tube and the development of craniofacial defects in the mutant mice (Birth Defects Research, Wiley Interscience, 2003).

II. Signaling Pathways

In molecular biology, 'signal transduction' refers to any process by which a cell converts one kind of signal or stimulus into another. Most processes of signal transduction involve ordered sequences of biochemical reactions inside the cell, which are carried out by enzymes, activated by second messengers, resulting in the signal transduction pathway. These processes are usually quick, lasting milliseconds in the case of sodium, potassium and calcium ion fluxes, or minutes for the activation of protein and lipid-mediated kinase cascades. However, some signaling cascade events can take days and many hours. (As is the case with gene expression), to complete. The number of proteins and other molecules participating in the events involving signal transduction increases as the process starts from the initial stimulus, resulting in a "signal cascade," that usual begins with a relatively small stimulus that elicits a larger response. This is referral to as "amplification of the signal" where the signal spreads across a spatial concentration gradient. The continued cell growth and/or death of a cell are some of the cellular responses to extracellular stimulation that require signal transduction as well. Gene activation leads to further cellular effects, like activation of transcription factors which are also the result of another signal transduction cascade. This cascade leads to activate yet more genes.

Most mammalian cells require constant growth factor stimulation to control not only cell division but also survival. In the absence of signal transduction, programmed cell death ensues in most cells. Such requirements for extra-cellular stimulation are necessary for controlling cell behavior in the multi-cellular organisms. Signal transduction pathways are known to be so central to biological processes that it is not surprising that a large number of diseases have been attributed to their disregulation and cross talk. Discussed below is how signal transduction can disrupt genes that can lead to various diseases.

Disruptions of genes in one pathway can also have deleterious effects in other pathways and may result in serious dysmorphogensis or cancer years later. For a better understanding of this aspect of the present invention, a basic overview of some of the genes and signaling pathways that may be affected by consequences of alterations in genes, their products, and specific exposures is in order. This also requires some understanding of the pathways involved in formation, embryonic development, and cancer.

During embryogenesis a simple, patterned body plan is established. To establish this organization, the cells of the embryo need to become specified and must differentiate into cell types in an integrated manner. The genetic regulation of this process is addressed here. In animals, cell-cell communication involving extracellular signals and cell surface-bound receptors plays an important role in cell fate decisions during embryogenesis (Johnston and Nüsslein-Volhard, 1902). Probably the best characterized signaling events in embryo patterning are those that involve sonic hedgehog (Shh). Mutations in the Shh genes and the genes that encode its downstream intracellular signaling pathway and subsequent responses can set the pattern for various birth defects and cancels in both prenatal and post natal development (Mol Mod Today, 1998). Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are involved in embryonic patterning in vertebrate development from the earliest establishment of the body plan, to the patterning of the organ systems, to the generation of diverse cell types during tissue differentiation (Davidson, E., (1990) Development 108: 365-389; Gurdon, J. B., (1992) Cell 68: 185-199; Jessell, T. M. et al., (1992) Cell 68: 257-270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential or convergent, such that an initial induction between two cell types leads to a progressive amplification of diversity. Moreover, inductive interactions occur not only in embryos, but in adult cells as well, and can act to establish and maintain morphogenetic patterns as well as induce differentiation in cell types (J. B. Gordon (1992) Cell 68:185-199). These cells can also act to establish and maintain morphogenetic patterns as well as induce differentiation (J. B. Gurdon (1992) Cell 68:185-199). The involvement of signal transduction pathways in the inhibition of gene expression and the occurrence of frequent allelic deletions in humans and animals support a tumor suppressor function for these pathways. Their role in the regulation of embryonic pattern formation known to be involved in cell signaling and intercellular communication provides a possible mechanism of fetal malformations, birth defects, autoimmune inflammatory diseases, inflammation, drug resistance, anti-angiogenesis, and cancers.

Notwithstanding the above, there is still a tremendous amount that is still not fully understood in the art about the nature of the all the mechanisms involved in the etiology of these malformations and diseases and how to appropriately intervene to reduce or prevent the occurrence of such defects. Thus, we are also investigating the possibility that many signaling pathways comprise multiple steps and cross convergences along the feedback loop. Nevertheless, we are closer to prevention of these diseases, and better treatment options that will eventually improve the quality of many patients' lives. The role of D-chiro-inositol its steroisomers and/or its phosphates and other derivatives among these pathways mentioned above, and their likely cross-talk in regulation of embryonic patterning, cancer, inflammatory autoimmune diseases, inflammation is now addressed in this application.

III. Fetal Alcohol Syndrome

Fetal alcohol syndrome (FAS) is one of the most common, preventable causes of devastating congenital structural birth defects to major organs like the brain, heart and kidneys and to varying defects of the face and limbs. It may occur as often as neural tube defects. According to recent literature, at least 33% to 50% of children born to chronic alcoholic mothers show some signs of fetal alcohol syndrome. Fetal alcohol syndrome remains a significant psychosocial and clinical challenge. While there have been great strides in preventing neural tube defects with folic acid, there are no known truly preventative strategics for preventing fetal alcohol syndrome related birth defects. One recent article (Li, et al; *Fetal alcohol exposure impairs hedgehog choles-* terol modification and signaling, Laboratory Investigation (2007) 87, 231-240 (Jan. 22, 2007)) discusses results in the zebrafish that exposure of zebrafish embryos to low levels of alcohol during gastrulation blocks modification of Sonic hedgehog by cholesterol and lead to permanent developmental defects that resemble fetal alcohol syndrome defects, and further that administration of cholesterol rescues the Sonic hedgehog function and prevents the defects in zebrafish. Unfortunately, cholesterol has a significant number of problems of its own that make it generally an unacceptable therapy for use in the human population and other treatment avenues are desired.

Ofori, et al *Risk of congenital anomalies in pregnant users of statin drugs*, British Journal of Clinical Pharmacology, vol. 64, No. 4, October 2007, pp 496-509, states that because cholesterol is known to be essential for fetal development, statins, which inhibit cholesterol production, have been considered potential teratogens, and therefore have been contraindicated in pregnancy. Ofori states that from their database of 288 they did not find evidence of increased risk in women who filled prescriptions for statins during pregnancy as compared to those who stopped statin use before pregnancy (between 1 year and 1 month before pregnancy) and compared to women who used fibrates during pregnancy based on live births. They do state however, that conclusions remain uncertain due to the lack of data about non-live births. There were no matched controls in this study either.

A posting on www.medpagetoday.com/OBGYN/Pregnancy/11317 published Oct. 14, 2008, by Gever, et al *Statins May Prevent Some Miscarriages* indicates that antiphospholipid antibody seen with patients with autoimmune inflammatory diseases induced miscarriages may be prevented by administration of the statins simvastatin and pravastatin. Thus, statin use in pregnancy in those showing predisposition to or symptoms of antiphospholipid antibodies is desirable. (See also Weiler, *Tracing the molecular pathogenesis of antiphospholipid syndrome*, J. Clin. Invest. 118(10): 3276-3278 (2008)).

IV. Autoimmune and Inflammatory Diseases

The present invention also relates to inflammatory autoimmune diseases that are triggered and promoted by abnormal kinase activity due to defective cell signaling. Interferon alpha (IFN-alpha) has been used for a decade to treat viral hepatitis, is a disease that effects approximately 350 million per year worldwide, more than half of those viral hepatitis patients respond poorly to drugs. It appears that high levels of tumor necrosis factor (TNF) correlate highly with resistance to interferon alpha therapy. There is an urgent need to find appropriate treatments for interferon resistance without adding more side effects to the already compromised liver. The methods and compounds are provided for treating diseases associated with abnormal activity of protein kinases. The method comprises administration of a specific or selective AKT inhibitor (for example D-3-Deoxy-2-O-methyl-D-Chiro-inositol-[1-(R)-2-methoxy-3-(octadecyloxy) propyl HPO4-] (hydrogen phosphate)) with interferon alpha (IFN-alpha) to a patient in therapeutically effective amounts; and administering a kinase inhibitor to the patient in therapeutically effective amount, such that the in vivo activity of the high levels of tumor necrosis factor (TNF) is reduced relative to that prior to the treatment so in order to overcome resistance to INF-alpha therapy. Interferon-alpha is currently the only well-established treatment for chronic-active viral hepatitis that affects millions world wide. It is thought that the activity of interferon is mediated by inducing expression of antiviral proteins and modulation of the immune system. Even though interferon has been used widely for many years for the treatment of viral hepatitis, most of those patients respond poorly. The mechanism underlying this problem remains unclear at this point, although both genetic and molecular implications must be considered. There have been many attempts to improve patient response to interferon by combining interferon with other anti-viral agents (i.e., Ribivarin). It appears that only a small number of patients responded to this attempt to increase the efficacy of combined interferon and Ribivarin. Thus, it is an urgent medical need to develop a new combination of compounds to improve interferon alpha response in patients with chronic-active hepatitis.

A number of acute and chronic inflammatory diseases have also been associated with very high amounts of circulating inflammatory cytokines and interleukin 1,6,8. These cytokines include but not limited to Tumor necrosis factor (TNF)-a cytokine involved in systemic inflammation. TNF also causes apoptotic cell death, cellular proliferation, inflammation, differentiation, tumorigenesis, and viral replication. But TNF's primary role is in the regulation of immune type of cells and their dysregulation and overproduction have been implicated in those diseases described above. Interleukin 1 beta, interleukin 6, interleukin 8 are also other types of cytokines responsible for inflammatory response in a variety of human diseases.

The phosphoinositide 3-kinase (PI3K)/Akt signaling pathway plays a pivotal role in cellular proliferation and growth signaling as described above. It involves the downstream activation of the protein kinase Akt. PtdIns (3,4)P2 (biphosphate) and ptdIns(3,4,5)P3(triphosphate) lipids produced by PI3K are able to bind Akt recruiting it to the plasma membrane where PDK1 and PDK2 phosphorylate it to its active form. This allows Akt to target proteins involved in cell death. Due to the constitutive activation of PI3K pathway in many cancers and immune mediated signaling pathways this pathway may produce systemic autoimmunity and resistance to interferon alpha for people with chronic, active viral hepatitis and chronic autoimmune inflammatory disease. Therefore, the inventor's research is helping to elucidate the role of this pathway and how perturbations that leads to a deregulated activation in this pathway. Inhibition of this pathway with combination therapy is a novel treatment for cancer and inflammatory disease states.

The phosphatidylinositol 3-[OH] kinase (PI3K)/Akt-(Protein kinase B) pathway is also important for survival such as platelet derived growth factor (PDGF), nerve growth factor (NGF) and insulin-like growth factor-1 (IGF-1), promote cell survival under various conditions by inducing the activity of PI3K. Activated PI3K leads to the production of phosphatidylinositol (3,4,5)-triphosphate (PtdIns(3,4,5)-P3), a second messenger which in turn binds to, and promotes the activation of, the serine/threonine kinase Akt, which contains a pleckstrin homology (PH)-domain (Franke et al, Cell, 88:435-437, 1997).

Recent Literature analysis of AKT levels in autoimmune inflammatory diseases protein Kinase B (Akt) appears to be overexpressed or hyperactive in a significant number of inflammatory autoimmune diseases such as Rheumatoid arthritis, Systemic lupus, Inflammatory Bowel Diseases, Chron's disease and others. It is also postulated here that high levels of tumor necrosis factor is mediated by dyregulated PI3k signaling which can lead to Inteferon alpha resistance seen in many patients with viral hepatitis. Furthermore, PTEN is a tumor suppressor gene mutated in many human sporadic cancers and hyperactive immune systems. Those with hereditary cancer syndromes such as Bannayan-Zonana syndrome and Cowden syndromes are purportedly pten deficient (Lieaw et al. nature genetics 16:64-67. Functionally, PTEN is a dual protein and lipid phosphatase enzyme (Li et al. science 275:1943-1947, 1997) and the major substrate of PTEN is phosphatidyl inositol-3,4,5-triphosphate (PIP3), a second messenger molecule then produced through PI3K signaling activation induced by growth factor stimulation. PIP3 activates the serine-threonine kinase PKB/Akt which is involved in anti-apoptosis, proliferation, and oncogenesis. PTEN negatively regulates cell survival by dephosphorylating PIP3 by enzymatic activation. Recent literature cited studies that showed that a null mutation of Pten in mice is lethal during embryogenesis. In a study, it was demonstrated that PKB/Akt pathway is hyperactivated in the absence of Pten). Furthermore. $Pten^{+/-}$ mice frequently develop T cell lymphomas, and endometrial, prostatic, and breast cancers. Autoimmune disorders are also prevalent in Pten deficient mice. In T cell-specific Pten-deficient mice, it showed that $CD4^+$ lymphomas and autoimmune disorders were prevalent. These observations support the role of PI3k/Akt signaling pathways play an important role for regulating cell survival, apoptosis in transforming cells into cancerous, metastatic tumors.

Three members of the Akt/PKB subfamily of second-messenger regulated serine/threonine protein kinases have been identified and termed Akt1/PKB.alpha., Akt2/PKB.beta., and Akt3/PKB.gamma., respectively. The isoforms are homologous, particularly in regions encoding the catalytic domains. Akt/PKBs are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt/PKB. The current model of Akt/PKB activation proposes recruitment of the enzyme to the membrane by 3'-phosphorylated phosphoinositides, where phosphorylation of the regulatory sites of Akt/PK B by the upstream kinases occurs (B. A. Hemmings, Science 275:628-630 (1997); B. A. Hemmings, Science 276:534 (1997); J. Downward, Science 279:673-674 (1998)).

Phosphorylation of Akt1/PKB.alpha. occurs on two regulatory sites, Thr.sup.308 in the catalytic domain activation loop and on Ser.sup.473 near the carboxy terminus (D. R. Alessi et al. EMBO J. 15:6541-6551 (1996) and R. Meier et al. J. Biol. Chem. 272:30491-30497 (1997). Equivalent regulatory phosphorylation sites occur in Akt2/PKB.beta. and Akt3/PKB.gamma. The upstream kinase, which phosphorylates Akt/PKB at the activation loop site has been cloned and termed 3'-phosphoinositide dependent protein kinase 1 (PDK1). PDK1 phosphorylates not only Akt/PKB, but also p70 ribosomal S6 kinase, p90RSK, serum and glucocorticoid-regulated kinase (SGK), and protein kinase C (B. A. Hemmings, Science 276:534 (1997); J. Downward, Science 279:673-674 (1998).

Inhibition of Akt activation and activity can be achieved by inhibiting PI3K with inhibitors already known in the prior art such as LY294002 and wortmannin. However, some research has suggested PI3K inhibition has the potential to indiscriminately affect not just all three Akt isozymes but also other PH domain-containing signaling molecules that are dependent on PtdIns(3,4,5)-P3, such as the Tec family of tyrosine kinases. Furthermore, it has been disclosed that Akt can be activated by growth signals that are independent of PI3K.

At the same time, Akt activity can be inhibited by blocking the activity of the upstream kinase PDK1. No specific PDK1 inhibitors have been disclosed. However, a recent study interestingly suggested that $Ins(1,3,4,5,6)P_5$ and $InsP_6$, as well as $Ins(1,3,4,5)P_4$, were found to bind PDK1 with high affinity, with $K_1$ values of 20-60 nM. In contrast, $Ins(1,4,5)P_3$ binding to PDK1 could not be detected. The hydrogen bonds to the D1-phosphate appear to play a crucial role in mediating binding of inositol phosphates to PDK1. Furthermore, they next investigated whether $Ins(1,3,4,5,6)P_5$ and $InsP_6$ could compete with $PtdIns(3,4,5)P_3$ in regulating the activation of PKB by PDK1 in an in vitro assay. The results showed with a dose given of 300 μM $InsP_6$ or $Ins(1,3,4,5,6)P_5$ inhibited the activation and phosphorylation of PKB in the presence of $PtdIns(3,4,5)P_3$, by over 80%. $InsP_6$ or $Ins(1,3,4,5,6)P_5$ did not directly inhibit PDK1 catalytic activity, as the phosphorylation of the PDK tide peptide substrate by PDK1 was not affected by D6-phosphorylated inositol phosphates. It has also been reported that increasing extracellular $Ins(1,3,4,5,6)P_5$ in cells lowered PKB activation, through an undefined mechanism (Piccolo et al, 2004). It is the inventor's belief that different inositol polyphosphates interact differently. Some agozine the activity in the presence of other substrates while others antagonize the activation of these signaling pathways. EMBO J. 2004 Oct. 13; 23(20): 3918-3928.

The inventor does not believe that the inhibition of PDK1 would result in inhibition of multiple protein kinases whose activities depend on PDK1, such as atypical Protein Kinase C PKC isoforms, SGK, and S6 kinases if the different invention compounds were utilized in a selective, specific manner in the presence of different substrates. For example, phosphorylation of PKC by PDK-1 may not require the PH domain of PDK-1 and may not be affected by 3'-phosphoinositides. Thus, despite what earlier literature suggests, the inventor believes that perhaps not all of these enzymes are dependent upon phosphoinositide phosphorylation and that there may be some other lipid signaling pathway present that is involved in cross-talk.

Therefore, further embodiments of the invention compounds are envisioned to be selective for inhibiting different isoenzymes. The compounds of the instant invention are inhibitors of the activity of Akt and PDK1 are thus useful in the treatment of cancer, in particular cancers associated with irregularities in the activity of Akt and/or GSK3. Such cancers include, but are not limited to ovarian, pancreatic and breast cancer.

In an embodiment of the invention, the instant compound is a selective inhibitor whose inhibitory efficacy is dependent on the PH domain. In this embodiment, the compound exhibits a decrease in in vitro inhibitory activity or no in vitro inhibitory activity against truncated Akt proteins jacking the PH domain.

In a further embodiment, the instant compound is selected from the group of a selective inhibitor of Akt1, a selective inhibitor of Akt2 and a selective inhibitor of both Akt1 and Akt2.

In another embodiment, the instant compound is selected from the group of a selective inhibitor of Akt1, a selective inhibitor of Akt2, a selective inhibitor of Akt3 and a selective inhibitor of two of the three Akt isoforms.

In another embodiment, the instant compound is a selective inhibitor of all three Akt isoforms, but is not an inhibitor of one, two or all of such Akt isoforms that have been modified to delete the PH domain, the hinge region or both the PH domain and the hinge region.

In another embodiment with a different inositol pyrophosphate or inositol polyphosphate (or further derivatives of either), the invention is a selective inhibitor of PDK1.

The present invention is further directed to a method of inhibiting Akt activity which comprises administering to a mammal in need thereof a pharmaceutically effective amount of the instant compound to be protective against TNF mediated cell apoptosis as well as sensitize cells to interferon alpha through modulations of the PI3K signaling activity.

The compounds of the instant invention are inhibitors of the activity of PI3-kinase/PDK1/AKT-dependent signaling pathway are thus useful in the treatment of, cancers associated with irregularities in the activity of Akt and/or GSK3. Such cancers include, but are not limited to ovarian, pancreatic and breast cancer. They are also useful in the treatment of inflammatory conditions, and in the treatment of elevated Tumor Necrosis Factor in chronic inflammatory states such as like Rheumatoid Arthritis, Systemic Lupus Erythematosus, Hepatitis (A, B, C, and/or D), Ankylosing Spondylitis, Inflammatory Bowel Disease and Psoriasis, but not limited to only these inflammatory conditions.

Chronic inflammation has been implicated in the pathogenesis of many severe autoimmune disorders, as well as in diabetes, pulmonary diseases, and cancer. Inflammation also accompanies most solid cancers. Some researchers investigated the role of the major proinflammatory cytokine tumor necrosis factor α (TNFα) in the malignancy of Pancreatic ductal adenocarcinoma (PDAC) cells in vitro and in vivo. In vitro, TNFα strongly increased invasiveness of Colo357, BxPc3, and PancTuI cells and showed only moderate antiproliferative effect. TNFα treatment of mice bearing orthotopically growing PDAC tumors led to dramatically enhanced tumor growth and metastasis. Notably, they found that PDAC cells themselves secrete TNFα. Although inhibition of TNFα with infliximab or etanercept only marginally affected proliferation and invasiveness of PDAC cells in vitro. In severe combined immunodeficient mice with orthotopically growing Colo357, BxPc3, or PancTuI tumors, human-specific anti-TNF antibody infliximab reduced tumor growth and metastasis by about 30% and 50%, respectively. Infliximab and etanercept reduced the number of liver metastases by 69% and 42%, respectively, as well as volumes of recurrent tumors by 73% and 51%. Thus, tumor cell-derived TNFα appears to play a profound role in malignancy of PDAC, and inhibition of TNFα represents a promising therapeutic option for cancers that are caused by chrome inflammation that is one cause of cancer or solid tumors that transform to metastatic tumors. [Cancer Res 2008; 68(5): 1443-50]

V. Invention Compound and Folate

In one aspect of the invention, the invention further relates to D-chiroinositol and derivatives thereof, more specifically D-chiro-inositol, phosphates thereof, and other derivatives of each as more fully detailed below. In addition, this aspect of the invention also relates to folates. The number of births presenting with spina bifida has been reduced in recent years in patients at risk of having such defects by having adequate folate levels in the mother just before and during the first trimester of pregnancy. More specifically, if a woman takes folic acid before conception and during early pregnancy, the risk of the fetus developing a neural tube defect is reduced by about 70%. Unfortunately, folate supplementation still does not prevent all such cases, and presumably, the impairment of the Folbp1 due to aberrant sonic hedgehog signaling likely mediates the acquisition of folate resistance of the mother. The remaining 30% risk is still substantial. In a Research Review from Neurosciences and Mental Health 2005 from Great Ormond Street Hospital, the use of inositol in combination with folate therapy is mentioned as being explored. However, no particular type of inositol is mentioned nor is any dosage amount or regimen.

Inositol prevents expression of a genetic model of neural lube defects in mice; Nutrition Reviews, May 1997 reports that myo-inositol reduced the incidence of neural tube defects in mouse models that are folate resistant. The curly tail model is particularly resistant to folate therapy. (Human Reproduction, Vol. 17, No. 9, 2451-2458) and frequently used to test for activity in these conditions. Cogram et al, Human Reproduction, Vol. 17, No. 9, 2451-2458, states that D-chiro-inositol alone reduced frequency of spina bifida in this model to a greater extent than myo-inositol alone. Without being bound thereto, it is the inventor's belief that in the present invention D-chiroinostitol (or a phosphorylated or oilier derivative thereof, preferably combinations of two or more selected from D-chiroinositol, its phosphates, or other derivatives thereof) stimulates these signaling mechanisms, activating certain isoforms of protein kinases that appear to be required for neural tube defects. Other relevant literature includes: Frederick, et al; *An essential role for an inositol polyphosphate multikinase, Ipk2, in mouse embryogenesis and second messenger production*, PNAS Jun. 14, 2005, Vol 102, No. 24, 8454-8459; Riobo, et al. *Phosphoinositide 3-kinase and Akt are essential for sonic Hedgehog signaling*, PNAS Mar. 21, 2006, Vol. 103, No. 12, 4505-4510.

Meyers, et al; *Folic Acid Supplementation and Risk for Imperforate Anus in China*; American Journal of Epidemiology, Vol. 154, No. 11: 1051-1056, 2001 reports on a public health campaign in China in 1993 to 1995, where women were requested to take 400 mg folic acid, with or without other vitamins daily from their pre-marital examination through the end of their first trimester of pregnancy. The rate of imperforate anus was calculated to be 3.1 per 10,000 births for those not taking folic acid compare to 1.6 per 10,000 births for those taking folic acid. The authors conclude that folic acid may reduce imperforate anus risk.

In addition, Mo et al, *Anorectal malformations Caused by Defects in Sonic Hedgehog signaling*, American Journal of Pathology 2001, 159, 765-774 report on a mutant mouse with various defects in the Sonic Hedgehog signaling pathway that presents with a number of distal hindgut defects that appear to the authors to mimic human anorectal deformations. An excellent review of inositol and some of its phosphates is given in Fisher, et al; *Inositol and higher inositol phosphates in neural tissues: homeostasis, metabolism and functional significance*, Journal of Neurochemistry. Vol 82, 736 August 2002.

In some embodiments of the present invention, folic acid of the formula

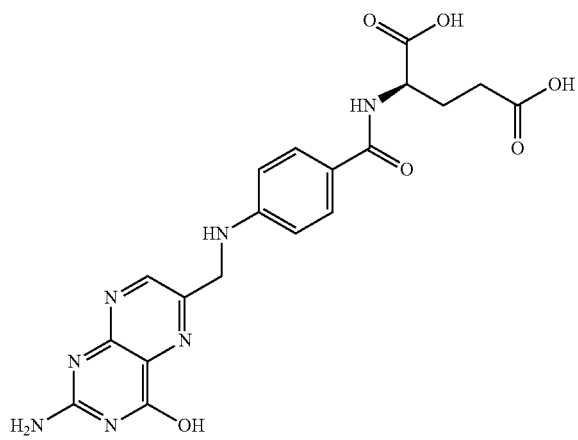 [SMILES: Nc1nc(O)c2nc(CNc3ccc(C(=O)N[C@H](CCC(=O)O)C(=O)O)cc3)cnc2n1]

and (D)-chiro-inositol or a phosphatidyl-chiro-inositol or a complex of the present invention are linked via a covalent bond, preferably with an ester bond formed between a carboxyl of the folic acid and hydroxyl of the inositol. Alternatively, with the phosphorylates or other derivatives of the invention compounds in which the invention compounds have a free acidic group (the —OH of a phosphate, sulfate, sulfonate, or carbonate, the linkage can be an ester between a free hydroxy group of the folic acid and the acidic group of the invention compound, or further an acid anhydride between the folic acid acidic group and the invention compound acidic group, although the acid anhydrides are more prone to rapid hydrolysis. All of these compounds having an invention compound component and a folic acid component are further compounds within the invention. The inventor is using the folic acid as guiding media to target tumor cells with the invention compounds as described. Folic acid polysaccharides (where the polysaccharide does not contain an inositol) are analogously suitable and part of the invention forming Folic acid polysaccharide-D chiro inositol complexes.

VI. Inositols

Inositols are a group of compounds that have the following structure

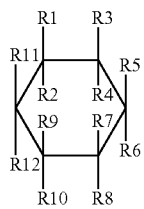

where each of the R groups is either H or OH, but each carbon of the ring has one H and one OH. The most common form is myo-inositol, which is available to some degree from dietary sources. Myo-inositol requires that all of R1, R3, R5, R8, R9, and R12 are OH and R2, R4, R6, R7, R10, and R11 are all hydrogen. Epi-inositol and scyllo-inositol are the other two most abundant forms (each being substantially less than the myo-inositol in terms of abundance). D-chiro-inositol is not available from dietary sources and is the isomer where R1, R3, R6, R8, R9, and R12 are OH and R2, R4, R5, R7, R10, and R11 are hydrogen, in other words, D-chiro-inositol differs from myo-inositol in the inversion of R5/R6.

There are a total of ten isomers of inositol, and for those that have found potential medicinal or nutritional use, many of the uses are truly limited to particular isomers and/or phosphates thereof (where one or more of the hydroxyl groups are phosphorylated), while for other uses (such a in connection with blood glucose regulation) more than one inositol isomer has been found useful or is projected to be useful. For example, recently scyllo inositol has been found to prevent the accumulation of amyloid β deposits and improved cognitive ability in Alzheimer's patients. (McLaurin, et al, *Inositol Stereoisomers Stabilize an Oligomeric Aggregate of Alzheimer Amyloid beta Peptide and Inhibit A beta-induced Toxicity*, J. Biol. Chem., Vol. 275, Issue 24, 18495-18502, Jun. 16, 2000; and Research News from Howard Hughes medical Institute Jun. 11, 2006 *A Sweet Solution to Alzheimer's Disease?*) Myo-inositol was found not to be effective in this condition. Scyllo-inositol worked when given before symptoms appeared as well as after symptoms appeared in this indication, while epi-inositol only worked at all when given before disease onset. Interestingly, scyllo-inositol has been reported to be an "inositol" uptake inhibitor causing similar fetal development defects in non-hyperglycemic pregnancies as seen in hyperglycemic pregnancies (Cederberg; *Oxidative Stress, antioxidative defense, and Outcome in Experimental Diabetic pregnancy*; Comprehensive Summaries of Uppsala Dissertations from the Faculty of medicine 1008, AUU Uppsala 2001, pp. 1-66). Myo-inositol has been found useful in treating panic attacks (Levine, et al, *Double-blind, placebo-controlled, crossover trial for inositol treatment for panic disorder*, Am J Psychiatry 1995; 152; 1084-1086).

One of the more prominent uses for myo-inositol has been for blood sugar regulation. Recently, D-chiro-inositol has beat proposed for insulin resistance patients (Lamer, *D-Chiro-Inositol—Its functional role in Insulin Action and its Deficit in Insulin Resistance*, International Journal of Experimental Diabetes Research 3 (2002), 47-60) on the theory that such patients have a defect in epimerization of the myo-inositol to the D-chiro-inositol and that the D-chiro inositol is the active moiety in this regard. As stated above, scyllo-inositol actually resulted in an increase in fetal defects in non-diabetic pregnancies. Phosphoinositide derangement and poor maternal metabolic turnover carries a relative risk in diabetic pregnancies for giving birth to a baby with lethal congenital anomalies like sirenomelia (Tahna, Davari et al, 2002). This defect is similar to those seen in anorectal malformation spectrum of defects.

OBJECTS OF THE INVENTION

It is therefore an object of the invention to provide a method of preventing or reducing the rate of birth defects.

It is therefore an object of the invention to use folic acid as guiding media for the invention compounds to target tumor cells with the invention compounds as described within the claims where the Folic acid receptor alpha is always expressed on a tumor. The complex will be taken into the cell membrane by endocytosis and thereby anchor itself to a glycerophosphatide. The invention will also be made with a folic acid/inositol-PEG-liposome that will target tumor cell better than a liposome by itself.

It is therefore an object of the invention to provide a method of treatment of women pre-pregnancy to prevent or reduce the chance of fetal malformations by administering D-chiro-inositol or a phosphate derivative thereof or other derivative thereof.

It is another object of the invention to provide a method of treatment of women during the first trimester of pregnancy to prevent or reduce the chance of fetal malformations by administering D-chiro-inositol or a phosphate derivative thereof or other derivative thereof.

It is another object of the invention to provide co-therapy for women pre-pregnancy with both a folate source and D-chiro-inositol or a phosphate derivative thereof or other derivative thereof.

It is another object of the invention to provide a method of treatment of women during the first trimester of pregnancy to prevent or reduce the chance of fetal malformations by co-administering D-chiro-inositol or a phosphate derivative thereof or other derivative thereof and a folate source.

It is yet another object of the invention to treat women who are taking birth control pills but who might nonetheless become pregnant by including D-chiro-inositol for a phosphate thereof or other derivative thereof) and optionally a folate source into the pills that do not contain an estrogenic substance.

It is yet another object of the invention to treat women who are taking birth control pills but who might nonetheless become pregnant by including D-chiro-inositol (or a phosphate thereof or other derivative thereof) and optionally a folate source into each of the pills in the birth control pill packet.

It is yet another object of the invention to treat women who are taking birth control pills and who may have excess estrogen insult with hyperactive/sensitive estrogen receptor (ER) positive breast tissue by including D-chiro-inositol (or a phosphate thereof or other derivative thereof) and optionally a folate source into each of the pills in the birth control pill packet.

It is another object of the invention to prevent or reduce the rate of birth defects associated with in utero fetal mis-mapping.

It is yet another object of the invention to prevent or reduce the rate of birth defects associated with improper signaling in at least one of the sonic hedgehog, smoothened, and gli pathways.

It is still another object of the invention to prevent or reduce the rate of birth defects due to a kinase disfunction in at least one of the inositol pathways.

It is another object of the invention to provide a method of preventing or reducing birth defects associated with cholesterol reduction medications.

Yet another object of the invention is the prevention or reduction of the rate of birth defects associated with fetal alcohol syndrome.

It is still another object of the invention to provide a fixed combination formulation comprising (A) at least one compound selected from (a) a folate or folic acid, (b) a hormone or steroid used in birth control, hormone replacement, and androgenablative therapy, (c) a cholesterol lowering medication, or (d) an anticancer medication, together with (B) at least one compound selected from an inositol, a phosphorylated inositol, and derivatives thereof as defined herein.

It is still another object of the invention to treat women who are on estrogenic hormone therapy and who may have estrogen-receptor (ER) and/or, ErbB receptor overexpression phenotype mediated by the (PI3K-Akt) pathway by administering as co-therapy with said estrogenic hormone therapy D-chiro-inositol (or a phosphate thereof or other derivative thereof) thereby blocking the downstream signaling elements resulting in cell cycle arrest in the G1 phase, thereby downregulating these important receptors (Breast cancer research 2004, 6: 219-224).

It is still another object of the invention to treat women who are on estrogenic hormone therapy and who may have estrogen-receptor and/or, ErbB receptor overexpression phenotype mediated by the (PI3K-Akt) pathway by administering as a single composition said estrogenic hormone therapy drug and D-chiro-inositol (or a phosphate or other derivative thereof or other derivative thereof).

It is still another object of the invention to treat women who are on anti-androgenic hormone therapy and who may have estrogen-receptor and/or, ErbB receptor overexpression phenotype mediated by the (PI3K-Akt) pathway-receptor overexpression phenotype by administering as co-therapy with said anti-androgenic hormone therapy D-chiro-inositol (or a phosphate or other derivative thereof).

It is still another object of the invention to treat women who are on anti-androgenic hormone therapy and who may have estrogen-receptor and/or, ErbB receptor overexpression phenotype mediated by the (PI3K-Akt) pathway by administering as a single composition said anti-androgenic hormone therapy drug and D-chiro-inositol (or a phosphate or other derivative thereof).

It is still another object of the invention to treat men who are on estrogenic hormone therapy and who may have estrogen-receptor and/or, ErbB receptor overexpression phenotype mediated by the (PI3K-Akt) pathway by administering as co-therapy with said estrogenic hormone therapy D-chiro-inositol (or a phosphate or other derivative thereof).

It is still another object of the invention to treat men who are on estrogenic hormone therapy and who may have estrogen-receptor and/or, ErbB receptor overexpression phenotype mediated by the (PI3K-Akt) pathway by administering as a single composition said estrogenic hormone therapy drug and D-chiro-inositol (or a phosphate or other derivative thereof).

It is still another object of the invention to treat men who are on anti-androgenic hormone therapy and who may have estrogen-receptor and/or, ErbB receptor overexpression phenotype mediated by the (PI3K-Akt) pathway by administering as co-therapy with said anti-androgenic hormone therapy D-chiro-inositol (or a phosphate or other derivative thereof).

It is still another object of the invention to treat men who are on anti-androgenic hormone therapy and who may have estrogen-receptor and/or, ErbB receptor overexpression phenotype mediated by the (PI3K-Akt) pathway by administering as a single composition said anti-androgenic hormone therapy drug and D-chiro-inositol (or a phosphate or other derivative thereof).

It is still a further object of the invention to reduce or prevent fetal malformation occurrence where the fetal malformation is a neural tube defect, a cranio-facial defect, an anorectal malformation spectrum, caudal regression syndrome, neuralectoderm derived pediatric tumors, etc.

It is still another object of the invention to provide a method of modulating the phosphatidylinositol/PI3K signaling pathway with compounds and/or therapy of the present invention.

A still further object of the present invention is to provide a method of modulating the sonic hedgehog, the receptors patched and smoothened, and GL1,2,3 transcription family pathway with compounds and/or therapy of the present invention.

Another object of the invention is to provide a method of prevention or amelioration or treatment of a phosphatidylinositol/PI3K signaling pathway signaling defect with the compounds and/or therapies of the present invention.

Thus, it is an object of the invention to correct the inherent mechanism of stem cell autoregulation.

Another object of the invention is to increase the efficacy of standard chemotherapeutic agents.

Yet another object of the invention is to provide a method of prevention or amelioration or treatment of a defect in the signaling pathway associated with sonic hedgehog, the receptors patched and/or smoothened, and/or GL1,2,3 transcription family signaling pathway with the compounds and therapies of the present invention.

Yet another object of the invention is to provide a method or treatment for anti-angiogenic activity to reduce tumor incidence and/or tumor load.

Still another object of the invention is to induce antiangiogenesis in localized or distant metastasized tumors.

Yet another object of the invention is to decrease the risk of deep vein thrombosis (DVT's) while using chemotherapeutic agents, however administered, including oral, parenteral, or transdermal, birth control pills or hormonal products.

Yet another object of the invention is to provide a method or treatment for antiangoigenic activity to reduce Deep Vein Thrombosis (DVT's), pulmonary emboli (PE's) etc, utilizing the therapies and/or compounds of the present invention whether administered parenterally, orally, transdermally or other suitable administration mode.

Yet another object of the invention is to provide a method or treatment for increasing the chemotherapeutic efficacy by synergistic action of the current isomer (or phosphate or other derivative or of two or more of the isomer, a phosphate thereof or other derivative thereof) with standard chemotherapeutic agents in cancer treatments, especially breast, prostate, blood, colon, lung, liver, pancreatic, cervix, skin, and soft tissue cancers.

Still another object of the invention is to reduce the potential hazardous risk of tamoxifen-associated cardiovascular disease.

Yet another object of the invention is to reduce the numbers and size of tumors locally or distant especially in breast cancers, but also cancers originating from blood, colon, lung, liver, cervix, prostate, skin, and soft tissue.

Still another object of the invention is manipulating cell growth for the regeneration of neural, hepatic, pancreatic, intestinal, spleenic, and/or cardiac tissue.

Still another object of the invention is the treatment of tissue necrosis factor related conditions.

Yet another object of the invention is the treatment of conditions associated with abnormal kinase activity.

Yet another object of the invention is to protect estrogen sensitive tissue from excess estrogen insult, whether such excess insult is due to absolute estrogen excess or relative estrogen excess with respect to normal estrogen/androgen balance, whether endogenous or exogenously derived.

A further object of the invention is the prevention of or reduction in the amount or rate of emergence of resistance of tumorigenic cells to anticancer agents.

A still further object of the invention is the administration of the compound of the invention, with or without additional therapeutic agents in a polymer matrix or bound to a polymer as a depot or implant.

An even further object of the invention is to inhibit cell growth in the treatment of psoriasis, actinic keratosis, acne, dermatitis, conditions of inappropriate or excess hair growth, and/or cosmetic purposes.

Another object of the invention is to provide methods and compositions for obtaining at least one of Shh loss-of-function or patched or smoothened gain-of-function by administration of at least one inositol isomer (other than D-chiroinositol or myo-inositol), phosphorylate, or derivative thereof. Still further objects of the invention will be apparent to those of ordinary skill.

It is therefore an object of the invention to provide novel compounds that are inhibitors of PI3k-Akt signaling pathway.

It is also an object of the present invention to provide pharmaceutical compositions that comprise the novel compounds that are specific inhibitors of Akt/PKB.

It is also an object of the present invention to provide a method for treating cancer that comprises administering such inhibitors of Akt/PKB activity.

It is therefore an object of the invention to provide novel compounds that are inhibitors of overactive proinflammatory cytokines.

It is also an object of the present invention to provide a method for treating hepatitis serous A,B,C,D that comprises administering such inhibitors of Tumor Necrosis Factor.

It is also an object of the invention to improve the response to alpha interferon therapy by combining the invention compound with interferon.

It is another object of the invention to alleviate anemia due to enlarged spleen problems associated with chronic active hepatitis.

Yet it is another object of the invention to inhibit overexpression of SOC3 and SHP2.

It is another object of the invention to upregulate p27kip1 to overcome Herceptin resistance.

It is another object of the invention to upregulate P21cip for cell cycle arrest in cancer and inflammation.

Yet it is another object of the invention to down regulate or inhibit Ap-1, thus inhibiting AP-1 transcription factor causes blockade of multiple signal transduction pathways and inhibits cancer growth.

It is another object of the invention to inhibit or downregulate ppRb thereby inhibiting tumor survival factor.

It is a still further object of the invention to provide methods, compositions, and kits that utilize activators of pyruvate kinase M2 (PKM2) for the treatment, prevention, or amelioration of a disorder or disease related to PKM2 function.

SUMMARY OF THE INVENTION

These and other objects of the invention can be achieved via the administration, to an appropriate patient, of a compound which is a member of the family of D-chiroinositol, phosphorylates, and other derivatives thereof. In some uses, the objects can also be achieved with a broader array of inositol based compounds, their phosphorylates, and other derivatives thereof.

The foregoing fetal malformation prevention objects and others are achieved by treating women of child bearing years with D-chiro-inositol (and/or a phosphate or other derivative thereof) and optionally a folate source, optimally from pre-conception through at least the first trimester of pregnancy. Inclusion of the D-chiro-inositol along with birth control pills has the added benefit that stores of D-chiro-inositol (and/or phosphates and/or other derivatives thereof)

and folate are high in women taking birth control pills even before they discontinue such treatment or become pregnant notwithstanding being on such therapy. A further benefit of such inclusion is that D-chiro-inositol (or a phosphate or other derivative thereof) also downregulates, modulates, or antagonizes estrogen-receptor and/or, ErbB receptor overexpression phenotypes in breast tissue.

The breast cancer avoidance objects of the invention are achieved by administering D-chiro-inositol (with or without folate) to patients who are known to have or are suspect of having estrogen-receptor and/or, ErbB receptor overexpression phenotypes that is sensitive to estrogenic substance exposure or to anti-androgenic therapy (which may ultimately result in estrogenic excess). The breast cancer avoidance (prevention) objects of the invention can be achieved in both men and women. While the benefits may be greater with the folate in many of the foregoing, the benefits can also be achieved even in the absence of the folate component in many of the present invention objects, and unless specifically excluded, or required by the context to be excluded, the folate free methods and treatments are included within the scope of the invention. Other objects of the invention with respect to Shh loss-of-function and/or smoothened or patched gain-of-function and the sequelae thereof are also achieved by administration of an inositol isomer other than D-chiroinositol and myo-inositol, phosphorylates, pyrophosphorylates, and other derivatives thereof and such non-D-chiroinositol non-myoinositol based compounds are also part of the invention.

One aspect of the present invention makes available methods and compositions for inhibiting certain receptors in cell pathway activation. In certain embodiments, the subject methods can be used to counteract the phenotypic effects of unwanted activation of the pathway. For example, the subject method can involve contacting a cell (in vitro or in vivo) with the compositions (defined infra), such as a D-chiroinositol or a phosphate or other derivative thereof in an amount sufficient to antagonize a dependent defective pathway activation.

The invention objects involving modulating receptor-dependent pathway activation can be achieved by, for example, contacting a cell (in vitro or in vivo) with an agonist (defined infra) in an amount sufficient to activate a dependent pathway activation pathway.

In general the above-mentioned inositols are selected from D-chiroinositol, their phosphorylates, and other derivatives of either as described further herein. For some of the embodiments, the inositol compound may also be a different isomer of inositol, its phosphorylates and derivatives of either. These compounds (based on the D-chiroinositol structure) are described more fully in co-pending U.S. patent application Ser. No. 11/591,398, filed Nov. 1, 2006 and U.S. Ser. No. 12/001,869, filed Dec. 13, 2007. Those compounds, as well as their corresponding analogs that differ by being based on myo-inositol or other inositol isomer rather than being based on D-chiroinositol, (whether or not further detailed herein are incorporated herein by reference) may be chosen as the inositol component in addition to any of the inositol component compounds specifically set forth herein. The optional folate component is also detailed in these two co-pending applications and that disclosure is also incorporated herein by reference as the optional folate component in addition to any specific disclosure set forth herein.

The subject compounds may be formulated as a pharmaceutical preparation comprising a pharmaceutically acceptable excipient. Antagonists of the invention and/or preparations comprising them may be administered to a patient to treat conditions involving unwanted cell proliferation, e.g., cancer and/or tumors (such as, without limitation, medulloblastoma, rhabdomyosarcomas, adenocarcinomas, basal cell carcinoma, etc, non-malignant hyperproliferative disorders, etc). Receptor agonists such its those for smoothened or G-protein coupled receptors can also be used to regulate the growth and differentiation of normal tissues. In certain embodiments, such compounds or preparations are administered systemically and/or locally, e.g., topically, transdermally, or as an injected depot or an implant in and/or around tumor site after excision or incisional biopsies.

In a further aspect, the invention features a method of increasing the level of PKM2 activity and/or glycolysis (e.g., inhibiting the endogenous ability of a cell in the patient to down regulate PKM2) in a patient in need thereof. The method comprises the step of administering an effective amount of an activator, preferably a selective activator, of PKM2 to the patient in need thereof, thereby increasing the level of PKM2 activity and/or glycolysis in the patient. PKM2 is only expressed in growing cells such as cancer cells or fat cells in the patient; other tissues use other isoforms of PK. In embodiments of the invention, an activator is used to maintain PKM2 in its active conformation or constitutively activate pyruvate kinase activity in proliferating cells as a means to divert glucose metabolites into catabolic rather than anabolic processes in the patient.

In another aspect, the invention features a method of regulating cell proliferation in a patient in need thereof. The method comprises the step of administering an effective amount of an activator, preferably a selective activator, of PKM2 to the patient in need thereof, thereby regulating cell proliferation in the patient. This method can inhibit growth of a transformed cell, e.g., a cancer cell, or generally inhibit growth in a PKM2-dependent cell that undergoes aerobic glycolysis.

In another aspect, the invention features a method of treating a patient suffering from or susceptible to a disease or disorder associated with the function of PKM2. The method comprises the step of administering an effective amount of an activator, preferably a selective activator, of PKM2 to the patient in need thereof, thereby treating, preventing, or ameliorating the disease or disorder in the patient. In another embodiment, the activator is provided in a pharmaceutical composition.

In another embodiment, the method includes identifying or selecting a patient who would benefit from activation of PKM2. The patient can be identified on the basis of the level of PKM2 activity in a cell of the patient (e.g., as opposed to merely being in need of treatment of the disorder (e.g., cancer)). In another embodiment, the selected patient is a patient suffering from or susceptible to a disorder or disease identified herein, e.g., a disorder characterized by unwanted cell growth or proliferation, e.g., cancer, obesity, diabetes, atherosclerosis, restenosis, and autoimmune diseases.

In another embodiment, the activator of PKM2 utilized in the methods and compositions of this invention operates by or has one or more of the following mechanisms or properties: the activator is an allosteric activator of PKM2; the activator stabilizes the binding of an inositol phosphate, derivative or analog thereof in a binding pocket of PKM2; the activator inhibits the release of sugars from a binding pocket of PKM2; the activator is an agonist, e.g., an analog, of a sugar and or phosphate e.g., an agonist which hinds PKM2 with a lower, about the same, or higher affinity than does FBP; the activator inhibits the dissolution of tetrameric PKM2; the activator promotes the assembly of tetrameric PKM2; the activator stabilizes the tetrameric conformation of PKM2; the activator inhibits the binding of a phosphotyrosine containing polypeptide to PKM2; the activator inhibits the ability of a phosphotyrosine containing polypeptide to induce the release of a sugar phosphate from PKM2, e.g., by inducing a change in the conformation of PKM2, e.g., in the position of Lys433, thereby hindering the release of a native sugar of the binding pocket of PKM2; the activator binds to or changes the position of Lys433 relative to binding pocket; the activator selectively activates PKM2 over at least one other isoform of PK, e.g., the activator is selective for PKM2 over one or mom of PKR, PKM1, or PKL; the activator has an affinity for PKM2 which is greater than its affinity for at least one other isoform of PK, e.g., PKR, PKM1, or PKL; the activator has an EC.sub.50 of from about 100 micromolar to about 0.1 nanomolar, e.g., about 10 micromolar to about 0.1 nanomolar, about 1 micromolar to about 0.1 nanomolar, about 500 nanomolar to about 0.1 nanomolar, about 250 nanomolar to about 0.1 nanomolar, about 100 nanomolar to about 0.1 nanomolar, about 50 nanomolar to about 0.1 nanomolar, about 25 nanomolar to about 0.1 nanomolar, about 10 nanomolar to about 0.1 nanomolar, about 100 nanomolar to about 1 nanomolar, about 50 nanomolar to about 1 nanomolar, about 25 nanomolar to about 1 nanomolar, about 10 nanomolar to about 1 nanomolar; and/or the activator is provided at a dosage of 0.1 mg to about 3000 mg per day, e.g., about 1 mg to about 2400, about 15 mg to about 2400, about 15 mg to about 1500, about 75 mg to about 1200, or about 75 mg to about 600 mg per day.

In another embodiment, the activator is administered at a dosage and frequency sufficient to increase lactate production or oxidative phosphorylation.

The method may further include the step of co-administering to the patient in need thereof an additional therapeutic agent. The term "co-administering" as used herein means that an additional therapeutic agent may be administered together with an activator of this invention as part of a single dosage form or as separate, multiple dosage forms. Alternatively, the additional agent may be administered prior to, consecutively with, or following the administration of a PKM2 activator. In such combination therapy treatment, both the PKM2 activator and the additional therapeutic agent(s) are administered by conventional methods. The administration of a composition of this invention, comprising both a PKM2 activator and an additional therapeutic agent, to a patient does not preclude the separate administration of that same therapeutic agent, any other second therapeutic agent, or the same or different PKM2 activator to the patient at another time during a course of treatment.

When the treatment is for cancer, the additional therapeutic agent may be a chemotherapeutic agent. When the treatment is for an autoimmune disorder, the additional therapeutic agent may be an immune modulatory agent. When the treatment is for obesity, the additional therapeutic agent may be a metabolic modulator like an another inositol analog. When the treatment is for diabetes, the additional therapeutic agent can be an anti-diabetes drug, e.g., an oral anti-diabetes drug, e.g., metformin, insulin, or an insulin analog or derivative. The choice of an additional therapeutic agent will be based upon the disease or condition that the patient is suffering from or susceptible to, as well as the judgment of the treating physician In another embodiment, the patient is treated with a PKM2 activator without co-administration of a hypoxic cell sensitizer, e.g., tirapazamine.

In another embodiment, the patient is being treated for cancer is characterized by one or more of the following: cells in the cancer carry out aerobic glycolysis; the cancer tissue has increased glucose uptake, as compared to a control value for glucose uptake, e.g., as measured by 2-deoxyglucose uptake or uptake by a labeled glucose or glucose analog; the cancer is metastatic; the cancer is PET positive; or the cancer has increased PKM2 expression.

In another embodiment, the activator is administered at least twice. In still another embodiment, the activator is administered in sufficient amount and with sufficient frequency that therapeutic levels are maintained for at least 1, 3,5, 7, 10, 20, 30, 60, or 180 days. In another embodiment, the treatment is pulsatile or repeated and each administration provides therapeutic levels that are maintained for at least 1, 3, 5, 7, 10, or 20 days.

In some specific embodiments, the additional therapeutic agent is an inhibitor of glutamine metabolism.

In some specific embodiments the additional therapeutic agent is an inhibitor(s) of receptor tyrosine kinase (RTK/PI3K/AKT/mTOR),C-myc-hnRNPs/PKM2 network.

BRIEF DESCRIPTION OF THE DRAWING

Not Applicable

DETAILED DESCRIPTION OF THE INVENTION

1. General
A. Definitions
1. Biological and Medicinal Terms

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Burn wounds" refer to cases where large surface areas of skin have been removed or lost from an individual due to heat and/or chemical agents.

The term "carcinoma" refers to a malignant new growth made up of epithelial cells tending to infiltrate surrounding tissues and to give rise to metastases. Exemplary carcinomas include: "basal cell carcinoma", which, is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "cerium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug which produces 50% of its maximum response or effect.

An "effective amount" of, e.g., a receptor antagonist, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells, squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and non-vascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly, prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

The term "hedgehog antagonist" refers to an agent which potentiates or recapitulates the bioactivity of patched, such as to repress transcription of target genes. Preferred hedgehog antagonists can be used to overcome a ptc loss-of-function and/or a smoothened gain-of-function, the latter also being referred to as smoothened antagonists. The term hedgehog antagonist as used herein refers not only to any agent that may act by directly inhibiting the normal function of the hedgehog protein, but also to any agent that inhibits the hedgehog signaling pathway, and thus recapitulates the function of ptc.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term hedgehog gain-of-function is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug which is lethal in 50% of test subjects.

The term "nail" refers to the horny cutaneous plate on the dorsal surface of the distal end of a finger or toe.

The term "patched loss-of-function" refers to an aberrant modification or mutation of a ptc gene, or a decreased level of expression of the gene, which results in a phenotype which resembles contacting a cell with a hedgehog protein, e.g., aberrant activation of a hedgehog pathway. The loss-of-function may include a loss of the ability of the ptc gene product to regulate the level of expression of Ci genes, e.g., Gli1, Gli2 and Gli3. The term 'ptc loss-of-function' is also used herein to refer to any similar cellular phenotype (e.g., exhibiting excess proliferation) which occurs due to an alteration anywhere in the hedgehog signal transduction pathway, including, but not limited to, a modification or mutation of ptc itself. For example, a tumor cell with an abnormally high proliferation rate due to activation of the hedgehog signaling pathway would have a 'ptc loss-of-function' phenotype, even if ptc is not mutated in that cell.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "smoothened gain-of-function" refers to an aberrant modification or mutation of a smo gene, or an increased level of expression of the gene, which results in a phenotype which resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) Nature 384: 177-179). The gene smo is a segment-polarity gene required for the correct patterning of every segment in *Drosophila* (Alcedo et al., (1996) Cell 86: 221-232). Human homologs of smo have been identified. See, for example, Stone et al. (1996) Nature 384:129-134, and GenBank accession U84401. The smoothened gene encodes an integral membrane protein with characteristics of heterotrimeric G-protein-coupled receptors; i.e., 7-transmembrane regions. This protein shows homology to the *Drosophila* Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) Nature 384: 119-120). Rather, the binding of Sonic hedgehog (SHH) to its receptor, PTCH, is thought to prevent normal inhibition by PTCH of smoothened (SMO), a seven-span transmembrane protein. Recently, it has been reported that activating smoothened mutations occur in sporadic basal cell carcinoma, Xie et al. (1998) Nature 391:90-2, and primitive neuroectodermal tumors of the central nervous system. Reifenberger et al. (1998) Cancer Res 58: 1798-803.

The term "therapeutic index" refers to the therapeutic index of a drug defined as $LD_{50}/ED_{50}$.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

2. Chemical Terms

By "activator" is meant an agent that increases the level of activity of PKM2 from the state of inactive monomeric or dimeric form or maintains or increases the activity of active tetrameric form of PKM2 (e.g., in the presence of an endogenous inhibitor). Increasing activity can include reducing endogenous down-regulation of PKM2 by an endogenous inhibitor (e.g., an endogenous phosphotyrosine peptide or protein). The binding of phosphotyrosine-containing peptide with activated PKM2 results in dissociation of FBP and inactivation of PKM2. Autonomous growth signaling in proliferating cells or stimulation of fat cells by insulin leads to tyrosine phosphorylation cascades. An activator can exert its effect in a number of ways including one or more of the following; an activator can render PKM2 resistant to inhibition by an inhibitor, e.g., an endogenous inhibitor; an activator inhibits release of an activator, more specifically FBP or any inositol derivative or phosphate; an activator can bind to PKM2 and prevent an endogenous inhibitor from promoting the release of an endogenous activator, more specifically FBP; or an activator can inhibit the dissolution or promote the reassembly of the subunit which make up PKM2, e.g., an activator can inhibit oxidation of sulfhydryl moieties on such subunits, e.g., inhibit the oxidation of cysteine residues.

An activator can cause PKM2 activity to increase to a level that is greater than PKM2's levels (e.g., basal levels) of activity (e.g., levels seen in the absence of an endogenous or natural activator/ligand, e.g., FBP or any inositol sugar). For example, the activator may mimic the effect caused by an endogenous or natural ligand or activator (e.g., FBP or any inositol sugar). The activating effect caused by the agent may be to the same, to a greater, or to a lesser extent than the activating effect caused by an endogenous or natural ligand or activator, but the same type of effect can be caused. Peptides, nucleic acids, find small molecules may be activators. In preferred embodiments, the activator has a molecular weight in the range of 100 or 200 to 10,000, 100 or 200 to 5,000, 100 or 200 to 2,000, or more preferably 100 to 300, 200 to 500, 150 to 500, 200 to 500, 300 to 500, or 150 to 800 Daltons.

Direct activators are activators which interact directly (e.g., bind) by forming a non-covalent bond such as a hydrogen, ionic, electrostatic, or hydrophobic bond, or induce a change in conformation in PKM2, including the tetrameric PKM2 molecule or the monomeric and dimeric molecules, or another activator thereof. In preferred embodiments, the direct activator forms a non-covalent bond with a specific moiety on the PKM2 or endogenous activator (e.g., FBP, inositol sugar/phosphate/inositol analog thereof). Direct activators are preferred.

An expressional activator increases the expression of the PKM2 isoform at the nucleic acid level. This includes activators winch induce the expression of PKM2 at the DNA level (e.g., by acting as a co-factor to induce transcription of PKM2) or the RNA level.

An agent can be evaluated to determine if it is an activator by measuring either directly or indirectly the activity of the PKM2 when subjected to the agent. The activity of the agent can be measured, for example, against a control substance. In some instances, direct activation of PKM2 is measured. The activity of PKM2 can be measured, for example, by monitoring the concentration of a substrate or a product directly or indirectly.

By "administering" is meant a method of giving a dosage of a pharmaceutical composition to a patient. The compositions described herein can be administered by a route selected from, e.g., ocular, inhalation, parenteral, dermal, transdermal, buccal, rectal, vaginal, sublingual, perilingual, nasal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

An "aliphatic group" includes straight chain or branched chain, or cyclic hydrocarbons (other than aromatic groups), the aliphatic group having up to 30 carbon atoms (preferably up to 20 carbon atoms, more preferably up to 10 carbon atoms, even more preferably up to 7 carbon atoms, most preferably up to 5 carbon atoms, especially methyl, ethyl, propyl, and butyl for straight chain saturated variants) and the corresponding branched analogs and the unsaturated analogs of each and 3-10 carbon atoms in the corresponding cyclic aliphatic rings (cycloaliphatic), more preferably 5, 6, or 7 ring members, Each aliphatic group may be unsubstituted or substituted with one or more substituents as detailed below. Furthermore, each of the above groups can be interrupted by one or more heteroatoms selected from nitrogen, sulfur, oxygen, and phosphorous, excepting peroxy (—O—O—). The cycloaliphatic rings may have two, three, or four rings fused together, each ring independently having definitions in accordance with this paragraph. Each aliphatic group and cycloaliphatic ring may be independently unsubstituted or substituted in accordance with the definitions below, however, if a definition results in a continuous loop, only three loop circuits at most are permitted.

An "aromatic group" or "aryl group" as used herein includes (unless specifically excluded or the context requires exclusion) heteroaryls, and each ring of which has 6 to 8 ring members per aromatic ring and may be fused to aromatic or aliphatic rings, each of which is unsubstituted or substituted with one of more substituents as set forth more fully below. Heteroaryls correspond to carbocyclic aryls except that they have one or more ring members selected from nitrogen, oxygen, or sulfur. Each aromatic group may be independently unsubstituted or substituted in accordance with the definitions below, however, if a definition results in a continuous loop, only three loop circuits at most are permitted.

Substituents for the above aliphatic and aromatic groups may include, without limitation, those from the following group (A): halogen (preferably fluorine, chlorine, bromine, or iodine, more preferably fluorine or chlorine), hydroxyl, trihalomethyl (especially trifluoromethyl), cyano, carbonyl, derivatized carbonyl (such as carboxylic acid, alkoxycarbonyl, (optionally N-substituted with alkyl or acyl)aminocarbonyl, formyl), $C_{2-7}$acyl, $C_{2-7}$acyloxy, thiocarbonyl, analogous derivitized forms thereof to the derivatized carbonyl in which the doubly bound oxygen is replaced by sulfur, the corresponding —C(S)SH group and their derivatized counterparts, phosphoryl, phosphate, phosphonate, phosphinate, amido, amidine, imine, cyano, nitro, azido, sulfhydryl, alkyl thio, sulfate, sulfonate, sulfamoyl, sulfonamide, sulfonyl, heterocyclyl (aka heterocycloaliphatic), aralkyl, aromatic group, or heteroaromatic group, each of which can be substituted further not front the above substituent list, but from one or more substituents selected from the following group (B) consisting of amino, azido, imino, amido, phosphoryl (including phosphonate and phosphinate), sulfonyl (including sulfate, sulfonamide, sulfamoyl, and sulfonate), ether, alkylthio, carbonyl (including ketone, aldehyde, carboxylate, and ester), trihalomethyl (especially trifluoromethyl), cyano, alkoxy, hydroxy, and the like, and each of these further group (B) substituents may be still further substituted with groups selected from group (B). In any case where the above substituent requires a group 10 be specified that is not so specified above or below (for example an amino, an ether, an ester, etc. where the remainder of the group cannot be determined from the above or below), the preferred group is, without being limited thereto, an alkyl of up to 7 carbon atoms or if results in a cyclical unending definitional loop, such loop terminates after no more than three cycles thereof in either a hydrogen or alkyl of up to 7 carbon atoms). These substituents may also be a replacement for one or more of the hydrogen atoms on the inositol ring hydroxy groups or a hydroxyl group indicated within the substituents set forth in this definition (provided that no peroxy groups result) and/or one or more of the hydrogen atoms that are on the inositol ring directly and/or or a hydroxyl group indicated within the substituents set forth in this substituent definition provided that if an unending loop results, such loop terminates after no more than three cycles thereof in either a hydrogen or alkyl of up to 7 carbon atoms.

In addition to the general definition above, the term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—Ra, wherein m is 0-8, preferably 0-4 and $R_a$ is aryl, cycloalkyl, cycloalkenyl, heterocyclyl, or polycyclyl. Representative alkylthio groups include methylthio, ethylthio, and the like.

In addition to the general definition above, the terms "amine" and "amino" are art-recognized and refer to both unsubstituted and substituted amines, e.g., a moiety that can be represented by the general formula:

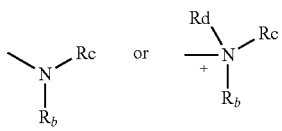

wherein $R_b$, $R_c$ and $R_d$ each independently represent a hydrogen, an alkyl, an alkenyl, —$(CH_2)_m$—$R_a$, carbonyl or $R_b$ and $R_c$ taken together with the N atom to which they are attached complete a heterocycle having from 4 to 8 atoms in the ring structure; $R_a$ represents an aryl, a cycloalkyl, a cycloalkenyl, a heterocycle or a polycycle; and m is zero or an integer in the range of 1 to 8. In preferred embodiments, only one of $R_b$, $R_c$ and $R_d$ can be a carbonyl, e.g., they and the nitrogen together do not form an imide. In even more preferred embodiments, each independently represent a hydrogen, an alkyl, an alkenyl, or —$(CH_2)_m$—$R_a$. Thus, the term "alkylamine" as used herein means an amine group, as defined above, having a substituted or unsubstituted alkyl attached thereto, i.e., at least one of $R_b$ and $R_c$ is an alkyl group.

The term "amido" is art-recognized as an amino-substituted carbonyl and includes a moiety that can be represented by the general formula:

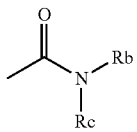

$R_b$ and $R_c$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazoic, pyrazole, pyridine, pyrazine, pyridazine and pyrimidine, and the like. Those aryl groups having heteroatoms in the ring structure may also be referred to as "aryl heterocycles" or "heteroaryls" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

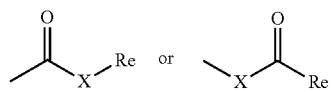

wherein X is a bond or represents an oxygen or a sulfur, and $R_c$ represents a hydrogen, an alkyl, an alkenyl, —$(X_a)_n$—$(CH_2)_m$—$R_a$ or a pharmaceutically acceptable salt, where X, m and $R_a$ are as defined above $X_a$ is a bond or represents an oxygen or a sulfur, and n is 0 or 1, but required to be 0 when $R_c$ is bound to an oxygen. When X is oxygen and $R_c$ is —$(X_a)_n$—$(CH_2)_m$—$R_a$ and $X_a$ is also oxygen, the substituent is a carbonate. Where X is oxygen and $R_c$ is not hydrogen, the formula represents an "ester". Where X is oxygen, and $R_c$, is as defined above, the moiety is referred to herein as a carboxyl group, and particularly when $R_c$ is a hydrogen, the formula represents a "carboxylic acid" or a formate respectively. In general, where the oxygen atom of the above formula is replaced by sulfur, the formula represents a "thiocarbonyl" group. On the other hand, where X and $X_a$ are each a bond, and $R_c$, is not hydrogen, the above formula represents a "ketone" group. Where X is a bond, and $R_c$ is hydrogen, the above formula represents an "aldehyde" group.

By "chemotherapeutic agent" is meant a chemical that may be used to destroy a cancer cell, or to slow, arrest, or reverse the growth of a cancer cell. Chemotherapeutic agents include, e.g., L-asparaginase, bleomycin, busulfan carmustine (BCNU), chlorambucil, cladribine (2-CdA), CPT11 (irinotecan), cyclophosphamide, cytarabine (Ara-C), dacarbazine, daunorubicin, dexamethasone, doxorubicin (adriamycin), etoposide, fludarabine, 5-fluorouracil (5FU), hydroxyurea, idarubicin, ifosfamide, interferon-.alpha. (native or recombinant), levamisole, lomustine (CCNU), mechlorethamine (nitrogen mustard), melphalan, mercaptopurine, methotrexate, mitomycin, mitoxantrone, paclitaxel, pentostatin, prednisone, procarbazine, tamoxifen, taxol-related compounds, 6-thiogaunine, topotecan, vinblastine, vincristine, cisplatinum, carboplatinum, oxaliplatinum, or pemetrexed. In another embodiment, the chemotherapeutic agent is not an anti-hypoxic agent.

By "effective amount" is meant the amount of a pharmaceutical composition of the invention required to treat a patient suffering from or susceptible to a disease, such as, e.g., cancer, diabetes, obesity, autoimmune diseases, atherosclerosis, restenosis, and proliferation-dependent diseases.

The effective amount of a pharmaceutical composition of the invention used for treatment varies depending upon the manner of administration and the age, body weight, and general health of the subject. Ultimately, the attending prescribe will decide the appropriate amount and dosage regimen. Such an amount is referred to as the "effective amount."

The term "heteroatom" as used herein means an atom of any element other than carbon or hydrogen. Preferred heteroatoms are nitrogen, oxygen, phosphorus, sulfur, and selenium, more preferably nitrogen, oxygen, phosphorus, and sulfur; most preferably nitrogen, oxygen, and sulfur.

The terms "heterocyclyl" or "heterocyclic group", notwithstanding and without limitation to prior definitions of these terms herein, refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

Also (or purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted. Preferably hydrocarbons contain only hydrogen and carbon unless modified to indicate some other type of atom is present.

By "immunomodulatory agent" is meant an agent that can elicit or suppress an immune response. Examples of immunomodulatory agents include, e.g., non-steroidal immunophilin dependent immunosuppressants, e.g., cyclosporine (e.g., Restasis), and steroids, e.g., dexamethasone, rimexolone, fluorometholone, medrysone, and loteprednol etabonate.

By "inhibitor" is meant an agent that measurably slows, stops, decreases, or inactivates the enzymatic activity of PKM2 to a level that is less than the PKM2's basal level of activity. Inhibitors of PKM2 may be small molecules, peptides, or nucleic acids. Decreasing activity can include preventing endogenous up-modulation of PKM2 by an endogenous activator (e.g., an inhibitor can render PKM2 resistant to activation by an activator, e.g., a naturally occurring activator and can, e.g., promote release of an activator, e.g., FBP). In another embodiment, an activator can promote dissolution or inhibit reassembly of the subunits which make up PKM2. In preferred embodiments, the activator has a molecular weight in the range of 100 or 200 to 10,000, 100 or 200 to 5,000, 100 or 200 to 2,000, or more preferably 100 to 300, 200 to 500, 150 to 500, 200 to 500, 300 to 500, or 150 to 800 Daltons.

Direct inhibitors are inhibitors which interact directly (e.g., bind) by, e.g., forming a non-covalent bond such as a hydrogen, ionic, electrostatic, hydrophobic or bond, or induce a change in conformation in PKM2 or a subunit or activator thereof. In preferred embodiments, the direct inhibitor forms a non-covalent bond with a specific moiety on the PKM2 or endogenous activator (e.g., FBP). Direct inhibitors are preferred such as any and all inositol phosphates and novel phosphates incorporated. A direct inhibitor can be one that exerts its effect at the protein level, or one that exerts its effect at the nucleic acid level. An example of the former is a compound that interacts with one or both of PKM2 and FBP to promote release of FBP from PKM2. An example of the latter is a nucleic acid-based drug, e.g., an siRNA or an antisense molecule, which targets a subunit of a PKM2.

An agent can be evaluated to determine if it is an inhibitor by measuring either directly or indirectly the activity of PKM2 when subjected to the agent. The activity of the agent can be measured, for example, against a control substance. In some instances, the activity measured of the agent is for inhibition of PKM2. The activity of PKM2 can be measured, for example, by monitoring the concentration of a substrate such as lactate or NADH.

As used herein, the terms "inhibit" or "prevent" include both complete and partial inhibition or prevention. An inhibitor may completely or partially inhibit. As used herein, the term "activate" can refer to different levels of activation.

The term "lower" in connection with an aliphatic group means up to 7 carbons, preferably up to 5 carbons, more preferably up to 4 carbons.

By "modulator" is meant an agent that modulates (e.g., activates or inhibits) the activity of pyruvate kinase (e.g., PKM2). For example, the modulator may be, e.g., a peptide that inhibits the activity of pyruvate kinase. Alternatively, a modulator may be, e.g., a nucleic acid (e.g., siRNA) or small molecule. Modulators may be useful in the treatment of, e.g., cancer, diabetes, obesity, autoimmune diseases, neurological diseases (e.g., Parkinson's disease and Alzheimer's disease), proliferation-dependent diseases, and other diseases associated with the function of pyruvate kinase.

By "patient" is meant any animal, e.g., mammal (e.g., a human).

By "pharmaceutical composition" is meant any composition that contains at least one therapeutically or biologically active agent and is suitable for administration to a patient. For the purposes of this invention, pharmaceutical compositions suitable for delivering a therapeutic can include, e.g., eye drops, tablets, gel caps, capsules, pills, powders, granulates, suspensions, emulsions, solutions, gels, hydrogels, oral gels, pastes, ointments, creams, plasters, drenches, delivery devices, suppositories, enemas, injectables, implants, sprays, or aerosols. Any of these formulations can be prepared by well-known and accepted methods of art. See, for example, Remington: The Science and Practice of Pharmacy (2I.sup.st ed.), ed. A. R, Gennaro, Lippincott Williams & Wilkins, 2005, and Encyclopedia of Pharmaceutical Technology, ed. J. Swarbrick, Informa Healthcare, 2006, each of which is hereby incorporated by reference.

Agents useful in the pharmaceutical compositions of the invention may include those described herein in any of their pharmaceutically acceptable forms, including isomers such as diastereomers and enantiomers, salts, solvates, prodrugs, and polymorphs, thereof, as well as racemic mixtures of the agents described herein. Which includes all inositol isomers, diastereomers, enantiomers.

A "phosphonamidite" can be represented in the general formula:

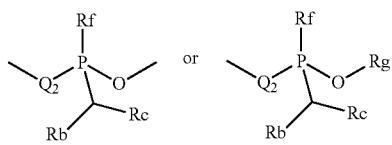

wherein $R_b$ and $R_c$ are as defined above, $Q_2$ represents O, S or N, $R_f$ represents a lower alkyl or an aryl, and $R_g$ represents H, lower alkyl, or aryl.

A "phosphoramidite" corresponds to the above phosphonoamidite except that $R_f$ is replaced by =O:

A "phosphoryl" can in general be represented by the formula:

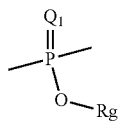

wherein $Q_1$ is O or S and $R_g$ is hydrogen, a lower alkyl, or an acyl.

By "prodrug" is meant a molecule that, upon metabolism in the body of a subject, is chemically converted to another molecule serving a therapeutic or other pharmaceutical purpose (e.g., a drug molecule containing a carboxylic acid contains an amide or an ester bond in its prodrug form, which is cleaved upon metabolism).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M Protective Groups in Organic Synthesis, $2^{nd}$ ed.; Wiley: New York, 1991).

By "selective" is meant at least 20%, 50%, 75%, 2-fold, 3-fold, 4-fold, 5-fold, 6-fold, or 10-fold greater inhibition of a PKM2 over a second kinase, e.g., a second pyruvate kinase, e.g., a different isoform. Thus, in some embodiments, the agent is selective for PKM2 over another isoform. For example, an agent is selective for PKM2 relative to PKM1. Selective regulation, e.g., inhibition or activation, or selective modulation, are used interchangeably with specific regulation or specific modulation.

By "substantially identical" is meant a polypeptide or peptide exhibiting at least 60%, 65%, 70%, 75%, 80%, 85%, 90%, 95%, 98%, 99%, or even 100% identity to a reference amino acid or nucleic acid sequence over contiguous residues. Sequence identity is typically measured using a sequence analysis program (e.g., BLAST 2; Tatusova et al., FEMS Microbiol Lett. 174:247-250, 1999) with the default parameters specified therein. Conservative substitutions typically include substitutions within the following groups: glycine, alanine, valine, isoleucine, leucine; aspartic acid, glutamic acid, asparagine, glutamine; serine, threonine; lysine, arginine; and phenylalanine and tyrosine.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described heroin which satisfy the valences of the heteroatoms. This invention is not intended to be limited in any manner by the permissible substituents of organic compounds.

It will be understood that "substitution" or "substituted with" includes the implicit provision that such substitution is in accordance with permitted valence of the substituted atom and the substituent, and that the substitution results in a stable compound, e.g., which does not spontaneously undergo transformation such as by rearrangement, cyclization, elimination, etc.

As used herein, the definition of each expression, e.g., alkyl, m, any particular R group, etc., when it occurs more than once in any structure, is intended to be independent of its definition elsewhere in the same structure.

By "Therapeutic agent" is meant any agent that produces a preventative, healing, curative, stabilizing, or ameliorative effect.

By "treating" is meant administering a pharmaceutical composition for prophylactic and/or therapeutic purposes. Prophylactic treatment may be administered, for example, to a subject who is not yet ill, but who is susceptible to, or otherwise at risk of, a particular disorder, e.g., cancer. Therapeutic treatment may be administered, for example, to a subject already suffering from a disorder in order to improve or stabilize the subject's condition. Thus, in the claims and embodiments described herein, treating is the administration to a subject either for therapeutic or prophylactic purposes. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of a disease, the healing of an existing disease, and the amelioration of a disease.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The invention described herein further features a pharmaceutical composition for the treatment, prevention, or amelioration of a disease associated with the function of PKM2, which comprises an activator of PKM2 activity (e.g., a selective activator of PKM2) and a pharmaceutically acceptable carrier. The activator is present in an amount that, when administered to a patient, is sufficient to treat a disease in a patient. The composition may be formulated as, e.g., a pill, a powder, a granulate, a suspension, an emulsion, a solution, a gel, a paste, an ointment, a cream, a foam, a lotion, a plaster, a suppository, an enema, an injectable, an implant, a spray, or an aerosol. The composition may be, e.g., formulated for targeted delivery or for extended or delayed release. The composition may be, e.g., formulated for oral, buccal, topical, rectal, subcutaneous, vaginal, inhalation, ophthalmic, parenteral, intravenous, or intramuscular administration.

In some embodiments, the pharmaceutical composition further comprises an additional therapeutic agent useful in the treatment of a patient suffering from or susceptible to a disease or condition selected from cancer, atherosclerosis, restenosis, an autoimmune disorder, a proliferative disorder, or obesity, in a more specific embodiment, the additional therapeutic agent is selected from a chemotherapeutic agent, an immune modulatory agent, a metabolic modulator, an anti-diabetes drug, insulin, or an insulin analog or derivative.

The invention described herein features a kit that includes a pharmaceutical composition containing a PKM2 activator and instructions for administering the composition to a patient having a disease associated with the function of PKM2. The kit may further include an additional therapeutic agent. The additional therapeutic agent will be appropriate for the disease or condition to be treated by the kit, and may be selected, e.g., from any of the additional therapeutic agents set forth above for combination therapies.

In another aspect, the invention features a method for evaluating a candidate compound for the ability to activate PKM2. The method includes providing a PKM2 polypeptide which includes at least the FBP binding region of PKM2; contacting the PKM2 polypeptide and the candidate compound; assessing the ability of the candidate compound to activate PKM2; and optionally, determining if the candidate compound binds to PKM2, thereby evaluating a candidate compound for the ability to activate PKM2.

In another embodiment the ability of the compound to activate PKM1, PKR, or PKL is determined and compared with the ability of the candidate compound to activate PKM2.

In yet another embodiment, the PKM2 polypeptide is a polypeptide present in human PKM2. It can include one or more of the following human PKM2 amino acids: Thr432, Lys433, Ser434, Ser437, Trp482, Arg489, Gly514, Gly518, Ser519, Gly520, and Phe521 (e.g., residues identified by crystallographic studies that form salt bridges and hydrogen bonds with FBP), and/or K433, D488, R489, R455, T454, T434, and N456 (e.g., residues that potentially define the phosphotyrosine binding pocket) or other Pleckstrin Homology-pH domain pockets. In another embodiment, the polypeptide includes all or a portion of the PKM2 sequence from T432-G514. In other preferred embodiments, the PKM2 polypeptide includes sufficient sequence to allow FBP binding or FBP binding, or inositol/phosphate binding and phosphotyrosine-modulated release of a sugar analog/phosphate or FBP. In another embodiment, the PKM2 polypeptide includes the entire PKM2 sequence. Preferably, the PKM2 polypeptide is present as a tetramer.

In another embodiment, contacting the PKM2 polypeptide and the candidate compound can include: forming a reaction mixture (e.g., a cell-free mixture) containing the PKM2 polypeptide, which can, e.g., be purified or partially purified, and the candidate compound; contacting a cell that expresses the PKM2 polypeptide, e.g., a cancer cell, with the candidate compound; or administering the candidate compound to an animal that expresses the PKM2 polypeptide.

In a particular and specific embodiment, a reaction mixture is formed and includes FBP or inosito/phosphates or analogs. Such embodiments are useful in evaluating compounds that activate PKM2 by inhibiting the release of FBP or sugars from PKM2.

In another specific embodiment, the reaction mixture excludes FBP. Such embodiments are useful in evaluating compounds which mimic or are agonists of FBP.

In another embodiment, the reaction mixture includes one or more of substrate, cofactor, buffer, and assay or readout reagents.

In another embodiment, a reaction mixture is formed and includes FBP and phosphotyrosine peptide, or inositol phosphates/analogs and phosphotyorosine peptide or mixtures of all. Such embodiments are useful in evaluating the candidate compound's ability to activate PKM2 by inhibiting the release of FBP from PKM2 in the presence of phosphotyrosine peptide.

In another embodiment, assessing includes the step of evaluating the level of a substrate consumed or a product produced by a reaction catalyzed by PKM2 directly or indirectly. This can include measuring the products of a PKM2 reaction, e.g., ATP or pyruvate, or in a coupled reaction with the presence of lactate dehydrogenase measuring the consumption of NADH and/or the production of lactate, in specific embodiments, the readout of the assessment is made spectroscopically, e.g., colorimetrically or fluorometrically. In another embodiment, the level or rate of consumption/production is compared with a positive control. If the level or rate is equal to or greater than the control, the candidate compound is selected.

In another embodiment, assessing includes using labeled reagents, e.g., a radioisotope-labeled glucose, and scintillation counting to follow the fate of that reagent. Assessing can include measuring PKM2 activity directly by measuring the consumption of ADP or phosphoenolpyruvate, or by measuring the production of ATP or pyruvate. These measurements may be made spectroscopically or by any other method. Production of ATP can also be measured using luminescence by coupling the PKM2 reaction to the luciferase reaction. A change in cellular oxygen consumption can also be measured.

In another embodiment, assessing includes using a coupled enzyme reaction in the presence of a second enzyme that utilizes the product of pyruvate kinase reaction (pyruvate and ATP). In another embodiment, the second enzyme is lactate dehydrogenase which converts pyruvate to lactate in the presence of NADH. In another embodiment, the production of ATP can be measured by a bioluminescence ATP assay.

In another embodiment, the observed ability of the candidate to activate PKM2 is compared with a control or preselected value, and if the observed ability meets a preselected relationship with the control or preselected value, e.g., it meets or exceeds, the candidate compound is selected for further analysis.

Further analysis can include confirming that the candidate compound activates PKM2. In one embodiment, the method further includes performing a second evaluation for the ability to activate PKM2 by the same method. In another embodiment, the method further includes performing a second evaluation for the ability to activate PKM2 by a different method. In certain embodiments, the first method is a cell-free system and the second is a cell-based assay. In alternate embodiments, the first method is a cell-free or cell-based method and the second method is an animal-based method.

In a specific embodiment, the confirmatory assay includes the step of performing a second evaluation for the ability of the candidate compound to activate PKM2 by contacting the candidate compound with a cell and measuring the consumption of oxygen or production of lactate by the cell in other specific embodiments, a decrease in any of cellular phosphoenolpyruvate, glycerol-phosphate, ribose or deoxyribose, lipid synthesis, or glucose conversion to lipid or nucleic acids or amino acids or protein by the cell can be used to confirm the ability of the candidate compound to activate PKM2. The evaluation could include measuring an increase in pyruvate but this is hard to measure in a cell-based assay. The measurement could also determine alteration in mitochondrial membrane potential e.g., as measured by fluorescent potentiometric dyes.

In certain embodiments, the confirmatory assay employs an animal-based assay, e.g., one which uses a mouse or rat, and which allows assessment of the ability to activate PKM2 in the animal. In some embodiments, the candidate compound is contacted with a test animal and the conversion of $^{13}$C-labeled glucose to pyruvate or lactate or ribose or other metabolites is followed by MRI in vivo or by mass spectrometry of metabolites from extracted tissues. In certain embodiments, the animal model is evaluated by a method which monitors glucose uptake, e.g., a PET or MRI scan.

In specific embodiments, the candidate compound has one or more properties described herein, e.g., one or more of the following properties: the candidate compound is an allosteric activator; the candidate compound inhibits the release of FBP; the candidate compound is an agonist of FBP, e.g., an agonist which binds with a lower, about the same, or higher affinity than does FBP; the candidate compound which can be ANY and ALL inositol derivatives and their phosphates, and inositol analogs thereof incorporated by reference herein, inhibits the dissolution of tetrameric PKM2; the candidate compound promotes the assembly of tetrameric PKM2; the candidate compound selectively activates PKM2 over at least one other isoform of PK, e.g., the candidate compound is selective for PKM2 over PKR, PKM1, or PKL; or the candidate compound has an affinity for PKM2 which is greater than its affinity for at least one other isoform of PK, e.g., PKR, PKM1, or PKL. In another embodiment, the method of evaluating the ability of a candidate compound to activate PKM2 further includes evaluating the candidate to determine if it has one of the properties described herein.

In another embodiment, more than one candidate compound is evaluated simultaneously.

In another embodiment, the method of evaluating the ability of a candidate compound to activate PKM2 includes the step memorializing the outcome of an evaluation or assay described herein.

In another aspect, the invention features a method of evaluating a candidate structure for its ability to interact with PKM2. The method can be used to evaluate a candidate structure for use or further investigation for use as an inhibitor or activator of PKM2. The method includes: providing a three dimensional representation of a PKM2 structure, which includes a portion of PKM2 including the FBP binding pocket and preferably Lys433; providing a three dimensional representation of a candidate structure; and evaluating a relationship, e.g., fit, distance, or spatial overlap, between the PKM2 and candidate structures, or between an atom, amino acid, or moiety on the PKM2 structure and an atom or moiety on the candidate structure, thereby evaluating the candidate structure for its ability to interact with PKM2.

The crystal structure of PKM2 complexed with FBP has been reported (see, e.g., Dombrauckas et al., Biochemistry 44:9437-29, 2005, incorporated by reference herein.

Art-known methods can be used to generate three-dimensional representations of molecules for which the structure is provided or which have been purified or crystallized. Art known methods can be used to produce computer-generated simulations which allow structural comparisons, such as the ability of a candidate structure to "dock" with PKM2.

In another embodiment, a three-dimensional structure can be generated by a modeling program which predicts the three-dimensional structure, for example, from the primary sequence of a protein or peptide. In another embodiment, a three-dimensional structural representation can be generated from a crystal structure.

In another embodiment, the conformation of activator molecules bound to PKM2 can be obtained from NMR measurements of the co-complex of a small molecule activator and PKM2. In some embodiments, the PKM2 structure is provided for a PKM2 bound to FBP. In other embodiments, the PKM2 structure provided is that of PKM2 without bound FBP. In some embodiments, the PKM2 structure provided is bound to a phosphotyrosine-containing polypeptide.

In some embodiments, evaluating includes determining the distance between an atom or moiety of the candidate structure and an atom or moiety of a residue of PKM2, e.g., of a residue in or near, e.g., within 5 angstroms of, the FBP binding pocket, for example, determining if an atom or moiety of the candidate structure and an atom or moiety on the FBP binding pocket make contact or come within a pre-selected distance of one another.

In some embodiments, evaluating includes evaluating the relationship of an atom or moiety of the candidate structure with an atom or moiety of the binding pocket, an atom or moiety of PKM2 within 3 angstroms of the binding pocket, an atom or moiety of FBP or inositol phosphate residing in the binding pocket, or with an atom or moiety of Lys433.

In some embodiments, evaluating includes determining whether the candidate structure displaces a ligand in the FBP binding pocket or PH domain pocket or would result in steric hindrance with a bound ligand, e.g., FBP, in the FBP pocket or PH domain. In other embodiments, evaluating includes determining whether the candidate structure would interfere with occupancy of a ligand in the FBP binding pocket. In other embodiments, evaluating includes determining whether the candidate structure displaces a ligand in a binding pocket or would interfere with release of a ligand in the FBP binding pocket or another binding pocket.

In some embodiments, evaluating includes determining whether a shift of amino acid K433 occurs when fitting or docking the PKM2 and candidate structures. In some embodiments, the evaluating includes determining whether one or more interactions occur between the two structures. Exemplary interactions include hydrogen bonding, formation of a salt bridge, hydrophobic interactions, and hydrogen interactions.

In some embodiments, the method further includes making a record of the evaluation, for example, in a tangible medium such as computer memory or on paper. In another embodiment, the record includes an identifier for the candidate structure and a value for a parameter related to the relationship evaluated.

In another embodiment, the method further includes providing a second candidate structure and repealing one or more of the above recited steps on the second candidate structure. In another embodiment, the evaluations for the first and second candidate structures are compared and one is selected for further analysis.

In another embodiment, the method further includes providing instructions to synthesize, purchase, or otherwise obtain a candidate structure evaluated by the method. The identity of a candidate to be synthesized, purchased, or otherwise obtained can be memorialized by creating a record of the identity of the candidate, for example, in a tangible medium such as computer memory or on paper.

In another embodiment, the candidate is tested for its ability to interact with PKM2.

In another aspect, the invention features a pharmaceutical composition of any of the activators described herein.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

3. Compounds

In the following discussion, for the invention compounds, reference will be made to D-chiroinositol, its phosphorylates, and derivatives of either, but it should be understood that the present invention, unless specifically indicated otherwise, or the context requires or the avoidance of prior art requires, includes the corresponding compounds based on any other inositol isomer. Where exclusion is not explicit in this specification, but is required due to prior art, the invention compounds are to be deemed to exclude such prior art compounds in particular, and preferably exclude compounds having the same substituent pattern exactly as the prior art compounds but based on an inositol isomer other than D-chiroinositol or myoinositol, or preferably having the same substituent pattern as the prior art compound but based on an inositol isomer other than D-chiroinositol, or preferably having the same substituents but in the same pattern or a different pattern from that in the prior art molecule based on the same inositol isomer as the prior art compound, or preferably having the same substituents but in the same pattern or a different pattern from that in the prior art molecule based on an inositol isomer other than D-chiroinositol or myo-inositol, or preferably having the same substituents but in the same pattern or a different pattern from that in the prior art molecule based on an inositol isomer other than D-chiroinositol. These exclusions are on a utility-by-utility and composition-by-composition basis so that exclusion of a compound for one utility does not exclude the compound from being within the invention for another utility or exclusion of a compound in one formulation does not exclude the compound for being within the invention for another composition. Every recitation of compounds in this specification as part of the invention is deemed to be the specific recitation as well as the more general recitiations to include the corresponding compounds basal on inositol isomers other than the one specifically mentioned subject to the exclusions set forth in this paragraph, and on the location of prior art that requires exclusion of one or more compounds in a particular use or composition, application of the various exclusions above to the particular recitation in the particular context is deemed to have been specifically recited herein.

4. Uses

In one aspect, the present invention relates to the discovery that signal transduction pathways regulated by either phosphatidylinositol and/or by Shh and its constituents (patched (ptc), gli and/or smoothened) can be inhibited, at least in part, by D-chiroinositol and/or derivatives thereof (as set forth more fully below). While not wishing to bound by any particular theory, the activation of the receptor proteins is believed to be the mechanism by which these agents act. For example, the ability of these agents to inhibit proliferation or patched loss-of function (ptclof) cells may, be due to the ability of such molecules to interact with hedgehog, patched, or smoothened, or at least to interfere with the ability of those receptor proteins to activate a hedgehog, ptc, and/or smoothened-mediated signal transduction pathway. Again, without being bound thereto, it is the inventor's belief that D-chiroinostitol (or a phosphorylated or other derivative thereof, preferably combinations of two or more selected from D-chiroinositol, its phosphates, or other derivatives thereof) stimulates these signaling mechanisms, activating certain isoforms of protein kinases which kinases appear to be involved in neural tube defects prevention.

It is, therefore, specifically contemplated that these small molecules (D-chiroinositol and its derivatives) which interfere with aspects of signal transduction activity will likewise be capable of inhibiting proliferation (or other biological consequences) in cells. In preferred embodiments, the subject inhibitors are organic molecules having a molecular weight less than 2500 amu, more preferably less than 1500 amu, and even more preferably less than 750 amu, and are capable of modulating (inhibiting or activating) at least some of the biological activities of hedgehog proteins, protein kinases and preferably specifically in target cells.

Thus, the methods of the present invention include the use of D-chiro insoitol and/or derivatives thereof (optionally with folate sources) which agonize (mimic) the inhibition of certain receptor complexes of hedgehog signaling, such as by inhibiting activation of downstream components of the signal pathway, in the regulation of repair and/or functional performance of a wide range of cells, tissues and organs, for instance, the subject method has therapeutic and cosmetic applications ranging from regulation of neural tissues, bone find cartilage formation and repair, regulation of spermatogenesis, ovulation, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

In a preferred embodiment, the subject method can be to treat epithelial cells. For instance, the subject method can be used in treating or preventing basal cell carcinoma or other hedgehog pathway-related disorders.

In another preferred embodiment, the subject method can be used as part of a treatment regimen for malignant medulloblastoma and other primary CHS malignant neuroectodermal tumors. Additional exemplary cancers in which the present invention is of use includes those in the following table

| ORGAN OR TISSUE | SPECIES | CELL LINE |
|---|---|---|
| 1. Blood | Human | Erythrolekemia K562 cell line K562 + human bone marrow |
| 2. Colon | Human | Adenocarcinoma HT-29cell line |
| 3. Lung | Rat | Tracheal epithelium + B{a}P |
| 4. Liver | Human | HepG2 cells |
| 5. Mammary | Human | Adenocarcinoma MCF-7, MDA-MB 231 cells |
| 6. Cervix(uterine) | Human | HeLa cells |
| 7. Skin | Mouse | JB6 cells |
|  | Mouse | HEL-30 cells |
| 8. Soft tissue | Mouse | 3T3 fibroblast |
|  | Human | Rabdomyosarcoma, RD cells |

(Shamsuddin Abul& Vucenik, Ivana, Current Cancer Therapy Reviews, 2005, 1,259-269).

In another aspect, the present invention provides pharmaceutical preparations comprising, as an active ingredient which is D-chiroinositol or a derivative thereof with or without a folate source, a receptor antagonist/agonist, or protein modulator, (antagonist/agonist), a kinase antagonist or agonist formulated in an amount sufficient to inhibit, in vivo, proliferation or other biological consequences of aberrant PI3K/Shh cellular signaling, especially ptc loss-of-function, hedgehog gain-of-function, or smoothened gain-of-function.

The subject treatments can be effective for both human and animal subjects. Animal subjects to which the invention is applicable extend to both domestic animals and livestock, raised either as pets or for commercial purposes. Non-limiting examples are dogs, cats, cattle, horses, sheep, hogs, and goats.

The present invention is further a method of treatment so as to avoid or reduce the incidents of fetal malformations and the avoidance or reduction of activation of breast cancer (or breast cancer precursor condition) in either men or women. The treatment and compositions can be administered to men or women are on estrogenic hormonal therapy or anti-androgenic hormonal therapy (which results in an estrogenic/androgenic balance of surplus of estrogenic-receptor effects) or to those with known or suspect highly estrogen sensitive epithelial and/or mammary breast tissue.

One of the significant aspects of the invention is the prevention of or reduction of the risk of birth defects associated with fetal alcohol syndrome, low cholesterol levels during pregnancy, anchor protein kinase overactivity. The method involves administering to a woman during her pregnancy a compound selected from the group consisting of an inositol, a phosphorylate thereof, a derivative of either (as described more fully below), or mixtures thereof. The administration during the first trimester is of particular value, especially because the fetus is most sensitive to aberrations at this time. As such, it is preferred that the women be treated prophylactically in order to assure treatment when she may not realize she is pregnant and therefore may be likely to be consuming alcohol or be treated with cholesterol lowering medications without thinking of the issues of impact on a fetus.

Without being bound to theory, it is the inventor's belief that exposure to alcohol during the critical period during first trimester embryonic development may inhibit efficient transcription of genes, especially those related to expression of proteins involved in proper mapping during fetal development. This in turn leads to impaired signal transduction during fetal mapping. Also, mutations in genes that encode specific kinases that produce phosphate-responsive promoters for proper gene expression may also be impaired during alcohol exposure. It is also the inventor's belief that alcohol induces hyperactive active states of gene encoding phosphate kinases which may contribute to defective or loss of shh signaling. Therefore, supplementing alcohol exposed fetuses by administering at least one of an inositol (especially myo-inositol and/or D-chiroinositol, particularly D-chiroinositol) and/or a phosphorylate thereof (especially a polyphosphorylate thereof as further defined herein) and/or a derivative of the foregoing (as further defined herein) optionally in the presence of a folate source (preferably folic acid) (to inhibit hyperactive states of protein kinases) should restore proper signaling and prevent major birth defects related to fetal alcohol exposure. In addition, supplementing the embryos with these compounds will also rescue the loss of proper shh gene expression and/or inhibit hyperactive states of certain protein kinases that impair transcription factors. This leads to the use of these compounds for the prevention of these common congenital defects related to fetal alcohol syndrome.

Again, without being bound to theory, the present inventor believes that the low cholesterol levels also result in a negative impact on signaling and is the basis for the thought that statins might be teratogenic and therefore contraindicated during pregnancy. The inventor believes that supplementation with the above inositols (the free inositols, phosphorylates thereof and/or derivatives of either or mixtures thereof) optionally in the presence of a folate source (preferably folic acid) can restore (at least in part) proper mapping function in those individuals who have low cholesterol levels, either naturally or have low cholesterol levels due to use of cholesterol lowering medications such as statins and/or fibrates.

In the foregoing situations, the use of the above compounds (inositols, phosphorylates thereof, and/or other derivatives of either as defined herein) are useful for the prevention or reduction in incidence of fetal alcohol syndrome defects (FASD) as well as safeners for the use of alcohol or cholesterol lowering medications in women who are pregnant as well as those who may be pregnant and not yet be aware of the pregnancy.

Administration of the above compounds is clearly indicated when the patient is a women of child bearing age and is known to be pregnant. It is especially of use when the patient, is known to be a frequent user of alcohol and is not a candidate to adhere to an alcohol free pregnancy. However, since it is unclear as to whether even infrequent alcohol use can give rise to FASD, it is preferable to generally use the above compounds in a prophylactic general manner with all women who are pregnant so as to minimize the rate of FASD overall. In addition, since a particularly sensitive time period for the fetus is the early stages of pregnancy (first trimester, especially the first month) and this is the precise period when a woman is least likely to know she is pregnant, it is the most likely time when fetal injury can occur due to alcohol and/or depressed cholesterol. Thus, the inventor believes that the above compounds should be used prophylacticly in all women of child bearing age who utilize alcohol on a regular basis and in all women of child bearing age who are either on cholesterol lowering medications or who naturally have abnormally low cholesterol levels.

The subject methods and compounds may be used to regulate proliferation and/or differentiation of cells in vitro and/or in vivo, e.g., in the formation of tissue from stem cells, or to prevent the growth of hyperproliferative cells to illustrate but a few uses. For example, according to the present invention, large numbers of non-tumorigenic neural progenitor cells can be perpetuated in vivo and their differentiation and proliferative rates can be amplified preferably in the presence of growth factors by contacting the cells with the subject compound.

II. Particulars

A. Compounds

Certain compounds of the present invention may exist in particular geometric or stereoisomeric forms. The present invention contemplates all such compounds, including, cis- and trans-isomers, R- and S-enantiomers, diastereomers. (D)-isomers, (L)-isomers, especially the racemic mixtures (racemates) thereof, and other mixtures thereof, as falling within the scope of the invention, except that chiro inositol and the phosphates and derivatives thereof used in the present invention have the inositol ring (i.e. a six carbon 6 membered ring, with each carbon having one H and one OH in the underivitized form) and especially in the form of D-chiroinositol. In some embodiments this limitation to the D-chiro form of inositol (its phosphorylates and derivatives of either) is to the exclusion of the other isomeric forms of inositol regardless of the actual naming convention of the complete molecule. In other embodiments of the invention, the invention requires an inositol, a phosphorylate thereof or a derivative of either without being limited to the D-chiroinositol structural form. In some contexts, this will be specifically pointed out and in others, as indicated in the definitions section of this specification, the exclusion of compounds will be on the basis that such compounds are part of the prior art in a limited number of contexts. Additional asymmetric carbon atoms may be present in a substituent such as an alkyl group. All such isomers, as well as mixtures thereof, are intended to be included in this invention.

For convenience, the structure of D-chiroinositol is as follows and the naming convention used herein follows that shown, regardless of whether the IUPAC naming convention differs for this particular compound or its derivatives:

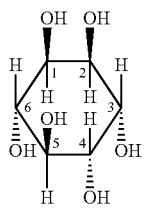

In the substituted compounds of the invention, to the extent that the compounds retain either hydroxyl groups or have hydroxyl groups in which the hydrogen of the hydroxyl has been replaced, the retention of the special arrangement of the shown hydroxyl groups by the retained hydroxyls or the inositol ring carbon-Oxygen bond of the derivatized compound or the inositol ring carbon-carbon or other heteroatom bond replacing one or more of the D-chiroinositol hydroxyl groups defines a D-chiroinositol compound. Replacement of the inositol ring hydrogens will not affect the consideration of the compound as a D-chiroinositol derivative for this application. Thus, in each of the exemplary compounds below where the hydroxy group or derivatized hydroxy group arrangement mimics D-chiro inositol, it is a D-chiroinositol

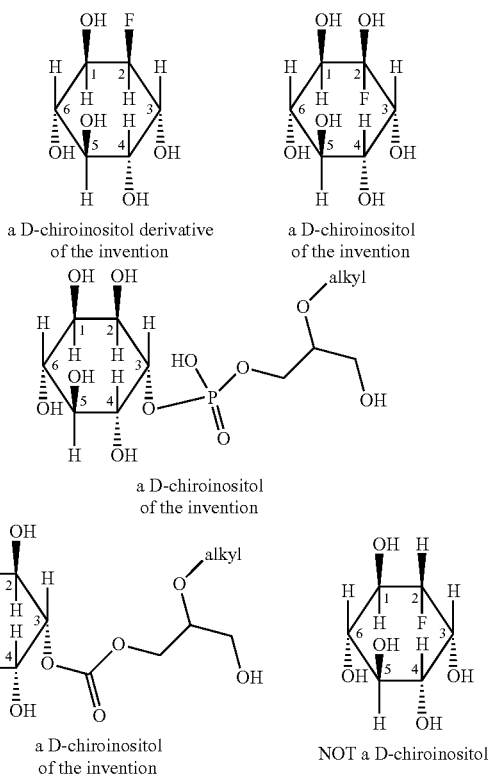

compound of the invention. Where a hydroxyl is replaced by a hydrogen and the other hydrogen is replaced by another group (see the final structure above of this paragraph), then it is not a D-chiroinositol derivative for the present invention, although it is a derivitized inositol and may be within the scope of compounds for other aspects of the invention. However, where both the hydrogen and the hydroxyl of a particular D-chiroinositol ring carbon atom are replaced by substituents (see the structures below), both are to be considered D-chiroinositol derivatives for purposes of the invention regardless of the actual naming convention name, except in the case where one or both are found in the prior art, in which case the prior art compound is not to be considered a D-chiroinositol derivative for the present invention and is subject to the exclusionary aspects indicated above.

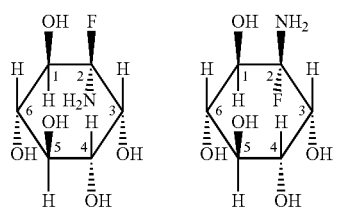

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above delude compounds which otherwise correspond thereto, and which have the same general properties thereof (e.g., the ability to inhibit hedgehog signaling), wherein one or more simple variations of substituents are made which do not adversely affect the efficacy of the compound. In general, compounds which themselves are not inositols, inositol phosphorylates or other inositol derivatives are not considered equivalents for the present invention. The compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CRC Handbook of Chemistry and Physics, 82th Ed., 2001-2002, inside cover.

B. Exemplary Compounds of the Invention.

As described in further detail below, it is contemplated that some of the subject methods can be carried out using any of D-chiroinositol, D-chiroinositol phosphates, or a variety of different D-chiroinositol derivatives or mixtures thereof which can be readily identified, e.g., by such drug screening assays as described herein. Other aspects of the invention can be carried out by these same D-chiroinositols as well as the corresponding inositols which are based on inositol isomers other than the D-chiro form. These other inositol forms when underivitized, differ from D-chiroinositol only in the particular orientation of the hydroxy groups.

D-chiro-inositol is a compound of the structure I

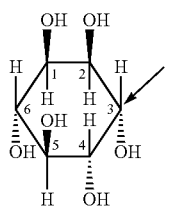

I

D-chiro inositol is not present in dietary sources and is derived from soil. Any such compound available to the body must be made by conversion of other sources, either systemically or artificially. The most common source of inositols is myo-inositol, which does occur in dietary sources. Myo-inositol differs from D-chiro-inositol by inversion of the OH and H at the position indicated by the arrow in Figure I above. Methods of making D-chiro-inositol are detailed in a number of patents, among them, U.S. Pat. Nos. 5,091,596; 5,406,005; 5,463,142; 5,714,643, 5,932,774; and 6,660,891, all of which are incorporated herein by reference. Phosphates thereof for purposes of the present invention include those having one or more of the hydroxyl groups in formula I above phosphorylated. These include mono-, di-, tri-, tetra-, penta-, hexa-monophosphates, and heptaphosphates. For convenience, the phosphates of D-chiroinositol will be referred to herein by the term D-chiroIP$_x$, where x refers to the number of phosphorylated hydroxyl groups that are present. Where there is one or more numbers present as in 1,2-D-chiroIP$_2$, the designation indicates the position of the phosphate(s) based on the position numbering in Figure I above. A designation such as 1,2-D-IP$_3$ indicates that positions 1 and 2 are phosphorylated and that another position is phosphorylated, but that it can be at any other position. The absence of any numerical designation before the "TP" indicates that the phosphate groups are not restricted to any particular positions). The use of the term "TP" without the designation "D-chiro" shall mean that inositol phosphates more generally and include phosphorylated forms of any isomeric form of inositol. Specific mention of particular isomeric forms of inositol, such as myo-, or scyllo-, epi-, etc with the "IP$_x$" designation shall refer only to that particular inositol isomer phosphorylated in accordance with the numeric prefix and "x" designation in the foregoing convention. Thus, the present invention relates to compositions and methods of use of D-chiroinositol, its monophosphates (D-chiroIP$_1$), diphosphates (D-chiroIP$_2$), triphosphates (D-chiroIP$_3$), tetraphosphates (D-chiroIP$_4$), pentaphosphates (D-chiroIP$_5$), and hexaphosphate (D-chiroIP$_6$). A compound indicated as D-chiroIP$_7$, indicates a D-chiroinositol having 1 pyrophosphate and 5 monophosphate groups or 2 pyrophosphate groups and 3-monophosphate groups, or 3-pyrophosphate groups and one monophosphate groups. Higher subscripts for the IP indicate similar multiple pyrophosphate and/or monophosphate groups. While polyphosphates of 3 or more linked phosphates (such as —O—P(O)(OH)—O—P(O)(OH)—O—P(O)(OH)—O—) are possible, they are more prone to rapid hydrolysis and therefore less desirable. D-chiroinositol has 6 distinct monophosphates, 15 distinct di(mono)phosphates, 20 distinct tri(mono)phosphates, 15 distinct tetra(mono)phosphates, 6 distinct penta (mono)phosphates, and 1 hexaphosphate, each of which are intended to be included within the scope of the present invention (unless otherwise noted or the context compels otherwise). These are 1-D-chiroIP$_1$, 2-D-chiroIP$_1$, 3-D-chiroIP$_1$, 4-D-chiroIP$_1$, 5-D-chiroIP$_1$, 6-D-chiroIP$_1$, 1,2-D-chiroIP$_2$, 1,3-D-chiroIP$_2$, 1,4-D-chiroIP$_2$, 1,5-D chiroIP$_2$, 1,6-D-chiroIP$_2$, 2,3-D-chiroIP$_2$, 2,4-D-chiroIP$_2$, 2,5-D-chiroIP$_2$, 2,6-D-chiroIP$_2$, 3,4-D-chiroIP$_2$, 3,5-D-chiroIP$_2$, 3,6-D-chiroIP$_2$, 4,5-D-chiroIP$_2$, 4,6-D-chiroIP$_2$, 5,6-D-chiroIP$_2$, 1,2, 3-D-chiroIP$_3$, 1,2,4-D-chiroIP$_3$, 1,2,5-D-chiroIP$_3$, 1,2,6-D-chiroIP$_3$, 1,3,4-D-chiroIP$_3$, 1,3,5-D-chiroIP$_3$, 1,3,6-D-chiroIP$_3$, 1,4,5-D-chiroIP$_3$, 1,4,6-D-chiroIP$_3$, 1,5,6-D-chiroIP$_3$, 2,3,5-D-chiroIP$_3$, 2,3,6-D-chiroIP$_3$, 2,4,5-D-chiroIP$_3$, 2,4,6-D-chiroIP$_3$, 2,5,6-D-chiroIP$_3$, 3,4,5-D-chiroIP$_3$, 3,4,6-D-chiroIP$_3$, 3,5,6-D-chiroIP$_3$, 4,5,6-D-chiroIP$_3$, 1,2,3,4-D-chiroIP$_4$, 1,2,3,5-D-chiroIP$_4$, 1,2,3,6-D-chiroIP$_4$, 1,2,4,5-D-chiroIP$_4$, 1,2,4,6-D-chiroIP$_4$, 1,2,5,6-D-chiroIP$_4$, 1,3,5,6-D-chiroIP$_4$, 1,4,5,6, -D-chiroIP$_4$, 2,3,4,5-D-chiroIP$_4$,2,3,4,6-D-chiroIP$_4$, 2,3,5,6-D-chiroIP$_4$, 2,4,5,6-D-chiroIP$_4$, 1,2,3,4,5-D-chiroIP$_5$, 1,2,3,4,6-D-chiroIP$_5$, 1,2, 3,5,6-D-chiroIP$_5$, 1,2,4,5,6-D-chiroIP$_5$, 1,3,4,5,6-D-chiroIP$_5$, 2,3,4,5,6-D-chiroIP$_5$, and 1,2,3,4,5,6-D-chiroIP$_6$.

In addition to these phosphates, the invention also includes the corresponding pyrophosphates where at least one of the hydroxyl groups is phosphorylated by a pyrophosphate rather than a monophosphate group, such as without limitation compounds such as

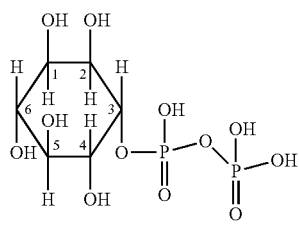

II which would be 3-pyrophosphatidyl D-chiroinositol. Any of the 6 hydroxy positions of the inositol ring can be substituted by a pyrophosphate and some can be unphosphorylated or monophosphorylated with others pyrophosphorylated or phosphorylated with higher phosphates. Non-limiting examples of mixed mono- and pyro phyosphorylated D-chiroinositol include: the heptaphosphates such as 1,2,3,4,5-pentamonophosphatidyl-6-pyrophosphatidyl-D-chiroinositol; 1,2,3,4,6-pentamonophosphatidyl-5-pyrophosphatidyl-D-chiroinositol; 1,2,3,5,6-pentamonophosphatidyl-4-pyrophosphatidyl-D-chiroinositol; 1,2,4,5,6-pentamonophosphatidyl-3-pyrophosphatidyl-D-chiroinositol; 1,3,4,5,6-pentamonophosphatidyl-2-pyrophosphatidyl-D-chiroinositol; and 2,3,4,5,6-pentamonophosphatidyl-1-pyrophosphatidyl-D-chiroinositol; the octaphosphates such as 1,2-dipyrophosphotidyl-3,4,5,6-tetramonophosphatidyl-D-chiroinositol; 1,3-dipyrophosphotidyl-2,4,5,6-tetramonophosphatidyl-D-chiroinositol; 1,4-dipyrophosphotidyl-2,3,5,6-tetramonophosphatidyl-D-chiroinositol; 1,5-dipyrophosphotidyl-2,3,4,6-tetramonophosphatidyl-D-chiroinositol; 1,6-dipyrophosphotidyl-2,3,4,5-tetramonophosphatidyl-D-chiroinositol; 2,3-dipyrophosphotidyl-1,4,5,6-tetramonophosphatidyl-D-chiroinositol; 2,4-dipyrophosphotidyl-1,3,5,6-tetramonophosphatidyl-D-chiroinositol; 2,5-dipyrophosphotidyl-1,3,4,6-tetramonophosphatidyl-D-chiroinositol; 2,6-dipyrophosphotidyl-1,3,4,5-tetramonophosphatidyl-D-chiroinositol; 3,4-dipyrophosphotidyl-1,2,4,5,6-tetramonophosphatidyl-D-chiroinositol; 3,5-dipyrophosphotidyl-1,2,4,6-tetramonophosphatidyl-D-chiroinositol; 3,6-dipyrophosphotidyl-1,2,4,5-tetramonophosphatidyl-D-chiroinositol; 4,5-dipyrophosphotidyl-1,2,3,6-tetramonophosphatidyl-D-chiroinositol; and 5,6-dipyrophosphotidyl-1,2,3,4-tetramonophosphatidyl-D-chiroinositol among others, for example another mixed octaphosphate, without limitation is 1-triphosphatidyl-3-pyrophosphatidyl-4,5,6-trimonophosphatidyl-D-chiroinositol. For simplicity, a pyrophosphatidyl group will be indicated as "PP", and longer phosphate chains will be designated as "Poly(y)P", where y indicates the number of phosphate groups in the chain, and y is generally not more than 4, but typically 3. Any of the tree hydroxy groups of the D-chiroinositol structure can be phosphorylated with either a single phosphate group, a pyrophosphate group or a longer polyphosphate chain of 3 or more phosphate groups and different hydroxyl groups in the same molecule can be phosphorylated with a variety of any of a mono, di, or poly phosphate. Thus, for example, without limitation, 1-monophosphatidyl-2-monopyrophosphatadiyl-D-chiroinositol is also within the scope of the invention, as is 1,2-di(monophosphatidyl)-3,4-diPP-5-Poly(3)P-D-chiroinositol, 1,2,4,5,6-pentamonophosphatidyl-3-pyrophosphatidyl-D-chiroinositol, and 1,2,5,6-tetramonophosphatidyl-3,4-dipyrophosphatidyl-D-chiroinositol along with the corresponding compounds having a different distribution of the mono and pyro phosphatate groups around the D-chiroinositol ring. When sterically possible, two hydroxyl groups of the D-chiroinositol structure (within the same molecule can be linked together through a single phosphate group, PP, or Poly(y)P group forming a ring structure or two or more D-chiroinositol molecules can be linked through such phosphate groups as in the non-limiting structure III:

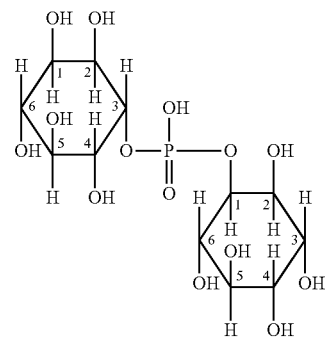

III which exemplifies (but does not limit the invention to) a molecule in which two D-chiroinositol molecules are linked through a single phosphate group between position 3 of one D-chiro-inositol and position 1 of the other. The linking phosphate may be a single phosphate, a PP, or Poly(y)P group, and when two or more hydroxyl groups on the same D-chiroinositol structure are phosphorylated, longer chains of alternating D-chiroinositol and a phosphate (single phosphate, PP or Poly(y)P and mixtures thereof) are realized. Further, a phosphate or a pyrophosphate may link two hydroxyl groups as for example, without limitation, in structure IV below:

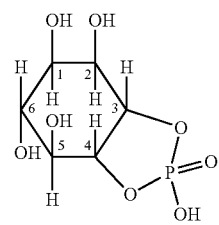

IVa

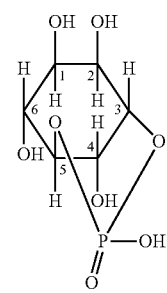

IVb

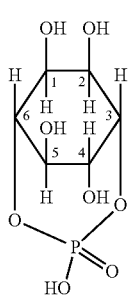

IVc or in a more complex ring structure such as that of form below

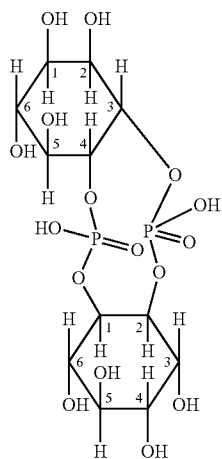

V or the two remaining phosphate hydroxyl groups can be dehydrates to form a P-O-P link as well. In addition, any of the six hydroxy groups that are not phosphorylated can be substituted or replaced as indicated elsewhere in this specification and any of the hydrogen atoms on the six carbons or the inositol ring may be replaced as indicated elsewhere in this specification. Each of these more complex D-chiroinositol structures are also within the scope of the present invention. Manufacture of the compounds having PP or Poly(y)P as the phosphorylating group (whether or not linking multiple D-chiroinositol units together) can be prepared in an analogous fashion to the chemical synthesis of the phosphorylates that have only single phosphate groups for any one hydroxyl group by using pyrophosphate of Poly(y)P phosphate chains as the phosphorylation group source. With respect to the uses set forth herein other than in the prevention and treatment of spina bifida and cancer treatments, the invention compounds also specifically include the corresponding compounds, their phosphorylates and derivatives based on the other inositol isomers as well. For example, of particular interest to the inventor is the use or utility of the inositol higher phosphates and/or pyrophosphates to protect cells from alpha tumor necrosis factor (α-TNF) cell death as seen with autoimmune diseases and pathways involved described above. In analogous fashions to structures IV and V, the P(=O)(OH)— can be replaced by —S(O)— or —S(=O)—.

Formulations in the literature containing chiro-inositol, inositol-phosphates, etc., include, but are not limited to, those disclosed in U.S. Pat. Nos. 5,124,360; 5,614,510; 5,760,222; and 6,784,209, all of which are incorporated herein by reference in their entirety. Formulations of the D-chiro inositols of the invention and their phosphorylated, pyrophosphated, and polyphosphated derivatives as indicated as being useful in the present invention can be made analogously.

In each of the above D-chiroinositol structures and D-chiroinositol phosphate structures, further derivatives of the invention can be made and utilized by replacement of one or more of the hydrogens on the D-chiroinositol ring or one or more of the hydrogens of one or more of the hydroxy groups on the D-chiroinositol ring or one or more of the replaceable hydrogens on one or more of the phosphate groups shown in structures I-V above with a substituent selected form those indicated earlier. In addition, one or more of the hydroxyl groups of the inositol ring can be completely replaced with the "substituents" referred to earlier, except that if such hydroxyl group is completely replaced by hydrogen, then the other hydrogen of the same inositol ring carbon must remain in place to be considered a D-chiroinositol derivative of the present invention (i.e. a deoxy variant), or both the hydrogen and the hydroxyl of the same carbon are replaced by a doubly bound oxygen (an oxo variant) or by a doubly bound nitrogen (an imino variant), while no such restriction generally exists if both the hydrogen and the hydroxyl of the same carbon atom are replaced by substituents which are neither hydrogen nor hydroxyl or derivitized hydroxy. For uses in which the base inositol structure is not limited to the D-chiro inositol configuration, no such limitation on the replacements of the inositol ring hydroxyl group exists, and all such allowable substituents within the above substituent definitions are possible. Other replacements of the hydroxyl group with additionally replacement of the other hydrogen of the same inositol ring carbon retains the consideration of a D-chiroinositol derivative for purposes of the present invention unless specifically set forth otherwise. Preferable, non-limiting groups for the replacement of one or more of these hydrogens on the D-chiroinositol ring carbons include aliphatic groups, acylamino groups, alkoxy alkylamino, alkylthio, amino, aralkyl, carbonyl, derivitized carbonyl, thiocarbonyl, derivitized thiocarbonyl, and aryl to name a few, all of which may be further unsubstituted or substituted in accordance with the aforementioned definitions of each of these terms. Other than the alkylthio and alkoxy, the same set of substituents is preferred for choices to replace replaceable hydrogen of either the D-chiroinositol hydroxy groups or the replaceable hydrogens of the phosphate groups. Also, in any of the foregoing compounds having a D-chiroinositol ring tree hydroxy group, the hydroxyl group can be esterified or etherized and one or more of the remaining hydrogens of the (6) six ring position can be replaced by an appropriate substituent as substituent is defined above. Furthermore, One or more of the hydroxyl groups of the inositol ring can be completely replaced by an appropriate substituent as defined above. Suitable synthetic chemistry will be apparent to synthetic chemists once directed to a particular D-chiroinositol phosphate or derivative.

In other aspects of the invention, the present invention includes the corresponding phosphorylated and/or pyrophosphorylated and/or polyphosphorylated inositols and/or derivitized versions of such inositols or derivitized versions of such phosphorylated, pyrophosphorylated, or polyphosphorylated inositols (which are derivitized in an analogous manner as that set forth for D-chiroinositol above) where for purposes of this paragraph, "inositols" includes all of the inositol isomers for all of the foregoing indications other than the use of myoinositol and its phosphorylates with phosphoric acid (mono- to hexa-monophosphates so that any one to all six of the inositol —OH groups are replaced by a monophosphate) for prevention of spina bifida birth defect and prevention or amelioration of breast cancer.

More specifically, and without limitation to the foregoing, compounds of the present invention (subject to the limitations of certain aspects to those compounds based on the D-chiroinositol configuration and subject to exclusion of certain compounds as set forth with respect to their presence in the prior art as set forth earlier), compounds for use in the present invention include: (i)

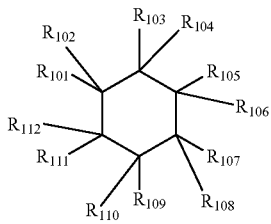

wherein each of $R_{101}$, $R_{103}$, $R_{105}$; $R_{107}$, $R_{109}$, and $R_{111}$ is independently selected from H or a substituent $R_{201}$;
(a) each of $R_{102}$, $R_{104}$, $R_{106}$, $R_{108}$, $R_{110}$, and $R_{112}$ a is independently selected from OH, $OR_{202}$, $OP(=O)(OR_{211})(O_{212})$, $OP(=O)(OR_{113})$—$OP(=O)(OR_{211})(OR_{212})$, $OP(=O)(OR_{113})$—$\{OP(=O)(OR_{113})\}_a$—$OP(=O)(OR_{211})(OR_{212})$ (wherein a is 1-3); or a substituent $R_{203}$; or not more than 3 of $R_{102}$, $R_{104}$, $R_{106}$, $R_{108}$, $R_{110}$, and $R_{112}$ is independently H; or
(b) both of the respective R groups on the same carbon (that is independently pair $R_{101}$ and $R_{102}$, pair $R_{103}$ and $R_{104}$, pair $R_{105}$ and $R_{106}$, pair $R_{107}$ and $R_{108}$, pair $R_{109}$ and $R_{110}$, and pair $R_{111}$ and $R_{112}$) are together =O or =N($R_{204}$); or
(ii)

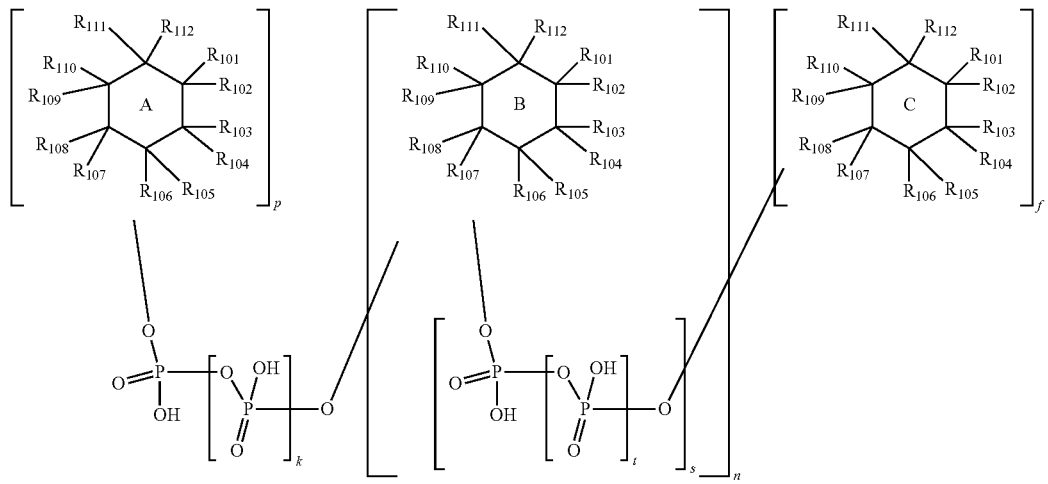

where each of the groups $R_{111}$-$R_{112}$, in each unit are independently as set forth above except that one of such R groups in each of the terminal structures is a direct bond to the indicated oxygen instead of the foregoing, and one of such R groups in each intermediary structure is a direct bond to one of the two indicated oxygens instead of the above and a second of the R groups in each intermediary structure is a direct bond to the other indicated oxygen, p, r, and s are each 1, t and k are each independently an integer of from 0 to 2, and n is a an integer of from 0 to 8; pharmaceutically acceptable salts thereof, and mixtures thereof; or in which in the structure above t=0 and any or all of the —P(O)(OH)— groups are independently replaced by —C(O)—, —S(O)—, or —S(O)$_2$—;
wherein $R_{201}$, $R_{202}$, $R_{203}$, and $R_{204}$ are each independently selected from halogen (preferably fluorine, chlorine, bromine, or iodine, more preferably fluorine, or chlorine, most preferably fluorine); trihalomethyl (preferably trifluoromethyl), cyano, azido, unsubstituted or substituted aliphatic groups, unsubstituted or substituted aromatic groups, —C(O)—$R_{205}$, —C(O)—O—$R_{206}$, —S—C(O)—$R_{207}$, —C(O)—S—$R_{208}$, —C(S)—$R_{205}$, —C(S)—O—$R_{206}$, —S—C(S)—$R_{207}$, —C(S)—S—$R_{208}$, —SC(S)—S—$R_{208}$, —C(N$R_{209}$)—$R_{205}$, —C(N$R_{209}$)—$R_{206}$, —S—C(N$R_{209}$)—$R_{207}$, —C(N$R_{209}$)—S—$R_{208}$, —S—$R_{210}$, —S(O)$R_{210}$, —S(O)O$R_{210}$, —S(O)$_2R_{210}$, —S(O)O$R_{210}$, —N$R_{209}R_{210}$, —N($R_{209}$)—C(O)—O—$R_{206}$, —N($R_{209}$)—C(O)—S—$R_{208}$, —N($R_{209}$)—C(S)—$R_{205}$, —N($R_{209}$)—C(S)—O—$R_{206}$, —N($R_{2069}$)—C(S)—S—$R_{208}$, —N($R_{209}$)—C(N$R_{209}$)—$R_{205}$, —N($R_{209}$)—C(N$R_{209}$)—O—$R_{206}$, —N($R_{209}$)—C(N$R_{209}$)—S—$R_{208}$, —S—$R_{210}$, —N($R_{209}$)—S(O)$R_{210}$, —N($R_{209}$)S(O)O$R_{210}$, —N($R_{209}$)S(O)$_2$O$R_{210}$), —N($R_{209}$)—S(O)$_2R_{210}$, and —N$R_{209}R_{210}$, —P(O)(O$R_{211}$), (O$R_{212}$),
wherein each of $R_{205}$ through $R_{212}$ is itself independently selected from H, an unsubstituted or substituted aliphatic groups, or an unsubstituted or substituted aromatic groups, wherein the aliphatic groups are selected from straight chain and branched carbon chains, whether saturated or unsaturated, of up to 30 carbon atoms, preferably of up to 20 carbon atoms, more preferably of up to 10 carbon atoms, more preferably of up to 7 carbon atoms, most preferably of up to 5 carbons, especially methyl, ethyl, propyl, and cycloaliphatic rings having 3-10 ring members such rings being carbocyclic or heterocyclic where the heterocyclic rings have one to four heteroatoms selected from oxygen, sulfur, and nitrogen; the cycloaliphatic rings being saturated or partially unsaturated, and the aromatic group having 6-8 ring members selected from carbon, oxygen, sulfur, and nitrogen, the aliphatic and aromatic groups further containing up to four fused rings of either cycloaliphatic rings, aromatic rings or both cyclosaliphatic and aromatic rings, each of the aliphatic and aromatic groups being further unsubstituted or substituted by hydroxy, $C_{1-7}$alkoxy, alkylthio, $C_{1-20}$acyloxy, phosphate, halogen (preferably fluorine, chlorine, bromine, or iodine, more preferably fluorine, or chlorine, most preferably fluorine); trihalomethyl (preferably trifluoromethyl), cyano, and azido; each substituent being mono or multiply present as valence permits; and further provided that in the foregoing substitution patterns, no substitution pattern results in a peroxy group; the $R_{211}$ and/or the $R_{212}$ of any —P(O)(OR$_{211}$)(OR$_{212}$) may be further joined to any free hydroxy group or to result in phosphate containing rings such as for example

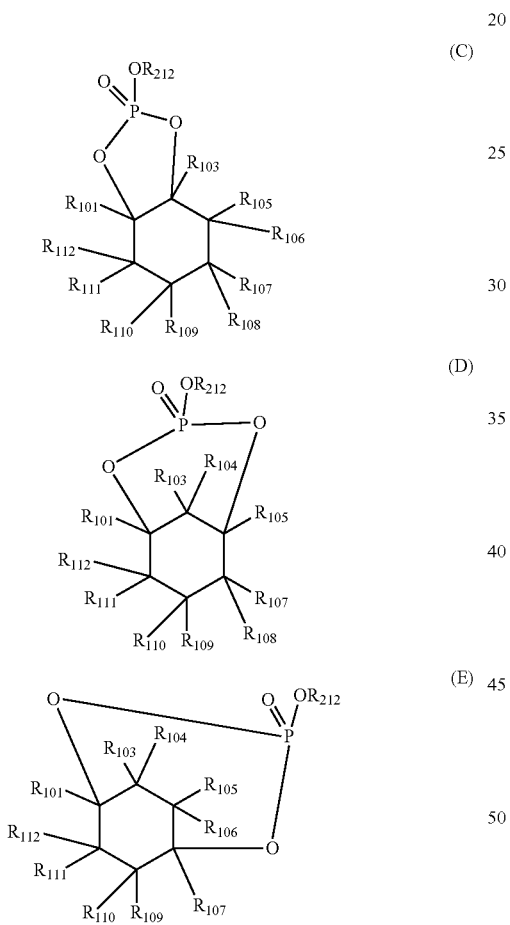

or the corresponding compounds to structures (C), (D), and (E) wherein (a) the

—P(OR$_{212}$)(O)— group is replaced by —C(O)—, —S(O)—, or S(O)$_2$— or the (OR$_{212}$)together with any remaining group $R_{111}$ through $R_{112}$ forms an —O— group resulting in additional fused rings;

wherein each of $R_{205}$ through $R_{213}$ is itself independently selected from H, unsubstituted or substituted aliphatic groups, and unsubstituted or substituted aromatic groups, preferably,

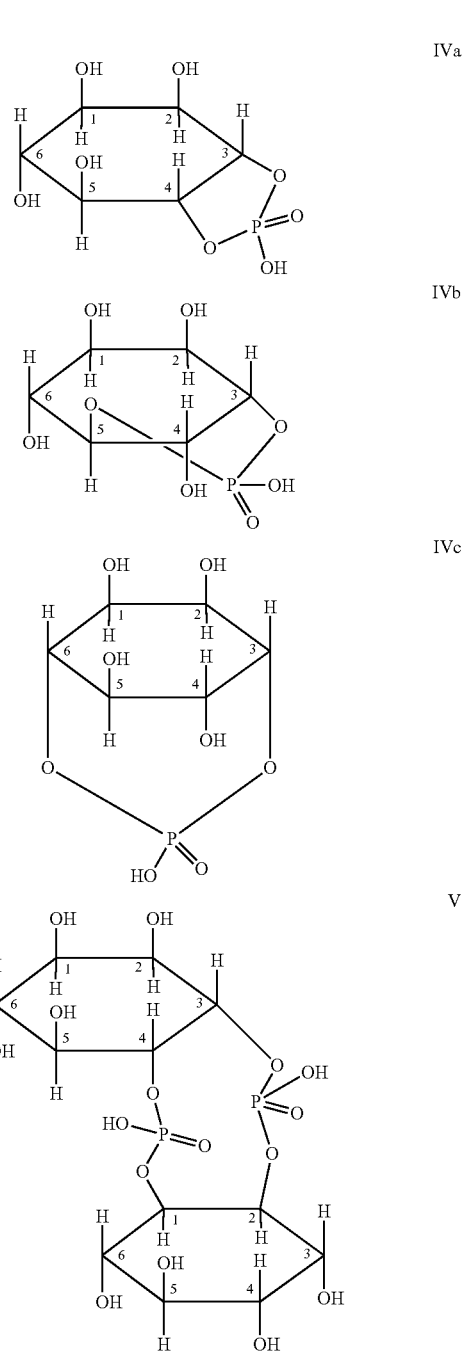

and/or, the $R_{210}$ of any group —S(O)OR$_{210}$ or —S(O)$_2$R$_{210}$ may be joined to any free hydroxy group or to result in —S(O)— or —S(O)$_2$— containing rings analogous to structures IV and V except that the —P(O)(OH)— group is replaced by —C(O)—, —S(O)— or —S(O)$_2$— respectively;

or in which any of the foregoing compounds having a free hydroxy group is esterified with an acidic group of folic acid or an acidic group of a polysaccharide-folic acid compound, or any of the foregoing compounds having a free acidic group such as —P(═O)(OH), —C(═O)(OH), —S(═O)(OH), or —S(═O)$_2$(OH) is esterified with a free hydroxyl group of folic acid or of a polysaccharide-folic acid compound, or in which any of the foregoing having a free amine (—NHR (R being optionally H) or imine (=NH) forms together with the acidic group of a folic acid or of a polysaccharide-folic acid compound an amide (—C(=O)—(NR—), a sulfonamide (—S(=O)₂—NR—), or a group —S(=O)—NR—.

Of particular interest are the multiple phosphorylated inositols having 3 or more monophosphate groups per molecule without other derivatizations, the $IP_7$, $IP_8$, and $IP_9$ inositols without other derivatizations; the derivatized inositols where one or more of the ring hydrogens is replaced with a halogen, especially fluorine, an amino group, an azido group, or a cyano group; the compounds where one or more of the inositol ring hydroxyl group is replaced by a hydroxymethyl; and those having the following substituents

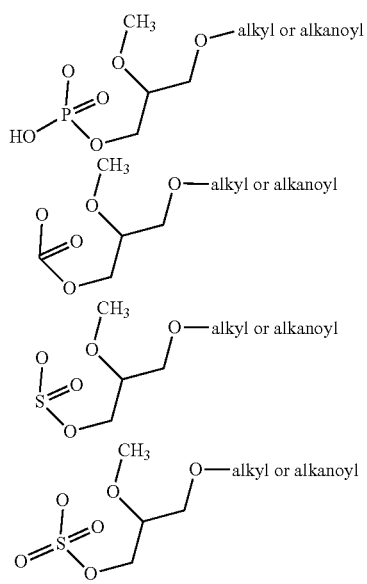

where the alkyl is of 1-30 carbons and saturated or unsaturated, straight chain or branched, preferably octadecyloxy and the alkanoyl is up to 30 carbons and preferably saturated or unsaturated, straight chain or branched, preferably palmitoyl and the substituent, is bound through the free oxygen atom to the inositol ring in place of one of the inositol ring hydroxyl groups or to an inositol analog having a hydroxymethyl group in place of another inositol ring hydroxyl group as for example

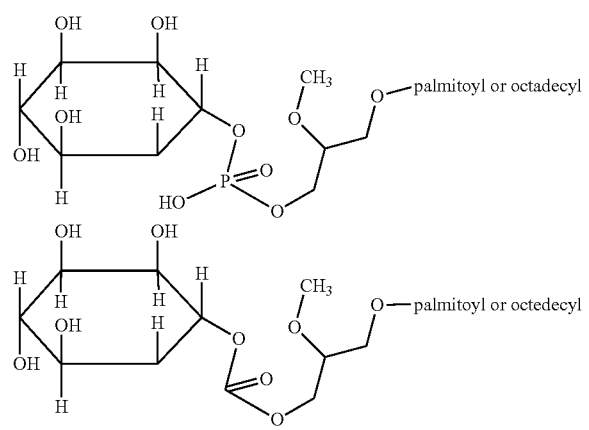

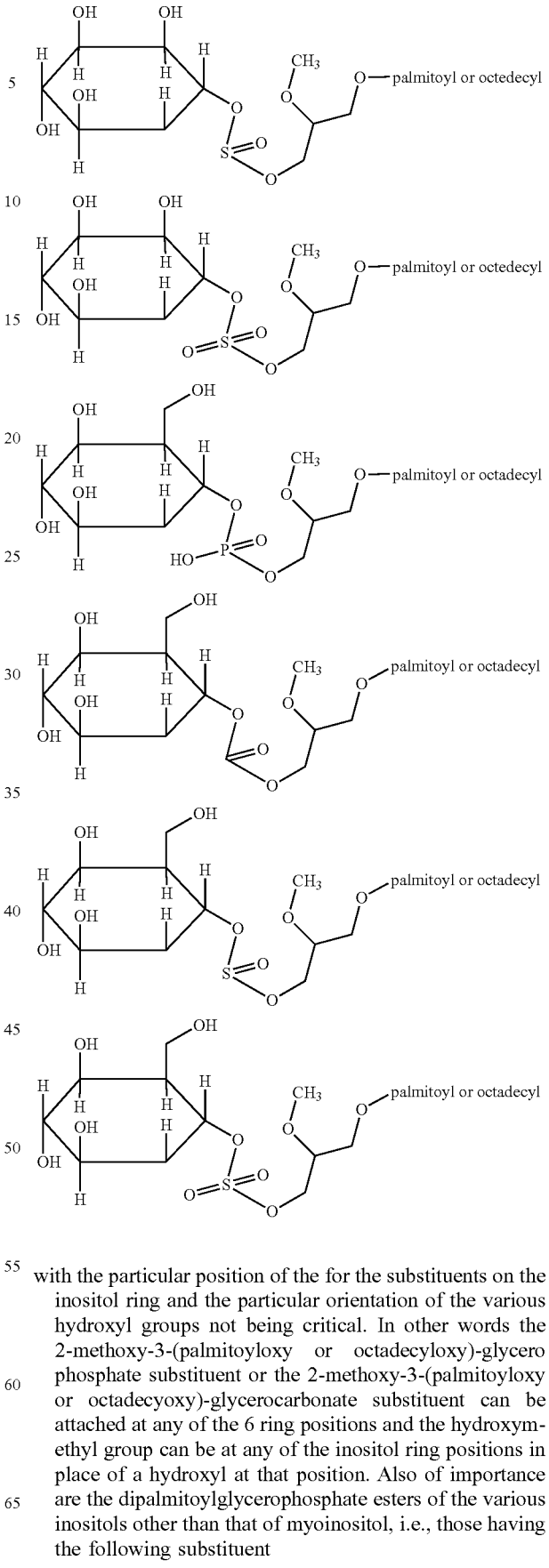

with the particular position of the for the substituents on the inositol ring and the particular orientation of the various hydroxyl groups not being critical. In other words the 2-methoxy-3-(palmitoyloxy or octadecyloxy)-glycero phosphate substituent or the 2-methoxy-3-(palmitoyloxy or octadecyoxy)-glycerocarbonate substituent can be attached at any of the 6 ring positions and the hydroxymethyl group can be at any of the inositol ring positions in place of a hydroxyl at that position. Also of importance are the dipalmitoylglycerophosphate esters of the various inositols other than that of myoinositol, i.e., those having the following substituent

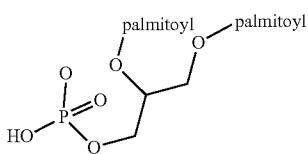

bound through the free oxygen of the phosphate (shown at the left in the structure above) to any of the inositol ring positions (and the corresponding molecules in which the —P(O)(OH)— is replaced by one of —S(O)—, or —S(O)$_2$—) and those that have the dipalmitoylglycerocarbonate esters of the various inositols

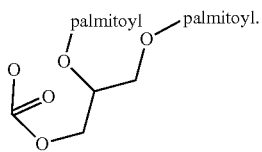

Other important compounds of the invention include those having the group

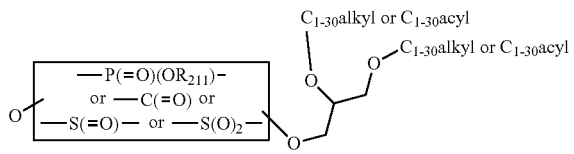

VI bound through the free oxygen shown on the left of the above structure to any of the inositol ring positions. Where the compounds of structure VI has higher acyls (over 14 carbons) as the (C$_{1-30}$alkyl or C$_{1-30}$) groups and the linking group —P(=O)(OH)—, —C(=O)—, —S(O)—, or —S(O)$_2$— is limited to —P(=O)(OH)—, and there is one such group bound to the inositol ring, the compounds are phosphatidylinositols. These phosphatidylinositols being further substituted having such further substitution in patterns in accordance with the present invention compounds are also valuable for as inhibitors for PDK1 and its pathways.

While not including the unmodified, unphosphorylated, underivitized inositol isomers themselves in many embodiments, such isomers having been derivitized and/or phosphorylated are included and include scyllo-inositol, epi-inositol, cis-inositol, allo-inositol, neo-inositol, muco-inositol, dextro-inositol, levo-inositol, and L-chiro-inositol phosphorylations/derivatizations. These materials may be used in amounts of from below 2 mg/day to in excess of 8 grams/kg/day. Any of the above inositols may be used in combination for the inositol component of the invention and may be used with or without other active agents in an analogous fashion as described in more detail above concerning D-chiroinositol. It should be noted that the hedgehog, patched, and GL1,2,3 gain-of function or loss of function can be determined for each of the above inositol based compounds with the screening tests set forth in the examples. Without being limited to theory, those that have hedgehog gain-of-function or smoothened loss-of-function can be used in an analogous manner to the D-chiroinositol uses set forth above and those that have hedgehog loss-of-function or smoothin gain-of-function are not for use in the prevention of birth defects purposes set forth above, but are of use in a number of the other indications of the present invention, especially in the prevention and treatment of various cancers and other indications referred to hereinabove. Some particular compounds that are beyond the D-chiro inositol compounds described earlier are, without limitation, fluoroscylloinositol, fluoroepi-inositol, fluorocis-inositol, fluoroallo-inositol, fluoroneo-inositol, fluoromuco-inositol, fluorodextro-inositol, fluorolevo-inositol, fluoro D-chiro-inositol, deoxyscyllo-inositol, deoxyepi-inositol, deoxycis-inositol, deoxyallo-inositol, deoxyneo-inositol, deoxymuco-inositol, deoxydextro-inositol, deoxylevo-inositol, deoxyD-chiro-inositol, aminoscylloinositol, aminoepi-inositol, aminocis-inositol, aminoallo-inositol, aminoneo-inositol, aminomuco-inositol, aminodextro-inositol, aminolevo-inositol, aminoD-chiro-inositol, ketoscyllo-inositol, ketoepi-inositol, ketocis-inositol, ketoallo-inositol, ketoneo-inositol, ketomuco-inositol, ketodextro-inositol, ketolevo-inositol, ketoD-chiro-inositol, sulfo scylloinositol, sulfo epi-inositol, sulfo cis-inositol, sulfo allo-inositol, sulfo neo-inositol, sulfo muco-inositol, sulfo dextro-inositol, sulfo levo-inositol, sulfo D-chiro-inositol and further sulfato phosphorylates of an inositol isomer where the inositol isomer is selected from the group consisting of scyllo-inositol, epi-inositol, cis-inositol, allo-inositol, neo-inositol, muco-inositol, dextro-inositol, levo-inositol, and D-chiro-inositol; and the inositol compound having at least one phophsoryl group selected from monophosphoryl groups, pyrophosphoryl, groups, and polyphosphory groups and further having at least one sulfato group, which phosphoryl group, and/or sulfato group and/or remaining free hydroxyl groups are each independently unsubstituted or substituted with a suitable substituent as hereinbefore described. Further compounds for use in the invention uses include D-chiro inositol derivative for metabolite is selected from the group of D-chiro-inositol phosphates, d-chiro-inositol esters. D-chiro-inositol ethers, D-chiro-inositol acetals, D-d-chiro-inositol ketals, polysaccharides containing D-chiro-inositols, and D-chiro-inositol phospholipids, which compounds are disclosed in U.S. Pat. No. 6,486,127, incorporated herein in its entirety by reference.

Inositol "salts" contemplated for use in the practice of all aspects of the present invention include any and all pharmaceutically acceptable salts, which may be used in this aspect of the invention as well as the D-chiroinositol more specific aspects set for the earlier. Examples are salts of therapeutically acceptable organic acids, such as acetic, fumaric, lactic, maleic, citric, malic, succinic, toluenesulfonic acid, and the like, salts of polymeric acids, such as tannic acid, alginic acid, carboxymethylcellulose, and the like, and salts of inorganic acids, such as hydrochloric acid, sulfuric acid, and the like. Others, however, may also be utilized. Inositol "derivatives" employed in the practice of this aspect of the present invention (as well as those set forth concerning the D-chiroinositol specific aspects set forth earlier) include those which have been modified as set forth earlier as well as those modified to vary the hydrophilic or lipophilic character of the inositol molecules. Such modifications may be desirable to tailor the solubility characteristics of the inositols to a particular mode or route of administration. For example, lipophilic side chains, including C$_{1-20}$ hydrocarbon chains, which may be saturated or unsaturated and contain one or more non-hydrophilic substituents, may be added, as well as conjugating the inositols to a lipophilic molecule to enhance its lipid solubility. Alternatively, the addition of hydrophilic side chains or inositols conjugates to a hydrophilic molecule will enhance the hydrophilicity of the inositols, including $C_{1-20}$ hydrocarbon chains which may be unsaturated, and may have hydrophilic substituents such as HO, HS, $NH_2$, halo, keto, and the like. Exemplary inositol derivatives contemplated for use in the practice of one aspect of the present invention include amine-substituted, halogen-substituted, deoxy-, keto-, and sulfo-inositol analogues, and the like, as well as combinations of any two or more substituents thereof. Preferred inositol derivatives include substituted inositol derivatives, including hydroxy, amino, halo, e.g., fluoro, deoxy, keto, and sulfo inositol analogues, among other hydrophilic substituents, and combinations thereof, as well as the corresponding salts. In some embodiments of the invention, the further substituents set forth earlier in this specification are useful as well.

C. Exemplary Applications of Methods and Compositions

Folic acid ($C_{19}H_{19}N_7O_6$) and folates are well known in the art as are various formulations thereof. Any of the recognized folates or $C_{19}H_{19}N_7O_6$ is suitable for use in the present invention embodiments that include a folic acid and/or folate component.

Women of child bearing age frequently are avoiding pregnancy by utilizing birth control pills. These are typically estrogenic substances that are administered for a time period and then either stopped for a short time, continued at altered dosage, and/or supplemented or replaced by progestogenic substances so as to induce menses. During the time frame when the estrogenic substance is reduced or stopped, it is possible for a woman to become pregnant. On occasion, it is also possible that the intended "birth control" function of the birth control pills (even when containing a foil complement of the estrogenic substance) may not be totally efficacious, such as when other medications or other substances are ingested that interfere with the proper workings of the birth control medication. In such situations a pregnancy may result despite being on such medications. Although there is a general awareness among pregnant women to have proper supplementation with folic acid, many women taking birth control medication do not take adequate supplements of folic acid or many other nutrients that are important to fetal development, simply because they believe that do not need to be concerned with a pregnancy at that time. Others are simply unaware of the need for adequate supplementation, and still others, even though educated about this either neglect to take appropriate supplements or still don't care. Others do not bother because of economic reasons. One aspect of the present invention is to include supplemental D-chiroinositol (and/or one of its phosphorylated derivatives) into birth control pills which may further have folic acid (or other appropriate folate source) incorporated into some or all of the pills in the birth control pill package so as to assure that the woman taken such birth control has adequate stores of D-chiroinositol (and folate, when folate is also incorporated) in the event that she becomes pregnant either while taking birth control pills or during the time period when she initially stops the birth control pill regimen. This is extremely important since both D-chiroinositol and folate are most effective against the various fetal defects that the present invention is directed toward preventing when these substances are administered pre-conception through the first trimester of pregnancy. The D-chiroinositol (and phosphorylated derivatives) and folic acid (and other folates) can be incorporated into just the tablets of the birth control pill package that have either no other active or have progestogenic but not estrogenic substances or have progesterins and low levels of estrogens present, but preferably are incorporated into all of the tablets. This is suitable because generally the higher estrogenic substance tablets will prevent pregnancy and the remaining tablets will begin administering folic acid and D-chiroinositol (or their counterparts) with the first tablet after the estrogenic tablets. However, it is preferable to have the compounds of the invention in all of the tablets in case of a pregnancy that results from birth control tablet failure or due to interference with proper action of the estrogenic substance due to drug interactions or other dietary or environmental impacts that cause birth control failure.

Another aspect of the invention is a combination product having both D-chiroinositol (and/or a phosphorylated (either P, PP, and/or polyP) derivative thereof and/or other derivative thereof as set forth above) (hereinafter all such compounds collectively referred to, whether as single agents or combinations of these agents, as "the D-chiroinositol compound"), and folic acid (and/or other folate source) in a single composition as a supplement that is especially suited for women of child bearing age who are not yet pregnant (but generally intending to become pregnant), women who are not pregnant and not intentionally trying too become pregnant, but may be, and women who are pregnant. Such fixed combinations may be a standalone product or have other nutritional supplements (or other active agent) incorporated therein. Such additional supplements include vitamins and minerals as well as herbal products and are weft known (both as to substances and their respective dosages) to those of ordinary skill in the nutritional supplement area. Without being held to theory, it is the inventors belief and understanding that co-therapy of (and/or other folate sources) together with D-chiroinositol (and/or phosphorylated derivatives (P, PP and/or polyP) thereof and/or other derivative thereof as set forth above), whether simultaneously or sequentially, operate in a manner that provides the best protective effects against fetal malformations beyond those achievable with either component alone, and further that such results are better than those achieved with each alone or that would have been predicted as additive effect. As such, such co-therapy is also within the scope of the present invention, whether such co-therapy is via a fixed combination $C_{19}H_{19}N_7O_6$ (and/or other folate) and D-chiroinositol (and/or phosphorylated derivates (P, PP and/or polyP) thereof and/or other derivative thereof as set forth above) or via separate administration of these agents generally within 12 hours of each other and generally on a daily basis. Fractional dosing of either or both components taken multiple times a day (i.e., for example ½ daily doses taken twice daily or ⅓ daily dosing taken three times daily) is also within the scope of the present invention. Fractional dosing multiple times a day is particularly suitable when the composition contains only nutritional supplements as active agents and when the patient finds that singe daily doing upsets the stomach or the daily dose is large and not suitable for inclusion into a single unit dosage form.

An additional benefit of administering D-chiroinositol to women on estrogenic medications is downregulating the estrogen-receptor and/or, ErbB receptor overexpressor phenotypes and proliferation from estrogenic insult. For example, D-chiro and/or its derivatives are likely mediated by the production of second messenger lipids that elicit transmemebrane signal transduction cascades governing the activation and inhibition of downstream effectors. These views are also in line with the ideas on non-estrogen receptor associated actions of the compound by way of promoting binding sites that govern cellular proliferation. Thus, incorporation of D-chiroinositol (and/or its phosphorylated (P, PP and/or polyP) derivatives and/or other derivative thereof as set forth above) into fixed combinations with estrogenic medications is a means to increase the safety of the use of estrogenic substances. While D-chiroinositol (and/or its phosphorylated (P, PP and/or polyP) derivatives and/or other derivative thereof as set forth above) can be used as separate medications or supplements in co-therapy with the estrogenic medication, it is highly preferred to have the D-chiroinositol compound as a fixed combination with the estrogenic substance as to assure patient compliance. While estrogenic-sensitive breast tissue in men is rarer than in women, it does occur and co-therapy in men having estrogenic treatment is also within the scope of the present invention. Furthermore, since estrogenic insult is the result of excess estrogen from endogenous overproduction of estrogen, exogenous administration of estrogen, insufficient androgenic production, or exogenous administration of anti-androgens (androgen ablative therapy), the present invention also includes treating men or women with co-therapy of D-chiroinositol compound with anti-androgens, which co-therapy can be by separate administration of the compounds of the invention with such anti-androgens or via fixed combinations therewith. The invention still further includes treating patients with conditions that result in excess estrogen or conditions that result in estrogenic-receptor overexpression phenotypes (whether because of overproduction of estrogen or insufficient androgen production, or congenital deformation in the breast architecture microenvironment) with the D-chiroinositol compound as a means of decreasing the risk of breast cancer from excess estrogenic insult. Finally, in this group of treatments of the invention, the invention further includes treating patients with a general overproduction of hormonal steroids (even though estrogenic/androgenic balance is maintained). A still further benefit to women who are or become pregnant while receiving the present invention treatment is that of reducing the incidents of gestational diabetes (or if they still do have such, it is a milder case), especially since there has been a connection between gestational diabetes and some fetal malformations due poor maternal phosphoinositide turnover or derangement. Specific active agents which can be combined for co-therapy with D-chiroinositol compound and/or derivatives and optionally with addition folic acid (or other folate source) that are within the invention include, without limitation: antiprogestogens, androgens, antiandrogens, estrogens, selective estrogen receptor modulators, aromatase inhibitors, gonadotropins, ovulation stimulators, gonadotropin releasing hormone agonists, gonadotropin releasing hormone antagonists, LHRH agonists, progestins, and anti-progestins, to name a few. Many of these classes are utilized in opposing conditions but the co-therapy with the D-chiroinositol component of the invention and optionally the folate component of the invention is warranted in that in some cases, the effect of the D-chiroinositol component (and optional folate component) is complementary to the other active agent, while in other cases, the D-chiroinositol component (and optional folate component) are protective of one or more of the potential side effects of the other active agent. Specific compounds belonging to these classes of other active agents are exemplified in the following non-exclusive, non-limiting list, each agent of which is prepared in its normal known method and utilized in its known dosage, and include without limitation: 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Agrylin®, Ala-Cort®, Aldesleukin, Alemtuzumab, ALIMTA, Alitretinoin, Alkaban-AQ®, Alkeran®. All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA Avastin®, Azacitidine, BCG, BCNU, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine Carac™, Carboplatin, Carmustine, Carmustine, Wafer Casodex®, CC-5013, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal Cytosar-U,®Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, diftitox, DepoCyt™, Dexamethasone, Dexamethasone acetate, Dexamethasone Sodium Phosphate, Dexasone, Dexrazoxane, DHAD, DIC, Diodex, Docetaxel, Doxil®, Doxorubicin, Doxorubicin liposomal, Droxia™, DTIC, DTIC-Dome®, Duralone®, Efudex®, Eligard™, Ellence™, Eloxatin™, Elspar®, Emcyt®, Epirubicin, Epoetin alfa, Erbitux™, Erlotinib, Erwinia, Etanercept, L-asparaginase, Estramustine, Ethyol, Etopophos®, Etoposide, Etoposide Phosphate, Eulexin®, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gedfitinib, Gemcitabine, Gemtuzumab, ozogamicin, Gemzar®, Gleevec™, Gliadel®, Wafer, GM-CSF, Goserelin, Granulocyte-Colony Stimulating Factor, Granulocyte Macrophage Colony Stimulating Factor, Halotestin®, Herceptin®, Hexadro, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha I fosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Kidrolase®, Lanacort®, Lapatinib, L-asparaginase, LCR, Lenalidomide, Letrozole, Leucovorin, Leukeran, Leukine™, Leuprolide, Leurocristine, Leustatin™ Liposomal, Ara-C Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Muoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nitandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20® with Carmustine Implant, Purinethol®, Raloxifene, Revlimid®, Rheumatrex®, Rituxan®, Rituximab, Roferon-A® (Interferon Alfa-2a), Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Tositumomab, Trastuzumab, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®, etc. A preferred set includes, without limitation: abarelix, abraxane(paclitaxel), adriamycin(doxorubicin), algestone, amadinone, aminoglutethimide, anagestrone, anastrozole, androisoxazole, androstanolone, androstenediol, 4-androstene-3,16,17-trione, aredia(pamidronate disodium), arimidex(anastrozole), aromasin(exemestane), bazedoxifene, benorterone, bicalutamide, bolandiol, bolasterone, bolazine, boldenone, bolenol, bolmantalate, buserelin, calusterone, chemotherapy regimens, (cyclophosphamide (cytoxan), methotrexate(amethopetrin, Mexate, folex, and flourorucil(fluorourcil, 5-fu, adracil) (this therapy is called CMF), cyclophospamide, doxorubicin(adriamycin) and fluorouracil (this therapy is called CAF), doxorubicin(adriamycin) and cyclophosphamide(this therapy is called AC), doxorubicin(adriamycin) and cyclophosphamide with paclitaxel(taxol), doxorubicin(adriamycin) followed by CMF, cyclophosphamide, eprubicin9ellence), and fluororacil, chlorotrianisene, chorionic gonadotropin, cioteronel, cingestol, clogestone, clomegestone, clometherone, clomifene, clostebol, conjugated estrogens, cyproterone, cytoxan(cyclophasphamide), danazol, delmadinone, deslorelin, desogestrel, detirelix, dienestrol, diethylstilbestrol, dimethisterone, dihydrogestrone, drospirenone, drostanolone, dydrogesterone, ellence(epirubicin), epiestriol, epimestrol, epitiostanol, episteride, equilin, esterified estrogens, estradiol, estrazinol, estriol, estrofurate, estrone, estropipate, ethinylestradiol, ethisterone, ethylestrenol, ethynerone, ethynodiol, etonogestrel, evista(raloxifene), exemestane, fareston(toremifene), femara(letrozole), fenestrel, finasteride, fluoxymesterone, flurogestone, flutamide, formebolone, formestane, fosfestrol, fulvestrant, furazabol, ganirelin, gestaclone, geatadienol, gestodene, gestonorone (especially gestonorone caproate), gestrinone, gonadorelin, goserelin, haloprogesterone, herceptin(trastuzumab), histrelin, 4-hydroxy-19-nortestosterone, hydroxyprogesterone, ibutamoren, idoxifene, infliamab, letrozole, leuprolide, leuprorelin, levonorgestrel, lutrelin, lynestrenol, mebolazine, medrogestone, medroxyprogesterone, megace(megestrol), melengestrel, menotropins (especially humegon, pergonal, repronex), mesabolone, mestranol, mesterolone, metandienone, metenolone, methandriol, methenolone, methestrol, methyltestosterone, methynodiol, metribolone, mibolerone, mifepristone, nafarelin, nafoxidine, nandrolone, nilutamide, nitromifene, norboletone, norbolethone, norclostebol, norelgestromin, norethandrolone, norethindrone, norethisterone, norethynodrel, norgestimate, norgestomet, norgestrel, norgestrienone, nylestriol, oxabolone, oxandrolone, oxendolone, oxogestone, oxymesterone, oxymetholone, polyestradiol (especially polyestradiol phosphate), pralmorelin, prasterone, pregesterone, quinbolone, quinestrol, quinestradol, quingestanol (especially quiugestanol acetate), quingestrone, raloxifene, rismorelin, somalapor, somatrem, somatropin, somenopor, somidobove, stanozolol, stenbolone, sumorelin, tamoxifen, taxol(palitaxel), taxotere(docetaxel), testosterone, tibolone, tigestrol, tiomesterone, topterone, toremifene, trenbolone, trimegestone, trioxifene, triptorelin, urofollitropin, vorozole xeloda(capecitabine), zanoterone, and zeranol, zoladex(goserelin), zometa(zoledronic) among others, each of which includes the pharmaceutically acceptable salts and esters thereof. These are all known compounds with known uses and are used in the normal course for those known indications. The co-therapy of the present invention adds the D-chiroinositol compound and optionally folic acid (and/or other folate source) thereto, with the amounts of the D-chiroinositol components and folic acid components being as set forth elsewhere herein. The D-chiroinsoitol and optional folate can be separately administered with these other active agents of combined in fixed combinations therewith as may be convenient.

Turning to the fetal malformations of the present invention, fetal development is a very delicate and sensitive process and there are many points at which something can go wrong, resulting in a congenital defect. As such, no treatment will eliminate all such fetal defects or even all occurrences of any one type of fetal defect. Nonetheless, the administration of D-chiroinositol (and/or phosphorylated derivatives (P, PP and/or polyP) thereof) alone or in combination with folic acid (and/or other folate source) during the first trimester of pregnancy, preferably throughout the first trimester of pregnancy, even more preferably from before conception into the first trimester of pregnancy, and most preferably from before conception through at least the end of the first trimester of pregnancy will significantly reduce the frequency of a wide range of fetal defects, above those reported previously for those patients who have not been treated or those patients who have been treated with either of the D-chiroinositol (and/or its phosphorylated (P, PP and/or polyP) derivatives) or with folic acid (or other folate source) alone (where those treatments have been previously studied. The treatment of the present invention further reduces the frequency of these defects as compared to treatment with other forms of inositol (and/or phosphorylated derivatives thereof) where such treatment has been previously studied.

The defects, the frequency of which the present invention is designed to reduce, include, but are not limited to wherein the defect is VATER/VACTERL association (vertebral [defects], [imperforate] anus, tracheoesophageal [fistula], radial and renal [dysplasia])rachischisis (aka spinal dysraphism) such as spina bifida (including, but not limited to spina bifida aperta (aka spinabifida cystica); spinabifida occulta; and occult spinal disorder, among others) and (b) craniorachischisis (aka cranial dysraphism) such as cranium bifida (aka encephalocele or craniocele) each of spina bifida and cranium bifida being of any of the following types meningocele, myelomeningocele, lipomeningocele, and lipomyelomeningocele among others; (c) anencephaly; and (d) chiari malformation types 0,12,3; (2) caudal regression syndrome, caudal dysplasia sequence, congenitalsacral agenesis; sironmelia(mermaid syndrome), sacral regression and the like; (3) cranio-facial defects such as, without limitation, facial cleft (aka prosopoanoschisis, including without limitation cleft palate, cleft lip, velopharyngeal malformation (including without limitation bifid uvula, etc.); (4) anorectal malformations including, but not limited to (a) imperforate anus, (b) rectoperineal fistula, (c) recto-bladder neck fistula; (d) persistent urogenital sinus, (e) persistent cloaca, etc.; (5) bucket-handle malformation; among others. Biemond syndrome, Chiari malformation, (0,1,2,3), Ectrodactyly-ectoderma dysplasia, cleft lip/palate, Ellis Van Creveld syndrome, Muir-Torre syndrome, Cowden syndrome, Carney complex, Birt-Hogg-Dubé syndrome, Gorlin syndrome (ptc loss-of-function), Gorlin-Goltz syndrome, basal cell nevus syndrome, bifid-rib basal-cell nevus syndrome, basal cell cancer syndrome(shh gain of function), and multiple basal cell nevi, squamous cell carcinoma (increased ptc activity) Meckel Gruger syndrome, McKusick-Kaufman syndrome, Mirror hand deformity(ulnar dimelia) Mohr syndrome, Oral-facial-digital syndrome, Pallister Hall syndrome, cephalopolysyndactyly, Post axial polydactyly, GreigRubinstein-Taybi syndrome, retinoblastoma, Cardiofaciocutaneous syndrome, Noonan syndrome, short rib polydactyly, extra deformed fingers and toes, Lowe syndrome including ocular and renal defects, Renal Colombo syndrome, retinoblastoma, retinitis pigmentosa, holoprosencephaly, macular degeneration (whether it be due to a Shh defects, age, or secondary conditions like diabetes mellitus), mental retardation. All of these terms are well known in the art. However, for rapid reference, those unfamiliar with these terms are referred (without limitation to the Merck Manual, Eighteenth Edition 2006 and the PUR Medical Dictionary, Second Edition, 2000. The ultimate cause of these conditions can be genetic or environmental, or both. Nonetheless, it is also postulated here that certain cancers, and possibly even breast cancer in offspring are the result of signaling defects in utero and should be considered a birth defect as well since the results of the signaling defects in utero may not present until much later in life similar to that of other cancers when DNA damage and mutations accumulate postnatally. For example, our research suggests that in the microenvironment of mammary breast architecture comprise a population of epithelial cells and stem cells that continue to communicate post natally through converged signaling pathways. These mammary epithelial cells have the ability for self-renewal and harbor tumorigenic potential. Subsequent alterations in postnatal signaling mechanisms can result in a breast cancer as subsequent mammary development proceeds postnatally. Further studies also suggest that the stem-like, self-renewing cells originate from the progenitor fetal cells during early embryonic mammary development. These breast cancer stem cells have been identified as $CD44^+CD24^-$ breast tumor cells. In certain mouse mammary experimental models stem/progenitor cells displayed sensitivity to altered or hyper states of signaling pathways and new mapping techniques have demonstrated that a population of adult neural stem cells that rarely divides responded to normal or hyperactive Shh signaling even though adult neural stem cells rarely divide. All of this could result in unintended consequences in the formation of new malignancies. Nature 437, 894-897(6 Oct. 2005). We propose to correct signaling defects in utero with the method compound and/or its derivatives to prevent breast cancer.

Without being bound to theory, the inventor believes that all of these conditions are related to failure of proper embryonic patterning (mapping sequences) during the critical embryonic first trimester. One embryonic patterning sequence that has been identified is the Sonic hedgehog (Shh) gene and some inositol phosphates (and kinases therefore) (PI3K) have been shown to be important in the proper expression of the Shh gene. It is the present inventor's belief that these two signaling pathways converge in order for sufficient gene expression to occur. Mutations in the human shh gene and genes that encode its downstream intracellular signaling pathway causes many clinical disorders including, bur no way limited to basal cell carcinoma, nevoid basal cell carcinoma syndromes along with distinct congential syndromes syndromes as described above. Thus, insufficient D-chiroinositol levels (and/or phosphates (P, PP and/or polyP) thereof) interfere with or prevent the proper expression of the Shh gene and the result thereof is improper signaling of proper mapping of the embryonic tissue. Thus, proper supplementation with the D-chiroinositol compound will restore proper signaling and mapping, second messenger systems involved in embryonic patterning at that critical period, especially, if the embryo is one at risk of such improper signaling and mapping) so as to substantially reduce and/or eliminate the risk of the presentation of the above fetal malformations. Since the risk of some of the above conditions have been shown (but not statistically significant) to benefit from folate supplementation, co-therapy with both D-chiroinositol (and/or its phosphorylated (P, PP and/or polyP) derivatives) and folic acid (and/or another folate source) is the preferred embodiment of the invention. It is also believed that the D-chiroinositol (plus one of its phosphorylated (P, PP and/or polyP) derivatives) is the natural active agent involved in this mechanism and that either other forms like myo-inositol have a weak (or weaker) effect alone. It is further believed that a significant number of the women having children with these malformations have (a) insufficient inositol intake and therefore cannot convert a sufficient amount to the D-chiro form or (b) simply cannot properly convert other inositol forms to the D-chiro variety and/or to the proper phosphorylated variety via phosphoinositides. In this subpopulation, supplementation with any of the D-chiroinositol and/or its phosphorylated derivatives will serve equally well. A small subpopulation however may have defects in the various kinases (for example, PKA or PKC isoforms) involved and thus, the best supplementation would be with the particular phosphorylate that is after the kinase defect. Since finding the specific defect in a particular kinase may not be easily identified in all cases, a separate embodiment of the present invention is to use a mixture of D-chiroinositol and a number of its phosphorylated (P, PP and/or polyP) derivatives so as to be sure that none of the advantages of the present invention are missed in as many patients as possible. A highly preferred embodiment in this case is to use a mixture of D-chiroinositol and at least one member selected from D-chiroinositol-Phosphates$_{(1-8)}$. (In D-chiroinositol-Phosphates$_{(2-8)}$, one or more of the phosphates may be in the form of pyrophosphates, and in D-chiroinositol-Phosphates$_{(7-8)}$ at least one of the phosphates must be present as a pyrophosphate as there are only 6 positions which can be monophosphorylated).

Another aspect of the present invention relates to a method of modulating a differentiated state, survival, and/or proliferation of a cell, such as a normal cell or a cell having a ptc loss-of-function, hedgehog gain-of-function, or smoothened gain-of-function, or by an aberrant PI3K signaling pathway by contacting the cells with a compound as set forth above according to the subject method and as the circumstances may warrant as a way to target, manipulate, to optimize control of this pathway thereby mitigating its contribution to oncogenic and embryonic patterning activity.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue". Fibroblasts can be stimulated Myo-ip6-$SO_4$ (Stabilizers for fibroblast growth factors, Middaugh et al, U.S. Pat. No. 5,348,941) and play a critical role in wound healing. Transplanted fibroblasts can often retain positional memory of the location and tissue context where they had previously resided, at least over a few generations. Thus, the present invention finds utility in joints, hip, knee, cell, and tissue replacement. In one embodiment, embedding a fibroblast with the compound D-chiro-Ip6-$SO_4$ in a depot formulation, into the surgical site to help wound healing will promote the wound healing, especially in an elderly population that does not heal well due to age or people with diabetes mellitus, or immune system problems etc.

For instance, it is contemplated by the invention that, in light of the findings of an apparently broad involvement of PI3K and hedgehog, ptc, and smoothened in the formation of ordered spatial arrangements of differentiated tissues in vertebrates, the subject method is suitable for use as part of a process for generating and/or maintaining an array of different vertebrate tissue both in vitro and in vivo. The compound, whether inductive or anti-inductive with respect proliferation or differentiation of a given tissue, can be, as appropriate, any of the preparations described above.

For example, the present method of using subject compounds is applicable to cell culture techniques wherein it is desirable to control the proliferation or differentiation of the cell. A subject compound may be employed in a method directed towards cells which have a ptc loss-of-function, hedgehog gain-of-function, or smoothened gain-of-function phenotype, in vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be affected by contact with compounds of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a subject compound.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacts which is found to be degenerated in Parkinson's Disease patients.

Human heterologous neural progenitor cells may be derived from fetal tissue obtained from elective abortion, or from a post-natal, juvenile or organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of total cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2-}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6-8, more preferably close to pH 7, even more particularly about pH 7.4. Oils should be cultured at a temperature close to physiological temperature, preferably between 30° C.-40° C., more preferably between 32° C.-38° C., and most preferably between 35° C.-37° C.

Cells can be grown in suspension or on a fixed substrate, but proliferation of the progenitors is preferably done in suspension to generate large numbers of cells by formation of "neurospheres" (see, for example, Reynolds et al. (1992) Science 255:1070-1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 34 days in a 37° C. incubator, and proliferation can be reinitiated at any time alter that by dissociation of the cells and resuspension in fresh medium containing growth factors.

In the absence of substrate, cells lift off the floor of the flask and continue to proliferate in suspension forming a hollow sphere of undifferentiated cells. After approximately 3-10 days in vitro, the proliferating clusters (neurospheres) are fed every 2-7 days, and more particularly every 2-4 days by gentle centrifugation and resuspension in medium containing growth factor.

After 6-7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a subject compound.

To further illustrate other uses of the subject compounds, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) J Exp Biol 123:265-289; and Freund et al. (1985) J Neurosci 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of compounds employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into Glial cells, Schwann cells, Chromaffin cells, Cholinergic sympathetic or parasympathetic neurons, as well as peptidergic and serotonergic neurons. The subject compounds can be used alone, or can be used in combination with other neurotrophic factors which act to more particularly enhance a particular differentiation fate of the neuronal progenitor cell.

In addition to the implantation of cells cultured in the presence of the subject compounds, yet another aspect of the present invention concerns the therapeutic application of a subject compound to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject compounds can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury, (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubulated by use of a prosthetic device, subject compounds can be added to the prosthetic device to regulate the rate of growth and regeneration of the dendritic processes. Exemplary nerve guidance channels are described in U.S. Pat. Nos. 5,092,871 and 4,955,892, incorporated herein by reference.

In another embodiment, the subject method can be used in the treatment of neoplastic or hyperplastic transformations such as may occur in the central nervous system. For instance, the subject compounds can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas, etc. In this connection, the invention still further relates to inducing antiangiogenesis in localized or distant metastasized tumors by affecting cancer related vascular cells.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNETs may arise in other areas of the brain including the pineal gland (pineoblastoma) and cerebrum. Those arising in the supratentorial region generally fare worse than their PF counterparts.

Medulloblastoma/PNETs are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. Of the CHOP series of 51 children reported with ependymomas, not all are malignant and approximately ⅔ arise from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the an that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the subject compounds can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm of the mesoderm, which is critical to gut morphogenesis. Therefore, for example, compounds of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of subject compounds can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising subject compounds can be utilized in liver repair subsequent to a partial hepatectomy.

The generation of the pancreas and small intestine from the embryonic gut depends on intercellular signaling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) Curr Biol 7:801-4. The Shh gene is expressed throughout the embryonic gut endoderm with the exception of the pancreatic bud endoderm, which instead expresses high levels of the homeodomain protein Ipfl/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialized mesoderm derivatives of the small intestine and pancreas. To test this, they used the promoter of the Ipfl/Pdx1 gene to selectively express Shh in the developing pancreatic epithelium. In Ipfl/Pdx1-Shh transgenic mice, the pancreatic mesoderm developed into smooth muscle and interstitial cells of Cajal, characteristic of the intestine, rather than into pancreatic mesenchyme and spleen. Also, pancreatic explains exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject compounds can be used to control or regulate the proliferation and/or differentiation of pancreatic tissue and intestinal tissue (see distal hindgut deformation discussed elsewhere within the present specification) both in vivo and in vitro.

There are a wide variety of pathological cell proliferative and differentiative conditions for which the inhibitors of the present invention may provide therapeutic benefits, with the general strategy being, for example, the correction of abberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method is suitable for use as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of .beta.-cells or decreased islet cell mass. To the extent that one more of aberrant PI3K/hedgehog, ptc, smoothened signaling may be indicated in disease progression, the subject regulators can be used to enhance regeneration of the tissue after anti-tumor therapy.

Moreover, manipulation of PI3K/hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultural tissue. In an exemplary embodiment, the subject method can be used to augment production of prosthetic devices which require β-islet cells, such as may be used in the encapsulation devices described in, for example, Aebischer et al. U.S. Pat. No. 4,892,538, Aebischer et al. U.S. Pat. No. 5,106,627; Lira U.S. Pat. No. 4,391,909, the Sefton U.S. Pat. No. 4,353,888, all incorporated herein by reference. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature .beta.-cells can be observed. By utilizing the subject compounds, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al. (1997) Development 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) Biochem Biophys Res Commun 238:658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Numerous other tumors may (based on evidence such as involvement of the hedgehog pathway in these tumors, or detected expression of hedgehog or its receptor in these tissues during development) be affected by treatment with the subject compounds. Such tumors include, but are by no means limited to, tumors related to Gorlin's syndrome (e.g., basal cell carcinoma, medulloblastoma, meningioma, etc.), tumors evidenced in pet knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising one or more of the subject compounds can be used in the in vitro generation of skeletal tissue, such as from skeletogenic stem cells, as well as the in vivo treatment of skeletal tissue deficiencies. The present invention particularly contemplates the use of subject compounds to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For example, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, alignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a subject compound to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject regulators may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) Clin Orthop Relat Red 252:129), isolated chondrocytes (Grande et al. (1989) J Orthop Res 7:208; and Takigawa et al. (1987) Bone Miner 2:449), and chondrocytes attached to natural or synthetic polymers (Walitani et al. (1989) J Bone Jt Surg 71B:74; Vacanti et al. (1991) Plast Reconstr Surg 88:753; von Schroeder et al. (1991) J Biomed Mater Res 25:329; Freed et al. (1993) J Biomed Mater Res 27:11; and the Vacanti et al. U.S. Pat. No. 5.041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a subject compound during certain stages of the culturing process in order to manage the rate of differentiation of chondrocytes and the formation of hypertrophic chrondrocytes in the culture.

In another embodiment, the implanted device is treated with a subject compound in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient Indian hedgehog is particularly associated with the hypertrophic chondrocytes that are ultimately replaced by osteoblasts. For instance, administration of a compound of the present invention can be employed as part of a method for regulating the rate of bone loss in a subject. For example, preparations comprising subject compounds can be employed, for example, to control endochondral ossification in the formation of a "model" for ossification.

In yet another embodiment of the present invention, a subject compound can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Azospermic and oligospermic males are viable but infertile, owing to a complete absence of mature sperm. Examination of the developing testis in different genetic backgrounds suggests that Dhh regulates both early and late stages of spermatogenesis. Bitgood et al. (1996) Curr Biol 6:298. In a preferred embodiment, the subject compound can be used as a contraceptive. In a similar fashion, compounds of the subject method are potentially useful for modulating abnormal ovarian function, and at the same time, offering protective effects against the use of ovulation inductors for treating infertility in phenotypes with receptor loss of function (non-limiting drug list incorporated herein).

In yet another embodiment of the present invention, a subject compound can be used to regulate ovulation as describe in the proceeding paragraph. The hedgehog proteins, particularly Dhh, have been shown to be involved induced expression of the hedgehog target genes Ptch1 and Gli1, in the surrounding pre-theca cell compartment. Cyclopamine, a highly specific hedgehog signaling antagonist, inhibits this induced expression of target genes in cultured neonatal mouse ovaries. The theca cell compartment remains a target of hedgehog signaling throughout follicle development, showing induced expression of the hedgehog target genes Ptch1, Ptch2, Hip1, and Gli1. In periovulatory follicles, a dynamic synchrony between loss of hedgehog expression and loss of induced target gene expression is observed. Oocytes are unable to respond to hedgehog because they lack expression of the essential signal transducer Smo (smoothened). The present results point to a prominent role of hedgehog signaling in the communication between granulosa cells and developing theca cells (Endocrinology Vol. 146, No. 8 3558-3566, 2005).

The subject method also has wide applicability to the treatment or prophylaxis of disorders afflicting epithelial tissue, as well as in cosmetic uses. In general, the method can be characterized as including a step of administering to an animal an amount of a subject compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts) when used together with the method of the present invention. (See the earlier discussion concerning fibroblasts and wound healing above.)

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The subject method can also be used in the treatment of corneopathies marked by corneal epithelial cell proliferation, as for example in ocular epithelial disorders such as epithelial downgrowth or squamous cell carcinomas of the ocular surface. Also, for example, the subject method and compounds can be used to treat degenerative diseases of the retina.

Levine et al. (1997) J Neurosci 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) Development 124:363 demonstrated that treatment of cultures of perinatal mouse retinal cells with the amino-terminal fragment of Sonic hedgehog results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation. Furthermore, Bennett, Jeffrey L. Journal of Neuro-Ophthalmology: Volume 22(4) December 2002 pp 286-296 cites recent studies that have identified several factors important for the determination and function of the optic disc: sonic hedgehog (Shh), Pax Gli3 transcription factors. Deficient Shh expression in zebrafish leads to cyclopia, whereas ectopic expression results in small optic cups and enlarged optic stalks. Pax2 null mutant mice fail to form optic discs, resulting in medial extension of retinal pigment epithelial cells into the optic stalk, failure of axons to cross at the optic chiasm, and optic nerve coloboma. The murine Gli3 mutant, 'extra-toes,' also has optic nerve coloboma). Mutations in the human Shh and Pax2 genes are known to result in holoprosencephaly and the renal-coloboma syndrome, and possibly retinoblastoma. Retinitis Pigmentosa is a photoreceptor degenerative disease leading to blindness in adulthood. Ala Moshiri et al. The Journal of Neuroscience, Jan. 7, 2004, 24(1):229-237; doi: 10.1523/JNEUROSCI2980-03.2004 also postulates that the hedgehog signaling pathway is a key regulator of neural development, affecting both proliferation and differentiation of neural progenitors. Sonic hedgehog (Shh) is a mitogenic factor for retinal progenitors in vitro. They wanted to determine whether this signaling system is important in vivo for regulating retinal progenitor proliferation, they analyzed mice with a single functional allele of the Shh receptor patched (ptc). They found that ptc+/− mice had increased numbers of neural progenitors at every stage of retinal development that they examined. In addition, these mice had persistent progenitors at the retinal margin for up to 3 months of age, reminiscent of the ciliary marginal zone of lower vertebrates. To test whether the progenitors at the retinal margin of ptc+/− mice could be induced to regenerate retinal neurons in response to damage, they bred ptc+/− mice onto a retinal degeneration background (pro23his rhodopsin transgenic) and labeled newly generated cells with combined immunohistochemistry for bromodeoxyuridine and retinal neuron and photoreceptor-specific markers. Ala Moshiri et al. (2004) found newly generated neurons and photoreceptors at the retinal margin in ptc+/−; pro23his mice. They propose that the Shh pathway may act as a regulator of both prenatal and postnatal retinal growth. Through the use of the subject method and compounds, there is hope in treating diseases associated with degeneration of the photoreceptors and for treating other childhood cancers like retinoblastoma related to deficiencies in Shh pathways.

The subject method and compositions can also be used to treat wounds resulting from dermatological diseases, such as lesions resulting from autoimmune disorders such as psoriasis. Atopic dermatitis refers to skin trauma resulting from allergies associated with an immune response caused by allergens such as pollens, foods, dander, insect venoms and plant toxins.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

Yet another aspect of the present invention relates to the use of the subject method to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages; anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The subject method can also provide a process for extending the duration of depilation.

Moreover, because a subject compound will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, subject compounds can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulerythematosa reticulata or keloid folliculitis. For example, a cosmetic preparation of a subject compound can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatoiogical diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a subject compound, e.g., which promotes quiescense or differentiation, can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a subject compound composition in amounts sufficient to inhibit hyperproliferation of epidermal/epidermoid cells of the lesion.

Acne represents yet another dermatologic ailment which may be treated by the subject method. Acne vulgaris, for instance, is a multi factorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative subject compound, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the subject method are disorders specific to non-humans, such as mange as well as any of the disease states or conditions occurring in animals corresponding to the conditions and disease states in humans described above or below.

In still another embodiment, the subject method can be used in the treatment of human cancers, particularly basal cell carcinomas and other tumors of epithelial tissues such as the skin. For example, subject compounds can be employed, in the subject method, as part, of a treatment for basal cell nevus syndrome (BCNS), and other human carcinomas, adenocarcinomas, sarcomas and the like.

In a preferred embodiment, the subject method is used as part of a treatment of prophylaxis regimen for treating (or preventing) basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five U V-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al. (1997) Science 277:1109-13; Xie et al. (1997) Cancer Res 57:2369-72; Oro et al. (1997) Science 276:817-21; Xie et al. (1997) Genes Chromosomes Cancer 18:305-9; Stone et al. (1996) Nature 384:129-34; and Johnson et al. (1996) Science 272:1668-71.

The subject method can also be used to treat patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients. Studies of BCNS patients show that they have both genomic and sporadic, mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

In certain embodiments, the invention compound can be chosen on the basis of selectivity for the hedgehog pathway. This selectivity can be for the hedgehog pathway vs other mediated pathways that are used with the compound as well as selectivity for particular hedgehog pathways, e.g., which isotype specific for hedgehog (e.g., Shh, Ihh, Dhh) or the patched receptor (e.g., ptc-1, ptc-2). For instance, the subject method may employ different compounds with different phosphates which do not interfere with the biological activity of compounds used in birth control, chemotherapeutic agents, or other ablative therapies (without limitation incorporated herein): Aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-.alpha., estradiol-17-.beta., estriol, estrane, estrone, hydrocortisone, lanosterol, lithocholic acid, mestranol, .beta.-methasone, prednisone, pregnane, pregnenolone, progesterone, spironolactone (as used in Lybrel®), testosterone, triamcinolone and their derivatives.

In this manner, untoward side effects which may be associated with certain members of these steroidal alkaloids, cancer therapeutics, and other class of drugs described above and incorporated herein can be reduced by using the D-chiroinositol compound. For example, some methods and compositions may be employed as a means of reducing such unwanted negative side effects to certain drug regimes during chemotherapy or infertility treatments. These side effects include hirsuitism (excess hair growth due to hormones), shortened life spans, cardiovascular diseases (with the use chemotherapeutic agents like tamoxifen and herceptin) and vascular occlusion (stroke risk with hormonal/birthcontrol use), organ toxicity, hyperglycemia and diabetes exacerbation (with hormonal/birthcontrol use), steroidal glaucoma, hypertension (from birth control use or hormone use), and increased susceptibility to infections (from steroid akaloids and chemotherapeutics agents) or other types of cancers. In this manner, unwanted side effects which may be associated with certain members of steroidal aklyloids can be reduced with the method compounds. For example, using the drug screening assays described herein, and the application of combinationatorial and medicinal chemistry techniques, provides a means for identification of individual agents best suited for reducing the unwanted negative side effects of other actives that is part of this application.

Dosages of $C_{19}H_{19}N_7O_4$ can vary from about 100 µg to about 2 mg per day, preferably at least about 200 µg per day, more preferably at least 400 µg per day and should preferably be no more than about 1.6 mg per day, more preferably not more than about 1.2 mg per day. Specific pre-natal dosages of folic add are well known and any of the literature dosages of this component will be suitable, especially 0.4 mg, 0.6 mg, 0.8 mg, 1.0 mg, 1.2 mg, and 1.4 mg for example. Other folate sources beyond $C_{19}H_{19}N_2O$ can be used with or instead of $C_{19}H_{19}N_7O_6$ in amounts that appropriate to result in the same delivery as the aforementioned folic acid. Combinations of $C_{19}H_{19}N_7O_6$ and other folate sources are administered in appropriate amounts so that the total is equivalent to a $C_{19}H_{19}N_7O_6$ dose within the above limitations.

D-Chiroinositol doses (and the various derivatives thereof calculated on the basis of unphosphorylated D-chiroinositol) range from about 0.05 mg/day to about 60 grams per day, preferably about 0.05 mg/day to about 30 grams per day, preferably about 0.1 mg to about 25 grams/day, more preferably, about 1 mg to about 20 grams/day, still more preferably about 5 mg to about 10 grams per day, even more preferably about 10 mg to about 5 grams per day, yet more preferably about 25 mg to about 2 grams/day, still even more preferably about 20 mg to about 1.8 grams/day. Highly preferred dosages of D-chiroinositol (and its P, PP, and PolyP derivatives) further include, about 10 mg/kg/day to about 500 mg/kg/day; about 100 mg to about 1 gram/day; about 1.2 gram to about 1.8 gram/day; about 500 mg/day; about 500 to about 700 mg/day; about 25 mg/kg/day to about 100 mg/kg/day. Particular daily doses (based on unphosphorylated D-chiroinositol) include: about 0.1 mg, about 0.2 mg, about 0.5 mg, about 0.8 mg, about 1 mg, about 1.25 mg, about 1.5 mg, about 2 mg, about 2.5 mg, about 3 mg, about 5 mg, about 10 mg, about 12.5 mg, about 15 mg, about 20 mg, about 25 mg, about 40 mg, about 50 mg, about 75 mg, about 100 mg, about 125 mg, about 150 mg, about 200 mg, about 250 mg, about 300 mg, about 350 mg, about 400 mg, about 500 mg, about 750 mg, about 800 mg, about 1 g, about 1.2 g, about 1.4 g, about 1.6 g, about 1.8 g, about 2 g, about 2.4 g, about 2.5 g, about 2.75 g, about 3 g, about 3.5 g, about 4 g, about 5 g, about 6 g, about 8 g, about 10 g, about 12 g, about 15 g, about 18 g, about 20 g, about 22.5 g, about 25 g, about 30 g, about 40 g, about 50 g and about 60 g. These, particularly the larger doses, may be administered in fractional doses, all at a single time or spread out over the day as may be convenient.

In another aspect, the present invention provides pharmaceutical preparations comprising the subject compounds. The compounds for use in the subject method may be conveniently formulated for administration with a biologically acceptable and/or sterile medium, such as water, buffered saline, polyol (for example, glycerol, propylene glycol, liquid polyethylene glycol and the like) or suitable mixtures thereof. The optimum concentration of the active ingredient (s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the subject compounds, its use in the pharmaceutical preparation of the invention is contemplated. Suitable vehicles and their formulation inclusive of other proteins are described, for example, in Remington's Pharmaceutical Sciences (Mack Publishing Company, Easton, Pa., USA 1985). These vehicles include injectable "deposit formulations".

The composition which is applicable to all aspects of the present invention is provided in various forms and formulations, and includes without limitation, as an implant, a topical and transdermal formulation, as a slow release formulation, as an inhalable and vaporizable composition, and in injectable form among others. The composition may be part of a kit, along with instructions for the administration of the therapeutic agent, and optionally syringe(s) and needles, an inhalant device, a transdermal device, and the like.

In addition to forms set out earlier, the agent may be administered in the form of a solid, such as tablets, dragees, capsules, powders, suppositories, etc., and as a solution, suspension, or emulsion in a carrier. Particularly desirable are formulations for systemic and topical administration, e.g., oral, injectable, topical, transdermal, including those for iontophoretical delivery, implantable, and vaginal, rectal, intranasal, intrapulmonary, and other types of formulations, which may be prepared by methods known in the art. Solid and liquid carriers are suitable, and are known in the art. Liquid carriers typically used in preparing solutions, suspensions, and emulsions, which are contemplated for use in the practice of the present invention include water, salt solutions, such as saline, pharmaceutically acceptable organic solvent(s) and their mixtures, pharmaceutically acceptable oils or fats, and mixtures of any and all of the above. The carrier may contain other therapeutic agents and suitable pharmaceutically acceptable additives such as solubilizers, emulsifiers, nutrients, buffers, preservatives, suspending agents, thickening agents, viscosity regulators, and stabilizers, among others. Suitable organic solvents include, for example, monohydric alcohols, such as ethanol, and polyhydric alcohols, such as glycols. Suitable oils include, for example, soybean oil, coconut oil, olive oil, saffflower oil, cottonseed oil, and the like. For parenteral administration, the carrier may also be an oily ester such as ethyl oleate, isopropyl myristate, and the like. Other pharmaceutically acceptable forms include microparticles, microcapsules, liposomal encapsulates, and the like, as well as their combinations of the agent of the invention, alone or with one or more other therapeutic agents may be formulated into sustained release microparticles or microcapsules. Materials suitable for the microparticle matrix include materials such as starch, polyvinyl alcohol, polyvinylpyrrolidinone, polyacrylic acid, and the like, as well as combinations of any two or more thereof. Biodegradable polymers suitable for use as a microparticle or microcapsule matrix include, without limitation, for example, poly-1-lactide, poly-dl-lactide, polyglycolide, poly(glycolide-co-dl-lactide), polyanhydrides, polyorthoesters, poly(alpha-hydroxybutyric acid), poly-p-dioxinone, and block polymers of polyglycolide, trimethylene carbonate, polyethylene oxide, proteins, polysaccharides, and derivatives and mixtures thereof. The microparticles and microcapsules containing the agent may be prepared employing methods which are well known in the art, e.g., by solvent evaporation, phase separation, and interphase reaction methods, spray drying, physical methods, and the like. As already indicated, the present agent may also be encapsulated into liposomes, and the microparticles, microcapsules, and/or liposomes loaded with the agent may then be suspended or emulsified in a suitable liquid carrier.

In addition to the manners set forth above, any aspect of the present agent may be administered in a variety of ways, including topical, enteral, and parenteral routes of administration. For example, without limitation, suitable modes of administration include subcutaneous, transdermal, transmucosal, including iontophoretic, intravenous, subcutaneous, transnasal, intrapulmonary, transdermal, oral, rectal, vaginal, implantable and the like, as well as their combinations. The particular pharmaceutically acceptable form of the therapeutic agent employed will depend on the route of administration selected. The agent may be, for example, administered in a form that enhances its bioavailability when compared with standard oral formulations. Suitable forms include a lipid carrier system that promotes the oral absorption of compounds through the intestinal epithelium. Examples of these systems are oil-in-water, and water-in-oil emulsions. Exemplary oils that are contemplated for use in oil-in-water and water-in-oil based systems include castor oil, olive oil, soybean oil, safflower oil, coconut oil, cottonseed oil, their combinations, and the like. Other suitable forms that enhance the bioavailability of the orally administered agent of this invention include single surfactant, and mixed micelle systems. The agent may, for example, be orally administered in the form of a mixed micelle system containing linoleic acid- and polyoxyethylene-hardened castor oil. Suitable surfactants contemplated for use in single and mixed micelle systems include polyoxyethylene ether, polyoxypropylene ether, polyoxyethylene lauryl, cetyl and cholesteryl ethers, polyoxyethylene derivatives of lanolin alcohols, and the like, as well as their mixtures.

When intravenous or subcutaneous administration is contemplated, the use of a solution of the therapeutic agent is preferred. For transdermal administration by iontophoresis, the agent is preferably administered in charged form, such as in the form of a salt. The salt may be in solution or in a gel reservoir. Therapeutic agent-containing gels may be used as a drug reservoir for many routes of administration. An agent containing gel may be prepared by blending the inositol based compound with a hydrogel-forming polymer such as polyvinyl alcohol, polyacrylamides, copolymers of propylene oxide and ethylene oxide. e.g., Pluronic.®., polyvinylpyrrolidinone, gelatin, polymers and copolymers of maleic anhydride, polyacrylic acid and salts and derivatives thereof, polysaccharides, and salts and derivatives thereof, cellulosic polymers, and salts and derivatives thereof, polycarboxylic acids, and the like, as well as their mixtures. The agent may also be administered transdermally through the use of a skin patch, with a carrier. Suitable carriers are typically inert to the agent, non toxic to the skin, and allow the delivery of the agent for systemic absorption into the blood stream via the skin. Carriers for transdermal absorption may include pastes, such as absorptive powders dispersed in petroleum or hydrophilic petroleum with the agent, with or without a carrier, or a matrix containing inositol. Preparations of agent-based compounds may also be administered topically as a solution, cream, lotion, or gel, formulated with pharmaceutically acceptable vehicles containing the agent. The agent may also be administered intra or transnasally or intrapulmonarily as an aerosol spray of a solution, suspension or emulsion, or as microparticles, microcapsules, or liposomes containing the agent. Also contemplated are formulations of the agent of this invention with pharmaceutically acceptable excipients. Suitable excipients contemplated for use as processing aids and drug delivery modifiers and enhancers include calcium phosphate, magnesium stearate, talc, monosaccharides, disaccharides, starch, gelatin, cellulose, methyl cellulose, sodium carboxymethyl cellulose, dextrose, polyvinylpyrrolidinone, low melting waxes, ion exchange resins, and the like, as well as their combinations. Typically, such formulations are prepared as tablets or capsules. Other formulations are, however, also within those contemplated in this patent.

The agent may be administered as a single dose or in multiple doses. Multiple doses may be administered either continuously, in intervals, or a combination of both. The agent, for example, may be administered as a single dose, optionally coupled with a follow-up dose. The follow-up dose may be administered by the same or different route of administration as a single or sustained dose. Accordingly, the present composition is presented in unit dosage form or in multiple dosage form, as well as in the form of a kit, which may be for self administration, along with instructions for the use of the therapeutic agent, and optionally a syringe(s) and needle(s), an inhaler or vaporizer, a transdermal patch, optionally for iontophoresis, and the like. The composition is also provided as a cream or gel for topical application, and as an implant. The manufacture of implants is known in the art and commercially available.

One particular form of implantable version of the present invention is the use of a dendrimeric type of carrier, which may have the inositol based compound attached thereto by an ionic, covalent, or hydrogen bonding. Alternatively, the inositol component of the invention bound to a fibroblast bound dendrimer (which fibroblast will anchor the delivery system in place) is also contemplated. Dendritic molecules have multiple protrusions which may also be used to attach the dendrimer to a particular site within the body, to particular cells, or can be implanted for migration within the body for attachment to particular cites at some other point in time. (See for example Dendrimers Improve Cancer Drug Uptake and Antitumor Activity, Drug Delivery, Boston University, NCI Alliance for Nanotechnology in Cancer— NanoTechWire_com—The online resource for Nano Technology And Research, Jan. 15, 2007 available at http://nanotechwire.com/news.asp?nid=4213. Alternatively, the protrusions themselves may have the inositol component bound thereto or coated thereon.

Another implantable version is the use of nanobots or nanorobots for the delivery of the active agent. While nanorobotics is a rather recent development, those of ordinary skill will appreciate the advantages of such a delivery, which can be achieved in manners set forth in for example (a) Shanthi, et al; Prospects for medical Robots; AZojono Journal of Nanotechnology Online, posted 13 Nov. 2007; http://www.azonano.com/Details.asp7ArticleID=2035; (b) Adriano Cavalcanti, Bijan Shirinzadeh, Tad Hogg, Julian A. Smith, "Hardware Architecture for Nanorobot Application in Cancer Therapy", IEEB-RAS ICAR Int'l Conf. on Advanced Robotics, Jeju, Korea, pp. 200-205, August 2007; (c) Hede et al, "Nano": the new nemesis of Cancer, J Can Res Ther [serial online] 2006 [cited 2007 Dec. 11], 2:186-195 available from http://www.cancerjournal.net/text.asp?2006/2/4/186/29829 and (d) Nanorobotics Control Design and 3D Simulation, available at http://www.nanorobotdesign.com/(2007). A preferred version of the nanorobotic delivery in the present invention is designed to be implanted in or around the site of specific delivery such as a cancerous lesion excision site or into an inoperable tumor and which delivers the active agent or active agent precursor on a single prolonged or multiple release schedule which can be pre-programmed for delivery over short or extended periods extending for as much as multiple years. As may be desired, the nanorobotic delivery system can be one which can migrate or be fixed in position by virtue of specific adherence mechanisms including fibroblasts, monoclonal antibodies, charged particle portions, antisence DNA, etc.

Yet another implantable or injectable and migratable delivery system utilizes monoclonal antibodies that are specific to cancer cell receptors or other cancer cell specific proteins. These antibodies having the active agent linked thereto migrate to the specific cancer cells and deliver the active agent directly to the cell on which it is to act.

Pharmaceutical formulations of the present invention can also include veterinary compositions, e.g., pharmaceutical preparations of the subject compounds suitable for veterinary uses, e.g., for the treatment of live stock or domestic animals, e.g., dogs.

Compositions of the present invention may be single active agent entities that are merely co-administered as described herein or fixed combinations as indicated above. The other components beyond the folic acid (and/or other folate) and the inositol compounds (and/or P, PP, and/or PolyP derivative thereof, and the other derivatives thereof discussed further herein) can be selected from a wide variety of compounds. Additional active agents that may be included in or merely co-administered with the above components include those estrogenic and progestogenic substances used in birth control pills, hormone replacement therapy, androgen ablative therapy, etc. (including, but not limited to conjugated estrogens, ethinyl estradiol, levonorgestrel, norgestrel, norgestimate, norethidrone, norethidrone acetate, mestranol, ethynodiol diacetate, norelgestromin, etonogestrel, desogestrel, etc). These hormones are currently marketed under the following (non-limiting) trade names: ALESSE, ANGELIQ, DIANE, LEVLEN, LO-OVRAL, LYBREL, TRICYCLEN, ORTHOCEPT, ORTHOEVRA, MIRENA, MENOSTAR, NUVA RING, OVRAL, TRI-LEVLEN, TRIPHASIL, BREVICON, FEMHRT, LOESTRIN, LoOGESTREL, MICROGESTIN, YAZMIN, among others. Where the birth control or hormone replacement therapy dosage form is other than an oral dosage form (such as, for example, a transdermal patch (in the case of currently marketed norelgestromin) or a vaginal ring (in the case of currently marketed etonogestrel estradiol), ORTHO-EVRA marketed as transdermal birthcontrol patch (recently linked to higher than average acute thromboembolitic events in female users). The invention compound is designed to eliminate the inherent risk of this type of hormonal contraception. Also transdermal patches for hormonal replacement including but not limited to Vivelle® and Vivelle-Dot™, Estradot®, combination estrogen/progestin transdermal delivery systems (including CombiPatch™, licensed to Aventis, and Estalis®, Testoderm®. The invention objectives are achieved with a co-therapy of a suitable dosage form with or without the folic acid (and/or other folate source) and D-chiroinositol (and/or P, PP, and/or Poly P derivatives thereof). Andogen ablative therapies for which the instant invention can be used include treatment with for example, without limitation, finasteride as well as other known androgen ablative drugs. Other active compounds for use in combination with or in cotherapy with the inositol compounds of the invention include, especially in the fetal alcohol syndrome prevention aspect, those used in cholesterol reduction regimens, especially the statins.

Compositions of the present invention in which the D-chiroinositol or other inositol component and or the folic acid component are the only active agents can be prepared as in or analogously to those set forth in the patents indicated above as being incorporated herein by reference. For compositions that are disclosed therein that have an inositol component, the D-chiroinositol or other inositol component (and/or P, PP, and/or PolyP derivative thereof or other derivative thereof discussed further herein) can be used in direct replacement of the such inositol component indicated in such reference. The folic acid (and/or other folate source) can be incorporated therein by merely replacing a small portion of filler or merely adding the folic acid (and/or other folate source) thereto. Where the referenced formulation is a folic acid formulation and the dose selected for the inositol (and/or P, PP, and/or PolyP derivative thereof or other derivative thereof discussed further herein) is sufficiently small, the inositol (and/or derivative thereof) can be used in place of a portion or all of the filler used in the referenced formulation, or added to it. If larger amounts are needed, then the filler used in the referenced formulation is replaced with the inositol (and/or P, PP, and/or PolyP derivative thereof or other derivative thereof) component if the resulting tablet size is not of concern. If the size of the dosage form is insufficient to accommodate the full dose of the inositol component, then either a separate dosage form is used or multiple dosage forms haring a fraction of the daily dose is used and the patient will need to take more than 1 dosage form to achieve the daily dosages set forth.

In preferred dosage forms of one embodiment of the invention, the D-chiroinositol (and/or P, PP, and/or PolyP derivatives thereof or other derivatives thereof) is substantially free of the other isomers of inositol. In highly preferred formulations of this embodiment, the D-chiroinositol (and/or the P, PP, and/or PolyP derivatives thereof or other derivatives thereof) and the dosage forms thereof are completely free of the other isomers of inositol as well as their corresponding phosphorylated derivatives. For purposes of the present invention, "substantially free" means not more than about 5% based on the combined D-chiro forms present, more preferably not more than about 2.5%, still more preferably not more than about 1%, most preferably not more than 0.5%. For purposes of the present invention, "completely free of" or "free of" means below the limit of detection of said non-D-chiro forms respectively in common analytical techniques used in common pharmaceutical quality control of bulk materials as of the date of the invention herein. Similarly with respect to formulations of other embodiments of the invention in which other inositol isomers, their respective phosphorylates (of varying size) or other derivatives thereof as described further herein, preferred am those that are substantially free of other isomeric forms of inositol than the one being primarily present, and more preferably completely free of such other isomeric forms.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

The therapeutic agent of this aspect of the invention (the non-D-chiroinositol based inositol compounds), is typically administered to a subject at a dose of about 20 to about 8,000 mg/kg/day, and preferably at about 30 to about 5,000 mg/kg/day. Other amounts, however, may also be administered. Higher or lower doses of these agents, however, may also be administered.

U.S. Pat. No. 5,998,485 (incorporated herein by reference) reports that unmodified scyllo inositol is more potent than other unmodified inositol isomers tested there in modulating a subject's immune response in a dose dependent manner. When the agent is administered at relatively low doses, it effectively enhances a mammal's immune response and, when administered at relatively high doses, inositol effectively inhibits or suppresses the mammal's immune response. Thus, the gain-of-function or loss-of-function activity of the inositols may vary depending on dose and the above screenings should be undertaken at multiple dosing schedules to determine whether an analogous result is present with respect to other inositol based compounds within the present invention, and if so, the compound may be used in the appropriate indication above at the appropriate dose NOTWITHSTANDING prior direction to not use any particular active agent in such indication.

The dose response range for gain-of-function as opposed to loss-of-function for any particular pathway may vary somewhat depending on the form of the agent employed, such as, the particular stereoisomer, derivative, or salt employed. One of ordinary skill in the art, however, may readily determine the range of response-enhancing doses of the therapeutic agent by the above screening tests and by other means known in the art, e.g., by generating a dose-response curve for any particular form of therapeutic agent. The dose of the therapeutic agent administered for any particular activity will, of course, also vary with factors such as the pharmacodynamic characteristics of the agent employed, its mode and route of administration, the age, health, and weight of the recipient, the nature and extent of the symptoms, the kind of concurrent treatments), the frequency of treatment, the effect desired, and the like. Modulation of the doses within the ranges set forth herein are within the skill of the ordinary skilled clinician and can be adjusted by such persons appropriately.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.00001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

Methods of introduction may also be provided by rechargeable or biodegradable devices. Various slow release polymeric devices have been developed and tested in vivo in recent years for the controlled delivery of drugs, including proteinacious biopharmaceuticals. A variety of polymers (including hydrogels), can be used to form an implant for the sustained release of a subject compound at a particular target site. Other methods of drug delivery may also be provided by nanotechnology utilizing such nanomaterials, nanostructures, nanofibers, nanowires, nanoparticles, quantum dot, nanotube, dendrimer, nanocystal, or nanobot. (See HIGH-PRESSURE POLYMERIZATION OF SINGLE WALL CARBON NANOTUBES; M. Popov, M. Kyotani find Y. Koga Joint Research Consortium of Frontier Carbon Technology, JFCC, c/o NIMC, Higashi, Tsukuba, Ibaraki, 305-8565, Japan and R. J. Nemanich Department of Physics, North Carolina State University, 408A Cox, Box 8202, Raleigh, NC, 27695-8202, USA; http://www.eng.auburn-.edu/department/ee/ADC-FCT2001/ADCFCT abstract/101.htm)

Other methods of entry may also be provided by a battery. For example, a battery operated transdermal drug delivery device (iontophoresis) utilizing a current distribution member for delivering a pulsed direct current sufficient to iontophoretically deliver composition across a stratum corneum layer of the epidermis. The current distribution member comprises an electrochemically active component in electrical connection with a battery, a voltage pulse generator and a precision resistor.

The preparations of the present invention may be given orally, parenterally, topically, or rectally. They are of course given by forms suitable for each administration route. For example, they are administered in tablets or capsule form, by implant, injection, inhalation, eye lotion, ointment, drops, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intrasystemically, and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

The term "treatment" is intended to encompass prophylaxis, therapy and cure, unless specifically indicated otherwise or the context requires otherwise.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutic effects of the first administered one is not entirely disappeared when the subsequent is administered.

III. Pharmaceutical Compositions

While it is possible for a compound of the present invention to be administered alone, it is preferable to administer the compound as a pharmaceutical formulation (composition). The subject compounds according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described herein, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue: (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect, e.g., with respect to D-chiroinositol and its derivatives by overcoming a ptc loss-of-function, hedgehog gain-of-function, or smoothened gain-of-function, in at least a sub-population of cells in an animal and thereby blocking the biological consequences of that pathway in the treated cells, at a reasonable benefit/risk ratio applicable to any medical treatment.

The phrase pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Such materials will be known to those of ordinary skill in the pharmaceutical formulation art.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject regulators from one organ, or portion of the body, to another organ, or portion of the body. Each carrier must be "acceptable" in the sense of being compatible with the other ingredients of the formulation and not injurious to the patient Some examples of materials which can serve as pharmaceutically acceptable carriers include without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable sails" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate. succinate, tartrate, naphthylate, mesylate, glucoheptonate, lactobionate, and laurylsulphonate salts and the like. (See, for example, Berge et al. (1977) "Pharmaceutical Salts", J. Pharm. Sci. 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

As described above, where the compounds used in the invention are capable of salt formation, the reference to the compound includes the pharmaceutically acceptable salts thereof. These salts can be prepared in situ during the final isolation and purification of the compounds of the invention, or by separately reacting a purified compound of the invention in its free form with a suitable organic or inorganic acid or base as appropriate, and isolating the salt thus formed, or reacting a salt of the compound with an appropriate organic or inorganic acid or base to result in a different salt formation. Representative pharmaceutically acceptable acid addition salts include, without limitation, the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", J. Pharm. Sci. 66:119).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, stearic acid, and talc, as well as coloring agents, release agents, coating agents, sweetening, flavoring and perfuming agents, preservatives and antioxidants am also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral or topical (including buccal and sublingual), rectal, vaginal, and/or parenteral, transdermal, iontophoresis, nano particle delivery (without limitation), and various polypeptide vectors "carrier" administration from one organ to another as necessary. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product. Alternative methods will be appreciated by those of ordinary skill in the pharmaceutical formulating art.

Formulations of the invention suitable for oral administration may be in the form of capsules, cachets, pills, tablets, lozenges (usually using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as, without limitation, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate: (8) absorbents, such as kaolin and bentonite clay, (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent, etc. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the subject compounds in the proper medium. Absorption enhancers can also be used to increase the flux of the compound across the skin. The rate of such flux can be controlled by either providing a rate controlling membrane or dispersing the compound in a polymer matrix or gel or microneedle technology. Battery operated transdermal drug delivery utilizing a current is another example of controlling rate of flux (Iontophoretic transdermal delivery)

Ophthalmic formulations, ophthalmalic eye implant for medication delivery, eye ointments, drug eluting contact lenses, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous earners which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial find antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline, or nanocrystal, or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in polymers such as, without limitation, polylactide-polyglycolide. Depending on the ratio of drug to polymer, and the nature of the particular polymer employed, the rate of drug release can be controlled. Examples of other polymers include poly (orthoesters) and poly(anhyclrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Ore., U.S.A., 1977).

Synthetic schemes using coupling reactions to identify active regulators of genes or gene expression The subject compounds, and derivatives thereof, can be prepared readily by employing synthetic methodology well-known in the art. Additional compounds may be synthesized and tested in a combinatorial fashion, to facilitate the identification of additional compounds which may be employed in the subject method.

A. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential hedgehog regulator lead compounds, as well as to refine the specificity, toxicity, and/or cytotoxic-kinetic profile of a lead compound. For instance, ptc, hedgehog, or smoothened bioactivity assays, such as may be developed using cells with either a ptc loss-of-function, hedgehog gain-of-function, or smoothened gain-of-function, can be used to screen a library of the subject compounds for those having agonist activity toward ptc or antagonist activity towards hedgehog or smoothened. Alternatively, bioactivity assays using cells with either a ptc gain-of-function, hedgehog loss-of-function, or smoothened loss-of-function, can be used to screen a library of the subject compounds for those having antagonist activity toward ptc or agonist activity towards hedgehog or smoothened.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject compounds. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 100 to 1,000 or more diversomers of the subject compounds can be synthesized and screened for particular activity or property.

Combinatorial library development and screening can be conducted, for example in analogy to the methods and procedures set forth in Beachy et al U.S. Pat. No. 7,291,626, incorporated herein by reference in its entirety. In an exemplary embodiment, a library of candidate compound diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate regulators or a substituent of a synthetic intermediate. According to the Still et al. technique, the library is synthesized on a set of beads, each bead including a set of tags identifying the particular diversomer on that bead. The bead library can then be "plated" with, for example, ptc loss-of-function, hedgehog gain-of-function, or smoothened gain-of-function cells for which a hedgehog antagonist is sought. The diversomers can be released from the bead, e.g. by hydrolysis.

Many variations on the above and related pathways permit the synthesis of widely diverse libraries of compounds which may be tested as regulators of hedgehog function.

B. Screening Assays

There are a variety of assays available for determining the ability of a compound such as a hedgehog regulator to regulate ptc, smoothened, or hedgehog function, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are hedgehog regulators. Such assays can be conducted by analogy described below by Beachy et al U.S. Pat. No. 7,291,626, (2007).

In addition to cell-free assays, test compounds can also be tested in cell-based assays. In one embodiment, cells which have a ptc loss-of-function, hedgehog gain-of-function, loss of kinase activity, smoothened gain-of-function phenotype can be contacted with a test agent of interest, with the assay scoring for, e.g., inhibition of proliferation of the cell in the presence of the test agent.

A number of gene products have been implicated in receptor-mediated signal transductions, including patched, GL1, GL2, GL3 family of transcription the serine/threonine kinase fused (fu) and smoothened, and patched and the induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling are described.

Reporter gene based assays described in the invention by Beachy et al, 2007 can be utilized by analogy for the subject compositions in the same way. These gene based assays appear to measure the end stage of the above described cascade of events, e.g., transcriptional modulation.

Accordingly, in practicing one embodiment of the assay, a reporter gene construct is inserted into the reagent cell in order to generate a detection signal dependent on ptc loss-of-function, hedgehog gain-of-function, smoothened gain-of-function, or stimulation by Shh itself or inhibitions of protein kinases. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant decrease in the amount of transcription indicates that the test compound has in some manner agonized the normal ptc signal (or modulated, antagonized the gain-of-function hedgehog or smoothened signal), e.g., the test compound is a potential hedgehog antagonist.

C. Exemplification

The invention now being generally described, it will be more readily understood by reference to the following examples which are included merely for purposes of illustration of certain aspects and embodiments of the present invention, and are not intended to limit the invention.

EXAMPLES

The following non-limiting examples are presented only to exemplify various embodiments of the invention and do not limit it in any fashion.

Example 1

In Jenkins, D. et al Anat 2007 Sep. 11, it states that studies of mouse mutants have demonstrated that Sonic hedgehog (SHH) signaling has a functional role in morphogenesis and differentiation at multiple sites within the forming urinary tract, and urinary tract malformations have been reported in humans with mutations that disrupt SHH signaling. However, there is only strikingly sparse and fragmentary information about the expression of SHH and associated signaling genes in normal human urinary tract development. (Jenkins, 2007) used immunohistochemistry to demonstrate that SHH protein was localized in distinct urinary tract epithelia in developing normal humans, in the urothelium of the nascent bladder and in kidney medullary collecting ducts. The expression patterns of the SHH-transducing proteins Patched (PTCH) and Smoothened (SMO) were consistent with long-range paracrine signaling associated with detrusor smooth muscle differentiation in the urogenital sinus. In the developing kidney, SHH and PTCH were expressed in epithelia of the collecting system between 16-26 weeks—surprisingly, SMO was not detected. Analysis of cell proliferation and Cyclin B1 immunohistochemistry at 26 weeks, as compared with a 28 week sample in which SHH expression was down-regulated, was consistent with the idea that SHH and PTCH might influence medullary collecting duct growth by regulating the subcellular localization of Cyclin B1 independently of SMO.

Collectively, this descriptive experimental result is similar to that of Beachy et al, 2007. These results, along with the inventors own literature research, certainly generates new hypotheses and evidence regarding SHH signal transduction in human urinary tract development as well as other anomalies described in the patent that help to explain the varied urinary tract malformations associated with anorectal malformation phenotypes noted in individuals with mutations in the SHH pathway Example 2

Females determined to be at risk of fetal malformations and who are seeking a further pregnancy are split into no treatment, folate treatment, D-chiroinositol treatment, and Folate+D-chiroinositol treatment arms. The respective regimens are administered once daily from before conception through the end of the first trimester. Relative to the untreated controls, the frequency of fetal malformations is reduced in each of the non-control arms. However, the reduction in frequency of fetal malformations in the co-therapy of the present invention is significantly better than in either of the other treatment arms.

Example 3

Females beginning birth control medication are assigned to similar treatment and control groups as in Example 1. Treatment is begun at the time of initiation of birth control medication, and continued until after a pregnancy occurs and for the following first trimester of pregnancy. Similar reductions as reported in Example 2 are seen. In addition, follow up of these females shows a lower level of breast cancer development than expected.

Example 4

Men preparing to initiate androgen ablative therapy are initiated on a course of D-chiroinositol prior to and throughout the treatment with the androgen ablative therapeutic. The frequency of male breast cancer found in these patients is substantially reduced as compared to controls not receiving the D-chiroinositol therapy.

Example 5

In order to demonstrate an effect of D-chiroinositol plus folate on Shh signaling during embryogenesis, curly tail mice (38) are chosen because of the genetic propensity for spinal defects mid associated genitourinary (GU) defects. These embryos are exposed to the present invention compound D-chiroinositol vs. myoinositol and internal examination is conducted. The severity of these defects among treated embryos treated with myoinositol are severe compared to those embryos treated with D-chiroinositol.

Example 6

To determine whether the downstream targets of the phosphatidyl inositol (PI3K) signaling pathway could be effected by an inhibitor, we can use a vehicle to inhibit the effect of inositol on neural tube closure. The curly tail mice embryos are cultured from E9.5 to E10.5, and the length of unclosed neural folds at the pnp are measured to indicate predisposition to spina bifida.

Embryos which are exposed to the kinase inhibitor alone have enlarged PNP's, reflecting the in vivo development of spinal NTD's by 50%-60% of curly tail embryos. Hence, inhibition of the down stream targets of the phostidylinositol signaling pathway blocks the protective effect of the inositol. Therefore, D-chiroinositol normalizes PNP closure in vitro.

D-chiroinositol, a phosphate derivative, plus folic acid could represent a possible novel adjunct therapy to prevent NTD's because the activation of certain isoforms by the phostidylinositol pathway is essential for prevention of these defects.

It is well-known that cancer remains a major health problem in the United States and in other developed countries. It is our effort here to reduce the burden of cancer on a physical, social, and psychological level. There is a constant search for more effective cancer treatments. While, it is well-known that many cancer specialists have won the battle for detecting and treating many cancers, however, there is still one problem that remains; the concept of prevention. This is a promising approach to control cancer. Also, the discovery of convergent signaling pathways in these contexts are something that cannot be overlooked as well because these signaling pathways control many cellular processes including cellular proliferation, survival, growth, and motility, all of which are critical processes for tumorigenesis. Without being bound to theory, it is the inventor's belief that the alteration of these converged pathways occurs in many cancerous states, many embryonic dysmorphic states, as well as many conditions that are the result of aberrant signaling, but otherwise unrelated to each other.

Based on the foregoing and the results described below by Beachy et al, 2007, the inventor suggests that the inclusion of the inositol compound, alone or in combination with other compounds as set forth more fully herein, is warranted as a treatment or prevention for a wide range of conditions related to aberrant growth (such as for cancers) birth defects due to pattern formation dysregulation during gestation, as well as other chronic diseases.

The goal is to identify combinations of the invention that target the tumor at vulnerable sites and interrupt specific pathways suspected in carcinogenesis. From the behavior and characteristics of malignant cells, several principal pathways of malignancy have been established. They include: Cell proliferation, cell cycle progression, metastases and invasion, angiogenesis, and apopotosis. Interestingly, we believe that at least one of the D-chiroinositol phosphates targets and acts on all of them. MDA-MB 231 human breast cancer cells are highly invasive tumor cells. These, and most other, tumors cells emit substances known as matrix metalloproteinases that allow metastastic cells to pass into blood vessels, myoinositol hexaphosphate significantly inhibits secretion of MMP-9 from MDA-MB 231 cells.

Introduction

Beachy, (2007) goes on to describe an essential role for Shh during Hair Follicle Morphogenesis. The hair follicle is a source of epithelial stem cells and site of origin for several types of skin tumors. While it is clear that follicles arise by way of a series of inductive tissue interactions, identification of the signaling molecules driving this process remains a major challenge in skin biology. Hair germs comprising epidermal placodes and associated dermal condensates were detected in both control and Shh−/− embryos, but progression through subsequent stages of follicle development was blocked in mutant skin. The expression of GUI and Ptc1 was reduced in Shh−/− dermal condensates and they failed to evolve into hair follicle papillae, suggesting that the adjacent mesenchyme is a critical target for placode-derived Shh. Despite the profound inhibition of hair follicle morphogenesis, late-stage follicle differentiation markers were detected in Shh−/− skin grafts, as well as cultured vibrissa explants treated with cyclopamine to block Shh signaling. These findings are stated as revealing an essential role for Shh during hair follicle morphogenesis, where it is required for normal advancement beyond the hair germ stage of development.

Early stages of organogenesis are marked by the appearance of mesenchymal condensates and focal cellular aggregates, or placodes, in adjacent epithelia. This process is driven to completion by a series of inductive signals traveling between epithelial and mesenchymal cell populations which ultimately give rise to the adult structure (reviewed in Gurdon, 1992; Thesleff et al., 1995). In skin appendages such as vibrissae and hair follicles, detailed analysis of tissue recombinants has revealed the existence of at least three morphogenetic signals: the embryonic dermis instructs overlying ectoderm to initiate placode formation; the placode transmits a signal generating a dermal condensate with hair follicle-inductive properties; and the condensate in turn sends a signal to nascent follicle keratinocytes stimulating their proliferation, downgrowth into the developing dermis, and reorganization to form the mature follicle (reviewed in Sengel, 1976; Hardy, 1992). The epithelial and mesenchymal components of the follicle remain in close proximity in mature hair bulbs, where the dermal papilla is surrounded by matrix cells giving rise to at least six phenotypically distinct epithelial cell types in the hair shaft and inner root sheath of the hair follicle. After birth the follicle epithelium cycles through periods of active growth (anagen), followed by regression (catagen) and inactivity (telogen) (reviewed in Cotsarelis, 1997). The morphogenetic program that accompanies the transition from telogen to anagen bears similarities to follicle development during embryogenesis, making this structure a unique model for studying certain aspects of organogenesis in the adult animal. Although a, large number of genes have been implicated at various stages of hair follicle development and cycling (reviewed in Rosenquist and Martin, 1996; Sterm et al, 1996; Widelitz et al, 1997; Millar, 1997), the molecular nature of the inductive signals that underlie the formation of the follicle is largely unknown.

In situ localization of transcripts encoding potential morphogens has revealed focal expression of Sunic hedgehog (Shh) in placodes of the epidermis and several other epithelia at early stages of development, with Ptc1 transcripts encoding a putative Shh receptor also present in adjacent mesenchymal cells (Bitgood and McMahon, 1995; Iseki et al., 1996; Oro et al., 1997; Motoyama et al., 1998). These findings, coupled with the accumulating evidence demonstrating a pivotal role for secreted Hedgehog proteins in a variety of developmental processes (reviewed in Hammerschmidt et al., 1997). Since the follicle is a source of cutaneous stem cells and a likely, site of origin for certain epithelial skin cancers (Cotsarelis et al., 1990; Lavker et al., 1993; Rochat et al., 1994; Hansen and Tennant, 1994), understanding the developmental biology of this organ is likely to provide insights relevant to normal skin function as well as wound-healing and neoplasia, and may shed light on fundamental aspects of organogenesis involving other structures as well.

To summarize, they concluded an obligatory role for Shh in the progression of hair follicle morphogenesis past the hair germ stage of development. The reduced expression of Ptc1 and Gli1 in Shh−/− dermal condensates, coupled with their failure to evolve into recognizable dermal papillae, argue that Shh is involved in regulating development of the mesenchymal component of the hair follicle, although a requirement for Shh signaling in the epithelial component of the follicle cannot be excluded. In the absence of dermal papillae normal hair follicle morphogenesis does not proceed, underscoring the critical influence these cells have on growth and remodeling of developing follicle epithelium (Jahoda et al., 1984; Weinberg et al., 1993). Interestingly, biochemical differentiation of the follicle can take place in the absence of normal morphogenesis, implying that these two processes are regulated independently in this organ. According to Beachy et al. (2007), additional experiments will be required to formally define which component of the developing follicle is functionally impaired in Shh−/− embryos, and to determine whether Shh has additional roles at later stages of follicle development or during hair cycling. (Johnson et al., 1996; Hahn et al., 1996; Oro et al., 1997; Fan et al., 1997; Xie et al., 1998).

The experiments detailed below by Beachy et al (2007) are believed to be equally applicable to the D-chiroinositol compounds (phosphates thereof and other derivatives thereof) used in the present invention.

Methods

Animals and Skin Transplantation

The generation and identification of Shh mutant mice was performed as described (Chiang et al., 1996). Embryonic skin was grafted onto the dorsal fascia of nude mice beneath a protective silicone chamber using a modification of a previously-described technique (Dlugosz et al., 1995). The chamber was removed 11-12 days after grafting and tissue harvested for analysis after an additional one to four weeks. Animals were handled in accordance with NIH guidelines.

Immunohistochemistry

Tissue is fixed overnight in Carnoy's or Bouin's solution for detecting keratins (K1, K10, K5, K14, and K17), loricrin, and filaggrin; fixation with neutral-buffered formalin is used for tissues immunostained with Lef-1, Ki67, and hair keratin (AE13) antibodies. Samples are embedded in paraffin and 8 m sections cut for immunostaining. Immunoreactivity of antigens in formalin-fixed sections is restored by immersing slides in a boiling 0.01M citrate buffer, pH 6, for 10 minutes. The following primary antibodies are used at the indicated dilutions for immunostaining: rabbit anti keratins K1, K10, K5 and K14 (1:500) (Roop et al., 1984), loricrin and filaggrin (1:500) (Roop et al., 1987); rabbit anti-K17 (1:1000) (McGowan and Coulombe, 1998), rabbit anti-Lef-1 (1:200) (Travis et al., 1991), rabbit anti-Ki67, NCL-Ki67p (Novocastra Laboratories, Ltd., Newcastle upon Tyne, UK) (1:200); and mouse monoclonal AE13 hybridoma supernatant, which recognize type I hair keratins (1:5) (Lynch et al., 1986), as described in Beachy et al (2007). Tissue sections are incubated with primary antibodies diluted in tris-buffered saline containing 1% bovine serum albumin, typically for 1-2 hours at room temperature. Subsequent immunostaining procedures are performed using peroxidase Vectastain ABC kits (Vector Laboratories, Inc., Burlingame, Calif.) and 3,3'diaminobenzidine (Sigma, St. Louis, Mo.) as a substrate, according to the manufacturers' recommendations. Sections are counterstained with hematoxylin and mounted using Permount (Fisher Scientific, Pittsburgh, Pa.).

In Situ Hybridization

Non-radioactive RNA in situ hybridization is performed on 5 m sections essentially as described (Groves et al., 1995), using previously described sequences for Gli1 (Walterhouse et al., 1993), Ptc1 (Goodrich et al., 1996), and BMP-4 (Jones et al., 1991).

Vibrissa Follicle Explants

Vibrissa follicle explants are established using CD-I mouse embryos at 13.5 days of gestation according to a previously described protocol (Hirai et al., 1989), with minor modifications. Vibrissa pads are transferred onto Nuclepore filters (13 mm, 8 m pores), and floated on, 2 ml of medium [DMEM (Life Technologies, Gaithersburg, Md.)+Ham's F12 medium (Life Technologies) (1:1), with 1% ECS (Intergen, Purchase, N.Y.), penicillin (50 units/ml) and streptomycin (50 gg/ml) (Life Technologies)] in 6-well plates. Similar results are obtained using a DMEM-based medium, without the addition of Ham's F12. Explants are fed fresh medium every two days. Microdissection is performed with the aid of a Nikon SMZ-2T stereomicroscope and photomicrographs were taken using an Olympus OM-4 camera. Cyclopamine is stored at −20 as a 10 mM stock in 95% EtOH.

RNA Isolation and RT-PCR

RNA is obtained by solubilizing individual explants in TriZol (Life Sciences) and isolating as recommended by the manufacturer. cDNA is synthesized using Superscript II Rnase H reverse transcriptase with random primers (Life Technologies), and RT-PCR performed using the primers set forth in Beachy et al's, (2007) (Walterhouse et al., 1993). The following PCR conditions are used for MHKA1, Hacl-1, and actin: 95.times.3 min "hot start", 95.times.50 sec, 58.times.30 sec, and 72.times.60 sec for 25 (actin) or 35 cycles(MHKA1 and Hacl-1); 72.times.7 min. PCR conditions for profilaggrin primers were as previously described (Bickenbach et al., 1995). Reaction products are run through 1.5% agarose gels and visualized with ethidiurn bromide.

Early stages of hair follicle development appear similar in control and Shh−/− embryos. Hair germs, consisting of clusters of columnar basal keratinocytes protruding into the developing dermis with associated dermal condensates, are detected in the skin of both mutant and control embryos at 15.5 days of gestation. Despite the similar morphology of control and Shh-deficient hair germs, a dramatic difference in gene expression patterns is revealed by in situ hybridization. The level of Gli1 mRNA is markedly reduced in both the epithelial and mesenchymal components of Shh−/− primary hair germs. In addition, expression of Ptc1 is reduced in Shh mutant hair germs, although some placodes contain levels slightly above background. These findings are consistent with previous reports identifying Shh as a positive regulator of both Gli1 and Ptc1 (Mango and Tabin, 1996; Mango et al., 1996; Lee et al., 1997; Sasaki et al., 1997), and suggest that Shh is signaling in both the epithelial and mesenchymal cells of the developing follicle. In contrast to Gli1 and Ptc1, BMP-4 mRNA is clearly detectable in condensates of mutant and control embryos, arguing against a requirement for Shh in the induction of BMP-4 expression. Thus, although Shh is not required for the initiation of hair follicle development, primary hair germs that arise in Shh mutant skin are deficient in the expression of at least some Shh target genes.

In control embryos, the interval between E15.5 and E17.5 is marked by rapid proliferation and downgrowth of the follicle into the developing dermis, accompanied by a several-fold increase in the mass of the follicle epithelium and reorganization into distinct cellular compartments. In the most mature follicles, keratinocytes in the most peripheral cell layer, which give rise to the outer root sheath in the mature follicle, assum a columnar arrangement perpendicular to the long axis of the developing follicle; cells located centrally are without a definite orientation at this stage but will eventually be replaced by the three concentric layers of inner root sheath cells and the three cell types comprising the hair shaft; and the epithelial cells of the deepest portion of the follicle, the future hair bulb, have surrounded what is at this stage a well-defined cluster of mesenchymal cells, the dermal papilla. Even the less mature follicles exhibit an organized "cap" of mesenchymal cells at their invaginating tips. In striking contrast, hair follicles in skin from mutant embryos at E17.5 fail to develop past the hair germ stage seen at E15.5. Although the follicle epithelium is most obviously affected due to its lack of growth, organizing dermal condensates and dermal papillae am conspicuously absent in mutant skin. These results are consistent with the idea that epidermis-derived Shh (Bitgood and McMahon, 1995; Iseki et a)., 1996; Oro et al., 1997; Motoyama et al., 1998) functions as a paracrine signal regulating development of the mesenchymal component of the hair follicle. Inhibition of follicle formation is not likely to be due to a general disruption of skin development since epidermal morphogenesis, marked by the appearance of granular and cornified cell layers, took place by E17.5 in both control and mutant embryos.

Additional studies are performed to determine whether Shh influenced the expression of epithelial differentiation markers in embryonic skin. Keratinocytes in developing hair follicles can be distinguished by a relative deficiency of K5 and K14, keratins that are abundant in surrounding epidermal basal cells (Kopan and Fuchs, 1989; Byrne et al., 1994). Immunohistochemical staining of E17.5 embryos reveals greatly reduced or undetectable levels of K14 in a subpopulation of cells comprising the normal follicles in control embryos as well as the primordial follicles seen in Shh−/− embryos. Moreover, K17, which is normally not detected in interfollicular epidermis but is expressed in developing and mature hair follicles (Panteleyev et al., 1997; McGowan and Coulombe, 1998), is localized to the follicular epithelium in both control and mutant skin. Thus, although morphogenesis of hair follicles in Shh−/− skin fails to progress past the hair germ stage, these structures contain epithelial cells that have initiated a terminal differentiation program characteristic of developing follicle keratinocytes. Consistent with these morphological findings, the expression level of epidermal-specific differentiation markers (keratins 1 and 10, loricrin, and filaggrin) in Shh−/− skin is similar to or greater than in control epidermis, based on immunchistochemical staining.

Since Shh−/− mice are not viable, post-natal analysis of mutant skin is performed following grafting onto nude mice. Whereas skin from control mice produced abundant pigmented hairs, transplanted Shh−/skin foiled to generate detectable hairs but exhibited a pigmented graft site, consistent with the strain of donor skin. The histology of control skin grafts reveals the typical structures seen in normal mouse skin, including numerous hair follicles and sebaceous glands. In striking contrast, mutant skin failed to produce normal-appearing follicles, hair shafts, or sebaceous glands, but in some cases exhibit a thickened epidermis with focal areas of hyperkeratosis. Conspicuous aggregates of basophilic cells with scant cytoplasm are detected at the dermal-epidermal junction in these mutant grafts. Interestingly, the morphology of cells in the Shh-deficient keratinocyte aggregates is reminiscent of cells in control hair bulbs, and additional analyses revealed biochemical similarities. Cells in these aggregates are unreactive with K5 antibodies, exhibit abundant nuclear Lef-1 expression (Zhou et al., 1995), and contain a high proportion of proliferating cells detected by Ki67 immunostaining. Interestingly, short columnar structures resembling abortive hair shafts are associated with some of the Shh mutant keratinocyte aggregates. Moreover, these structures express hair-specific keratin , indicating that an advanced stage in the follicle differentiation program is achieved despite a dramatic disruption of normal morphogenesis. Rarely, a small cluster of mesenchymal cells is seen associated with the base of a keratinocyte aggregate, where these cells immunostain with Lef-1 antibody. These findings suggest that a rudimentary dermal papilla is present in at least some of the hair germs seen in Shh mutant grafts.

To better define the temporal requirement for Shh during follicle development, tissue culture studies are performed using cyclopamine (GaTield and Keeler, 1996), which has recently been shown to block Shh signaling in neural plate explants (Cooper et al., 1998; Incardona et al., 1998). Explants are established using vibrissa pads from mice at 13.5 days of gestation (Hirai et al., 1989). When grown for six to eight days in culture, explants undergo robust morphogenesis resulting in the formation of elongated, grossly normal-appearing vibrissa follicles. These follicles contain hair shafts and express genes encoding mouse hair keratin A 1 (MHKA 1) (Kaytes et al., 1991) and a hair cortex-specific marker Hacl-1 (Huh et al., 1994), detected by RT-PCR (FIG. 11B). Treatment of explants with cyclopamine results in striking inhibition of morphogenesis, indicating that Shh signaling is required during or shortly after the hair germ stage of vibrissa, follicle development. In keeping with results using Shh mutant skin, hair-specific transcripts are detected in cyclopamine-treated grafts despite their altered development, providing further support for the notion that biochemical differentiation of the follicle is not necessarily coupled to its morphogenesis. Both control and cyclopamine-treated explants accumulate profilaggrin mRNA, indicating that disruption of Shh signaling does not inhibit epidermal differentiation.

Fetal Alcohol Syndrome Examples

Example 7

Female rats are administered alcohol for 2 weeks and then mated. The alcohol administration continues through out pregnancy and the rate of fetal alcohol syndrome related defects in the offspring are noted. A second set of rats from the same strain are mated without having the alcohol treatment as a control and the rate of defects of the same type as noted in the first arm are noted. The control arm does not display any significant number of the defects that are noticed in the alcohol treatment arm. A third arm of the study includes rats that are administered D-chiroinositol or a phosphorylate thereof before and during the alcohol treatment and are otherwise treated in the same manner as in the alcohol treatment above. The rate of fetal alcohol syndrome defects noted in the inositol treatment group is substantially less than the rate of detects seen in the inositol free alcohol treated group.

Example 8

Example 7 is repeated except that a cholesterol reducing medication is used instead of the alcohol treatment. Similar results to that in Example 1 are obtained.

REFERENCES FOR EXAMPLES

Bickenbach, J. R. Greer, J. M., Bondman, D. S., Rothnagel, J. A., and Roop, D. R. (1995). Loricrin expression is coordinated with other epidermal proteins and the appearance of lipid lamellar granules in development. J. Invest. Dermatol. 104, 405-410.

Bitgood, M. J. and McMahon, A. P. (1995). Hedgehog and Bmp genes are coexpressed at many diverse sites of cell-cell interaction in the mouse embryo. Dev Biol. 172, 126-138.

Byrne, C., Tainsky, M., and Fuchs, E. (1994). Programming gene expression in developing epidermis. Development 120, 2369-2383.

Chiang, C., Litingtung, Y., Lee, E., Young, K. E., Corden, J. L., Westphal, H, and Beachy, P. A. (1996). Cyclopia and defective axial patterning in mice lacking Sonic hedgehog gene function. Nature 383, 407-413.

Cooper, M. K., Porter, J. A., Young, K. E., and Beachy, P. A. (1998). Teratogen-mediated inhibition of target tissue response to Shh signaling. Science 280, 1603-1607.

Cotsarelis, G. (1997). The hair follicle: dying for attention. Am. J. Pathol. 151, 1505-1509.

Cotsarelis, G., Sun, T. T., and Lavker, R. M. (1990). Label-retaining cells reside in the bulge area of pilosebaceous unit: implications for follicular stem cells, hair cycle, and skin carcinogenesis. Cell 61, 1329-1337.

Dlugosz, A. A., Glick, A. B., Tennenbaum, T., Weinberg, W. C., and Yuspa, S. H. (1995). Isolation and utilization of epidermal keratinocytes for oncogene research. Methods Enzymol. 254, 3-20.

Fan, H., Oro, A. E., Scott, M. P., and Khavari, P. A. (1997). Induction of basal cell carcinoma features in transgenic human skin expressing Sonic Hedgehog. Nat. Med. 3, 788-792.

Gaffield, W. and Keeler, R. F. (1996). Steroidal alkaloid teratogens: Molecular probes for investigation of craniofacial malformations. Journal Of Toxicology-Toxin Reviews 15, 303-326.

Goodrich, L. X, Johnson, R. L., Milenkovic, L., McMahon, J. A., and Scott, M. P. (1996). Conservation of the hedgehoglpatched signaling pathway from flies to mice: Induction of a mouse patched gene by Hedgehog. Genes Dev 10, 301-312.

Groves, A. K., George, K. M., Tissier-Seta, J. P., Engel, J. D., Brunet, J. F., and Anderson, D. J. (1995). Differential regulation of transcription factor gene expression and phenotypic markers in developing sympathetic neurons. Development 121, 887-901.

Gurdon, J. B. (1992). The generation of diversity and pattern in animal development. Cell 68, 185-199.

Hahn, H., Wicking, C., Zaphiropoulous, P. G., Gailani, M. R., Shanley, S., Chidambaram, A., Vorechovsky, I., Holmberg, E., Unden, A. B., Gillies, S., Negus, K., Smyth, I., Pressman, C., Leffell, D. J., Gerrard, B., Goldstein, A. M., Dean, M., Toftgard, R., Chenevix-Trench, G., Wainwright, B., and Bale, A. E. (1996). Mutations of the human homolog of Drosophila patched in the nevoid basal cell carcinoma syndrome. Cell 85, 841-851.

Hammerschmidt, M., Brook, A., and McMahon, A. R (1997). The world according to hedgehog, Trends. Genet. 13, 14-21.

Hansen, L. A. and Tennant, R. W. (1994). Follicular origin of epidermal papillomas in v-Ha-ras transgenid TGAC mouse skin. Proc. Natl. Acad. Sci USA 91, 7822-7826.

Hardy, M. H. (1992). The secret life of the hair follicle. Trends. Genet. 8, 55-61.

Hirai, Y., Nose, A., Kobayashi, S., and Takeichi, M. (1989). Expression and role of E- and P-cadherin adhesion molecules in embryonic histogenesis. 11. Skin morphogenesis. Development 105, 271-277.

Huh, N., Kashiwagi, M., Konishi, C., Hashimoto, Y., Kohno, Y., Nomura, S., and Kuroki, T. (1994). Isolation and characterization of a novel hair follicle-specific gene, Hacl-1. J Invest. Dermatol. 102, 716-720.

Incardona, J. P., Gaffield, W., Kapur, R. P., and Roelink, H. (1998). The teratogenic Veratrum alkaloid cyclopamine inhibits Sonic hedgehog signal transduction. Development 128, 3553-3562.

Iseki, S., Araga, A., Ohuchi, H., Nohno, T., Yoshioka, R. Hayashi, F., and Noji, S. (1996). Sonic hedgehog is expressed in epithelial cells during development of whisker, hair, and tooth. Biochem. Biophys. Res. Commun. 218, 688-693.

Jahoda, C. A., Home, K. A., and Oliver, R. F. (1984). Induction of hair growth by implantation of cultured dermal papilla cells. Nature 311, 560-562.

Johnson, R. L., Rothman, A. L., Xie, J., Goodrich, L. V., Bare, J. W., Bonifas, J. M., Quinn, A. G., Myers, R. M., Cox, D. R., Epstein, E. H., Jr., and Scott, M. P. (1996). Human homolog of patched, a candidate gene for the basal cell nevus syndrome. Science 272, 1668-1671.

Jones, C. M., Lyons, K. M., and Hogan, B. L. (1991). Involvement of Bone Morphogenetic Protein-4 (BMP4) and VgrI in morphogenesis and neurogenesis in the mouse. Development UI, 531-542.

Kaytes, P. S., McNab, A. R., Rea, T. J., Groppi, V., Kawabe, T. T., Buhl, A. E., Bertolino, A. P., Hatzenbuhler, N. T., and Vogeli, G. (1991). Hairspecific, keratins: characterization and expression of a mouse type I keratin gene. J Invest. Dermatol. 97, 835-842.

Kopan, R. and Fuchs, E. (1989). A new took into an old problem: keratins as tools to investigate determination, morphogenesis, and differentiation in skin. Genes. Dev. 3, 1-15.

Lavker, R. M., Miller, S., Wilson, C., Cotsarelis, G., Wei, Z. G., Yang, J. S., and Sun, T. T. (1993). Hair follicle stem cells: their location, role in hair cycle, and involvement in skin tumor formation. J. Invest. Dermatol. 101, 168-26S.

Lee, J., Platt, K. A., Censullo, P., and Ruiz i Altaba, A. (1997). Gli1 is a target of Sonic hedgehog that induces ventral neural lube development. Development 124, 2537-2552.

Lynch, M. H. O'Guin, W. M., Hardy, C., Mak, L., and Sun, T. T, (1986). Acidic and basic hair/nail ("hard") keratins: their colocalization in upper cortical and cuticle cells of the human hair follicle and their relationship to "soft" keratins. J. Cell Biol. 103, 2593-2606.

Marigo, V., Johnson, R. L., Vortkamp, A., and Tabin, C. J. (1996). Sonic hedgehog differentially regulates expression of GL1 and GL13 during limb development. Dev Biol. 180, 273-283.

Marigo, V. and Tabin, C. J. (1996). Regulation of Patched by Sonic hedgehog in the developing neural tube. Proc. Nad. Acad. ScL USA 93, 9346-9351.

McGowan. K. and Coulombe, P. A. (1998). Expression of keratin 17 coincides with the determination of major epithelial lineages during mouse skin development. J. Cell. Biol. (in press)

Millar, S. (1997). The Role of Patterning Genes in Epidermal Differentiation. In "Cytoskeletal-Membrane Interactions and Signal Transduction" (P. Cowin and M. W. Klymkowsky, Eds.), pp. 87-102. Landes Bioscience, Austin, Tex.

Motoyama, J. Takabatake, T., Takeshima, K., and Hui, C. (1998). Ptch2, a second mouse Patched gene is coexpressed with Sonic hedgehog. Nat. Genet. 18, 104-106.

Oro, A. E., Higgins. K. M., Hu, Z. L., Bonifas, J. M., Epstein, E. H., Jr., and Scott, M. P. (1997). Basal cell carcinomas in mice overexpressing sonic hedgehog. Science 276, 817-821.

Panteleyev, A. A., Paus, R., Wanner, R., Numberg, W., Eichmuller, S., Tliiel, R., Zhang, J., Henz, B. M., and Rosenbach, T. (1997). Keratin 17 gene expression during the murine hair cycle. J. Invest. Dermatol 108, 324-329.

Rochat, A., Kobayashi, K., and Barrandon, Y. (1994). Location of stem cells of human hair follicles by clonal analysis. Cell 76, 1063-1073.

Roop, D. R., Cheng, C. K., Titterington, L., Meyers, C. A., Stanley, J. R., Steinert, P. M., and Yuspa, S. H. (1984). Synthetic peptides corresponding to keratin subunits elicit highly specific antibodies. J. Biol. Chem. 259, 8037-8040.

Roop, D. R., Huitfeldt, H., Kilkenny, A., and Yuspa, S. H. (1987). Regulated expression of differentiation-associated keratins in cultured epidermal cells detected by monospecific antibodies to unique peptides of mouse epidermal keratins. Differentiation 35, 143-150.

Rosenquist, T. A. and Martin, G. R. (1996). Fibroblast growth factor signaling in the hair growth cycle: expression of the fibroblast growth factor receptor and ligand, genes in the murine hair follicle. Dev. Dyn. 205, 379-386.

Sasaki, H., Hui, C., Nakaftiku, M., and Kondoh, H. (1997). A binding site for Gli proteins is essential for HNF-3beta floor plate enhancer activity in transgenics and can respond to Shh in vitro. Development 124, 1313-1322.

Sengel, P. (1976). "Morphogenesis of Skin." Cambridge University Press, Cambridge. Sterm, K. S., Combates, N. J., Eilertsen, K-J., Gordon, J. S., Pardinas, J. R., Parimoo. S., and Prouty, S. M. (1996). Hair follicle growth controls. Dermatol Clin. 14, 543-558.

Thesleff, I., Vaahtokari, A., and Partanen, A. M. (1995). Regulation of organogenesis. Common molecular mechanisms regulating the development of teeth and other organs. Int. J. Dev. Biol. 39, 35-50.

Travis, A., Amsterdam, A., Belanger, C., and Grosschedl, R. (1991). LEF-1, a gene encoding a lymphoid-specific protein with an HMG domain, regulates T-cell receptor alpha enhancer function. Genes Dev. 5, 880-894.

Walterhouse, D., Ahmed, M., Slusarski, D., Kalamaras, J., Boucher, D., Holmgren, R., and Iannaccone, P. (1993). gli, a zinc finger transcription factor and oncogene, is expressed during normal mouse development. Dev. Dyn. 199, 91-102.

Weinberg, W. C, Goodman, L. V., George, C., Morgan, D. L., Ledbetter, S., Yuspa, S. H., and Lichti, U. (1993). Reconstitution of hair follicle development in vivo: determination of follicle formation, hair growth, and hair quality by dermal cells. J. Invest. Dermatol. 100, 229-236.

Widelitz, R. B., Jiang, T X, Noveen, A., Ting-Berreth, S. A., Yin, E., Jung, H. S., and Chuong, C. M. (1997). Molecular histology in skin appendage morphogenesis. Mi.about-.rosc. Res. Tech. 38, 452-465.

Xie, J., Murone, M., Luoh, S. M., Ryan, A., Gu, Q., Zhang, C., Bonifas, J. M., Lam, C. W., Hynes, M., Goddard, A., Rosenthal. A., Epstein, E. H. J., and deSauvage, F. (1998). Activating Smoothened mutations in sporadic basal-cell carcinoma. Nature 391, 90-92.

Zhou. P., Byrne, C., Jacobs, J., and Fuchs, E. (1995). Lymphoid enhancer factor I directs hair follicle patterning and epithelial cell fate. Genes Dev. 700-713.

All of the references cited above and throughout the specification are hereby incorporated by reference herein.

Those skilled in the art will recognize, or be able to ascertain using no more than routine experimentation, many equivalents to the specific embodiments of the invention described herein. Such equivalents are intended to be encompassed by the following claims.

In general inositol (underivitzed) can be recovered in the myo form from plant sources. Chemical synthesis of the underivitized inositol enantiomers is known in the art and many are available, although many in small quantities not readily convenient for commercial batch production. Pinitol is another known compound which is a monomethyl ester of an inositol isomer. Conversion of these known compounds to the deoxo versions can generally be accomplished by virtue of the Barton Mccombie deoxygenation reaction, exemplified with respect to nucleosides in U.S. Pat. No. 6,822.089, incorporated herein by reference. Esterification of one or more of the hydroxy groups of the inositol structure with phosphoric acid, pyrophosphoric acid, carboxylic acids, carbonic acids, sulfonic acid, sulfouous acid and further esters of the other hdyroxy groups of these acidic compounds can be achieved by techniques available to the synthetic chemist. Techniques for the introduction of other substituents such as halogens, oxo groups, and substituents having a carbon atom bound to the inositol ring will also be known to those of ordinary skill in the synthetic chemistry art. Phosphorylation may also be obtained in a variety of substitution patterns by complete phosphorylation of the inositol and then exposure to specific enzymes or bacterial for specific dephosphorylation of particular positions, leaving different phsophorylation patterns. Once prepared, the various phosphorylates can be separated from each other by commonly known analytical and separation techniques such as HPLC etc.

Compositions of the invention include those of an inositol, an inositol derivative, an inositol metabolite, polysaccharides containing inositol, and inositol containing phospholipid and an additional active agent which is not an inositol. Where the additional active agent is a folate, it is administered in an amount equivalent to an amount of folic acid selected from about 200 μg, about 250 μg, about 300 μg, about 350 μg, about 400 μg, about 450 μg, about 500 μg, about 600 μg, about 650 μg, about 700 μg, about 750 μg, about 800 μg, about 850 μg, about 900 μg, about 950 μg, about 1 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, and about 1.6 mg per day. Birth defects within the invention uses include those where the defect is VATER/VACTERL association (vertebral [defects], [imperforate] anus, tracheoesophageal [fistula], radial and renal [dysplasia]), rachischisis, (aka spinal dysraphism) such as spina bifida (including, but not limited to spina bifida aperta (aka spinabifida cystica); spinabifida occulta; and occult spinal disorder, among others) and (b) craniorachischisis (aka cranial dysraphism) such as cranium bifida (aka encephalocele or eraniocele) each of spina bifida and cranium bifida being of any of the following types meningocele, myelomeningocele, lipomeningocele, and lipomyelomeningocele among others; (c) anencephaly; and (d) chiari malformation; (2) caudal regression syndrome, caudal dysplasia sequence, congenitalsacral agenesis; sironmelia(mermaid syndrome), sacral regression and the like; (3) cranio-facial defects such as, without limitation, facial cleft (aka prosopoanoschisis, including without limitation cleft palate, cleft lip, velopharyngeal malformation (including without limitation bifid uvula), etc.); (4) anorectal malformations including, but not limited to (a) impertorate anus, (b) rectoperineal fistula, (c) recto-bladder neck fistula; (d) persistent urogenital sinus, (e) persistent cloaca, etc.; (5) bucket-handle malformation;

among others, acrocallosal syndrome, Basal cell nevus syndrome, bardet-Biedl syndrome, Biemond syndrome, Ectrodactyly-ectoderma dysplasia, cleft lip/palate, Ellis Van Creveld syndrome, meckel Gruger syndrome McKusick-kaufman syndrome, Mirror hand deformity(ulnar dimelia) Mohr syndrome, oral-facial-digital syndrome, Pallister Hall syndrome, Greig cephalopolysyndactyly, Post axial polydactyly, GreigRubinstein-Taybi syndrome, Cardiofaciocutaneous syndrome, noonan syndrome, short rib polydactyly, extra deformed fingers and toes, Lowe syndrome including ocular and renal defects, mental retardation. This inositol type compound, whether inositol or an inositol derivative, metabolite, polysaccharides containing inositol, and inositol containing phospholipid is administered in an amount that is equivalent to an amount of D-chiroinositol selected from the group consisting of about 0.1 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 50 mg, about 75 mg, about 100 mg, about 125 mg, about 150 mg, about 200 mg, about 250 mg, about 300 mg, about 350 mg, about 400 mg, about 500 mg, about 600 mg, about 700 mg, about 750 mg, about 800 mg, about 900 mg, about 950 mg, about 1 g per day, about 1.2 g per day, about 1.8 g per day, about 2 g per day, about 2.5 g per day, about 3 g per day, about 5 g per day, about 10 g per day, about 12 g per day, about 18 g per day, about 24 g per day, about 30 g per day, about 45 g per day, and about 60 g per day. Certain methods include administration to patients where the patient is a female receiving at least one treatment selected from birth control, hormonal replacement therapy, or antiandrogenic therapy; or said patient is a male receiving at least one treatment selected from estrogenic treatment and hormonal ablative therapy; or said patient is a male to female trans sexual receiving at least one therapy selected from estrogenic treatment and antiandrogenic treatment, more specifically in some patients, the estrogenic insult is from a medicinal source and said medicinal source is selected from the group consisting of estrogenic, progestogenic, or antiandrogenic therapy . In some embodiments, the treatment is of a cancer selected from basal cell carcinoma (shh gain of function), Multiple basal cell nevi, squamous cell carcinoma (ptc activity) medulloblastoma, primitive neuroectodermal tumor(PNET), Gorlin syndrome, nevoid basal cell carcinoma syndrome, harmartomas, blue rubber-bleb nevus syndrome, Turcot syndrome, glioma polyposis syndrome, Rubinstein-Taybi syndrome, Cowden tumor syndrome, rabdomyosarcoma (RMS), alveolar rhabdomyosarcoma, botryoid rhabdomyosarcoma, embryonal rhabdomyosarcoma, spindle cell rhabdomyosarcoma, pleomorphic rhabdomyosarcoma, soft tissue sarcoma, rhabdomyoblasts, pediatric sarcoma, cell carcinoma, carcinosarcoma, adenocystic carcinoma, epidermoid carcinoma, nasopharyngeal carcinoma, bladder carcinoma, renal cell carcinoma, papilloma, or an epidermoidoma. In other embodiments, the birth defect is VATER/VACTERL association (vertebral [defects], [imperforate] anus, tracheoesophageal [fistula], radial and renal [dysplasia])rachischisis (aka spinal dysraphism) such as spina bifida (including, but not limited to spina bifida aperta (aka spinabifida cystica); spinabifida occulta; and occult spinal disorder, among others) and (b) craniorachischisis (aka cranial dysraphism) such as cranium bifida (aka encephalocele or craniocele) each of spina bifida and cranium bifida being of any of the following types meningocele, myelomeningocele, lipomeningocele, and lipomyelomeningocele among others; (c) anencephaly; and (d) chiari malformation; (2) caudal regression syndrome, caudal dysplasia sequence, congenitalsacral agenesis; sironmelia (mermaid syndrome), sacral regression and the like; (3) cranio-facial defects such as, without limitation, facial cleft (aka prosopoanoschisis, including without limitation cleft palate, cleft lip, velopharyngeal malformation (including without limitation bifid uvula), etc.); (4) anorectal malformations including, but not limited to (a) imperforate anus, (b) rectoperineal fistula, (c) recto-bladder neck fistula; (d) persistent urogenital sinus, (c) persistent cloaca, etc.; (5) bucket-handle malformation; among others. Biemond syndrome, Ectrodactyly-ectoderma dysplasia, cleft lip/palate, Ellis Van Creveld syndrome, Muir Torre syndrome, Cowden syndrome, Carney complex, Birt-Hogg-Dube syndrome, Gorlin syndrome (ptc loss-of-function), Gorlin-Goltz syndrome, basal cell nevus syndrome, bifid-rib basal-cell nevus syndrome, multiple basal cell nevi, Meckel Gruger syndrome, McKusick-Kaufman syndrome, Mirror hand deformity (ulnar dimelia) Mohr syndrome. Oral-facial-digital syndrome, Pallister Mall syndrome, cephalopolysyndactyly, Post axial polydactyly, GreigRubinstein-Taybi syndrome, retinoblastoma. Cardiofaciocutaneous syndrome, Noonan syndrome, short rib polydactyly, extra deformed fingers and toes, Lowe syndrome (including ocular and renal defects), Renal Colombo syndrome, Retinitis pigmentosa. In some embodiments cotherapy of an oinositol or derivative thereof or metabiolite thereof or of a polysacharride having inositol components or an inositol phospholipid is administered as a cotherwith other active agents to a patient selected from the group selected from (a) those in need of preventing of inhibiting of proliferation, growth, and/or metastases of tissues or conditions selected from the group consisting of breast tissue, prostate tissue, cervical cancer caused by human papiloma virus subtypes (HPV), Kaposis sarcoma, lung cancer, adenocarcinoma, gut derived tumors, colon cancers due to adenocarcinomas, and human erythroleukemia and (b) those in need of tissue regulation selected from the group consisting of regulation of neural tissues, regulation of bone and cartilage formation and repair, regulation of ovulation, regulation of spermatogenesis, regulation of smooth muscle, regulation of lung, liver, intestines, colon, rectum and other organs arising from the primitive gut as well as the distal hindgut, regulation of hematopoietic function, hemopoietic stem cells, and regulation of skin and hair growth, and modulation of cell proliferation which includes, without limitation, inhibition of angiogenesis. The modulation of cell proliferation also includes a basal cell carcinoma, medulloblastoma, primitive neuroectodermal tumor, PNET, Gorlin syndrome, nevoid basal cell carcinoma syndrome, harmartomas, blue rubber-bleb nevus syndrome, Turcot syndrome, glioma polyposis syndrome, Rubinstein-Taybi syndrome, Cowden tumor syndrome, rabdomyosarcoma, RMS, alveolar rhabdomyosarcoma, botryoid rhabdomyosarcoma, embryonal rhabdomyosarcoma, spindle cell rhabdomyosarcoma, pleomorphic rhabdomyosarcoma, soft tissue sarcoma, rhabdomyoblasts, pediatric sarcoma, sarcoma squamous cell carcinoma, carcinosarcoma, adenocystic carcinoma, epidermoid carcinoma, nasopharyngeal carcinoma, bladder carcinoma, renal cell carcinoma, papilloma, karposi's sarcoma, and an epidermoidoma. The inihibiton of cell proliferation also includes preventing or inhibiting the proliferation, growth, and/or metastases of one or more cancers selected from the group consisting of breast cancer, prostate cancer, especially prostatic androgen dependent PCA-LNA-p cells ,cervical cancer, caused by human papiloma virus subtypes (HPV), Kaposis sarcoma, lung cancer, (in particular, small cell lung cancer, adenocarcinoma; gut derived tumors (including but not limited to cancer of the esophagus, stomach, pancreas, biliary duct system, intestinal(gastric) system, colon cancers due to adenocarcinomas, and human erythroleukemia.

The instant compounds may also be co-administered with other well known therapeutic agents that are selected for their particular usefulness against the condition that is being treated.

For example, instant compounds are useful in combination with known anti-cancer agents. Combinations of the presently disclosed compounds with other anti-cancer or chemotherapeutic agents are within the scope of the invention. Examples of such agents can be found in Cancer Principles and Practice of Oncology by V. T. Devita and S. Heilman (editors), 8th edition (April, 2008), Lippincott Williams & Wilkins Publishers. A person of ordinary skill the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors and agents that interfere with cell cycle checkpoints. The instant compounds are particularly useful when co-administered if needed with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate,4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5.alpha.-reductase inhibitors, nilutamide, flutamide, bicalutamide, liarozole, and abiraoacetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, alpha-difluromethylomithine, ILX23-7553, trans-N-(4'-hydroxyphenyl)retinamide, N-4-carboxyphenyl, retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, anti-metabolites; biological response modifiers; hormonal/anti-hormonal therapeutic agents, haematopoietic growth factors, monoclonal antibody targeted therapeutic agents and topoisomerase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans,trans,trans)-bis-mu-(hexane-1,6-diamine)-mu-[diamine-platinum (II)]-bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032). An example of a hypoxia activatable compound for cancer is tirapazmine.

Examples of microtubule inhibitors/microtubule-stabilizing agents include paclitaxel, vindesine sulfate, 3',4'didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butyla-mide, TDX258, the epothilones (see for example U.S. Pat. Nos. 6,284,781 and 6,288,237, and BMS188797

Some examples of topoisomerase inhibitors are topotecan, hycaptamine, iminotecan, rubitecan, b-ethoxypropionyl-3',4'-O-exo-benzylidene-chartreusin,9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12G-benzo[de]pyrano[',4':b,7]-indolizino[1,2b]quinoline-10,13(9H,15H)dione, lurtotecan, 7-[2-(N-isopropylaminoamino)ethyl]-(20S)camptothecin, BNP1350,BNPI1100,BN80915, BN80942, etoposidephosphate, teniposide, sobuzoxane, 2-dimethylamino-2'-deoxyetoposide, GL331, N-[2-(dimethylamino)ethyl]-9-hydroxy-5,6-dimethyl-6H-pyrido[4,3-b]carbazo-le-1-carboxamide, asulacrine, (5a,5aB,8aa,9b)-9-[2-[N-[2-dimethylamino) ethyl]-N-methylamino)ethyl]-5-[-4-hydroxy-3,5-dimethoxyphenyl]-5,5a,6,8,8a,9-hexohydrofuro(3',4':6,7)naphtho(2,3-d)-1,3-dioxol-6-one,2,3-(methylenedioxy)-5-methyl-7-hydroxy-8-methoxybenzo[c]-phenanthridiniu-m, 6,9-bis[(2-aminoethyl)amino]benzo[g]isoguinoline-5,10-dione,5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethy-1]formamide,N-(2-(dimethylamino)ethyl)acridine-4-carboxamide,6-([2-(dimethylamino)ethyl]amino]-3-hydroxy-7H-indeno[2,1-c] quinolin-7-on-e, and dimesna.

Examples of inhibitors of mitotic kinesins, and in particular the human mitotic kinesin KSP, are described in PCT Publications WO 01/30768 and WO 01/98278, and pending U.S. Ser. Nos. 60/338,779 (filed Dec. 6, 2001), 60/338,344 (filed Dec. 6,2001), 60/338,383 (filed Dec. 6, 2001), 60/338,380 (filed Dec. 6, 2001), 60/338,379 (filed Dec. 6, 2001) and 60/344,453 (filed Nov. 7, 2001).

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea,N6-[4-deoxy-4-[N2-[2(E),4(E)-tetradecadienoyl]glycylamino]-L- glycero-B-L-manno-heptopyranosyl]adenine, aplidine, ecteinascidin, troxacitabine,4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine,11-acetyl-8-(carbamoyloxymethyl)-4-formyl-6-methoxy-14-oxa-1,11-diazatetr-acyclo(7,4,1,0,0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furansylcytosine,3-aminopyridine-2-carboxaldehydethiosemicarbazone and trastuzamab.

Examples of monoclonal antibody targeted therapeutic agents include those therapeutic agents which have cytotoxic agents or radioisotopes attached to a cancer cell specific or target cell specific monoclonal antibody. One particular example is Bexxar.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the an. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAY-CHOL®; see U.S. Pat. No. 5,177,080). The structural formulas of these and additional HMG-CoA reductase inhibitors that may be used m the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-COA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoale, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTasc-II, also, called Rab GGPTase). Examples of prenyl-protein transferase inhibiting compounds include (.+-.)-6-[amino(4-chlorophenyl)(1-methyl-1H-imidazol-5-yl)methyl]-4-(3-ch-lorophenyl)-1-methyl-2 (1H)quinolinone, (–)-6-[amino(4-chlorophenyl)(1-methyl-1H-imidazol-5-yl)methyl]-4-(3-chlor-ophenyl)-1-methyl-2(1H)-quinolinone, (+)-6-[amino(4-chlorophenyl)(1-methyl-1H-imidazol-5-yl)methyl]-4-(3-chlor-ophcnyl)-1-methyl-2 (1H)-quinolinone, 5(S)-n-butyl-1-(2,3-dimethylphenyl)-4-[1-(4-cyanobenzyl)-5-imidazolylmeth-yl]-2-iperazinone, (S)-1-(3-chlorophenyl)4-[1-(4-cyanobenzyl)-5-imidazolyl-methyl]-5-[2-ethanesulfonyl)methyl]-2-p-iperazinone, 5(S)-n-Butyl-1-(2-methylphenyl)-4-[1-(4-cyanobenzyl)-5-imidazolylmethyl]-2-piperazinone, 1-(3-chlorophenyl)4-[1-(4-cyanobenzyl )-2-methyl-5-midazolylmethyl]-2-piperazinone, 1-(2,2-diphenylethyl)-3-[N-(1-(4-cyanobenzyl)-1H-imidazol-5-ylethyl)carba-moyl] piperidine, 4-{5-[4-hydroxymethyl-4-(4-chloropyridin-2-ylmethyl)-piperidine-1-ylmethy-l]-2-methylimidazol-1-ylmethyl}benzonitrile, 4-{5-[4-hydroxymethyl-4-(3-chlorobenzyl)-piperidine-1-ylmethyl]-2-methyli-midazol-1-ylmethyl}benzonitrile, 4-{3-[4-(2-oxo-2H-pyridin-1-yl)benzyl]-3H-imidazol-4-ylmethyl}benzonitril-e, 4-{3-[4-(5-chloro-2-oxo-2H-[1,2']bipyridin-5'-ylmethyl]-3H-imidazol-4-y-lmethyl}benzonitrile, 4-{3-[4-(2-oxo-2H-[1,2']bipyridin-5'-ylmethyl]-3H-imidazol-4-ylmethyl}ben-zonitrile, 4-[3-(2-oxo-1-phenyl-1,2-dihydropyridin-4-ylmethyl)-3H-imidazol-4-ylmethyl}benzonitrile, 18,19-dihydro-19-oxo-5H, 17H-6,10:12,16-dimetheno-1H-imidazo[4,3-c][1,11,4]-dioxaazacyclononadecine-9-carbonitrile, (.+-.)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H,17H-18,21-ethano-6,10:12,16-dimetheno-22H-imidazo-[3,4-h][1,8,11,14] oxatriazacyclocicosine-9-carbonitrile, and (+)-19,20-dihydro-3-methyl-19-oxo-5H-18,21-ethano-12,14-etheno-6,10-methe-no-22H-benzo[d-]imidazo[4,3-k][1,6,9,12]oxa-triazacyclooctadecine-9-carbanitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95110515, WO 95/10516, WO 95/24612, WO 95134535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opihalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol, Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin 11 antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101: 329-354 (2001)). TAFIa inhibitors have been described in U.S. Ser. Nos. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyelacel) and BMS-387032.

As described above, the combinations with NSAID's are directed to the use of NSAID's which are potent COX-2 inhibiting agents. For purposes of this specification an NSAID is potent if it possesses an IC.sub.50 for the inhibition of COX-2 of 1 .mu.M or less as measured by cell or micrsosomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC.sub.50 for COX-2 over IC.sub.50 for COX-1 evaluated by cell or microsomal assays. Such compounds include, but are not limited to those disclosed in U.S. Pat. No. 5,474,995, issued Dec. 12,1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-ichloro-4-(4-chlorobenzoyl)phenyl]methyl]-1H-1,2,3-triaz-ole-4-carboxamide, CM101, qualamine, combretastatin, RP14610, NX31838, sulfated mannopentaose phosphate, 7,7-(carbonyl-bis[imino-N-methyl-4,2-pyrrolocarbonylimino[N-methyl-4,2-py-rrole]-carbonylimino]-bis-(1,3-naphthalenedisulfonate), and 3-[(2, 4-dimethylpyrrol-5-ylmethylene]-2indolinone(SU5416).

As used above, "integrin blockers" refers to compounds which selectively antagonize, inhibit or counteract binding of a physiological ligand to the .alpha..sub.v.beta..sub.3 integrin, to compounds which selectively antagonize, inhibit or counter-act binding of a physiological ligand to the .alpha.v.beta.5 integrin, to compounds which antagonize, inhibit or counteract binding of a physiological ligand to both the .alpha..sub.v.beta..sub.3 integrin and the .alpha..sub.v.beta..sub.5 integrin, and to compounds which antagonize, inhibit or counteract the activity of the particular integrin(s) expressed on capillary endothelial cells. The term also refers to antagonists of the .alpha..sub.v.beta.. sub.6, .alpha..sub.v.beta..sub.8, .alpha..sub.1.beta..sub.1, alpha..sub.2.beta..sub.1, .alpha..sub.5.beta..sub.1, .alpha..sub.6.beta..sub.1 and .alpha..sub.6.beta..sub.4 integrins. The term also refers to antagonists of any combination of .alpha..sub.v.beta..sub.3, .alpha..sub.v.beta..sub.5, .alpha..sub.v.beta..sub.6, .alpha..sub.v.beta..sub.8, .alpha..sub.1.beta..sub.1.alpha..sub.2.beta..sub.1, .alpha..sub.5.beta..sub.1, .alpha..sub.6.beta..sub.1 and .alpha..sub.6.beta..sub.4 integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]q-uinazoline, N-(3-ethynylphenyl)-6,7-bis(2-methoxyethoxy)-4-quinazolinamine, BIBX1382,2,3,9,10,11,12-hexahydro-10-(hydroxymethyl)-10-hydroxy-9-methyl-9,12-epox-y-1H-dindolo[1,2,3,fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo [2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl-1-phthalazinamine, and EMD121974.

Combinations with compounds other than anti-cancer compounds are also encompassed in the instant methods. For example, combinations of the instantly claimed compounds with PPAR-.gamma. (i.e., PPAR-gamma) agonists and PPAR-.delta. (i.e., PPAR-delta) agonists are useful in the treatment of certain malignancies. PPAR-.gamma. and PPAR-.delta. are the nuclear peroxisome proliferator-activated receptors .gamma. and .delta. The expression of PPAR-.gamma. on endothelial cells and its involvement in angiogenesis has been reported in the literature (see J. Cardiovasc. Pharmacol. 1998; 31:909-913; J. Biol. Chem. 1999; 274:9116-9121; Invest. Ophthalmol Vis. Sci. 2000; 41:2309-2317). More recently, PPAR-.gamma. agonists have been shown to inhibit the angiogenic response to VKGF in vitro; both troglitazone and rosiglitazone maleate inhibit the development of retinal neovascularization in mice. (Arch. Ophthalmol. 2001; 119:709-717). Examples of PPAR-.gamma. agonists and PPAR-.gamma./.alpha. agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNUI82716, DRF552926,2-[(5,7-dipropyl-3-trifluoromethyl-1,2-benzisoxazol-6-yl)oxy]-2-methylpro-pionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategics to treating cancer see Hall et al (Am J Hum Genet 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (J Immunol 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, RI01922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. For the treatment or prevention of emesis that may result upon administration of the instant compounds, conjunctive therapy with an anti-emesis agent selected from a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/23155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702: and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

A neurokinin-1 receptor antagonist for use in conjunction with the compounds of the present invention is 2-(R)-(1-(R)-(3,5-bis(trifluoromethyl)phenyl)ethoxy)-3-(S)-(4-floropheny-l)-4-(3-(5-oxo-1H,4H-1,2,4-triazolo)methyl)morpholine or a pharmaceutically acceptable salt which is described in U.S. Pat. No. 5,719,147.

A compound of the instant invention may also be administered with an agent useful in the treatment of anemia. Such an anemia treatment agent is, for example, a continuous erythropoiesis receptor activator, such as apoetin alfa.

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastin.

A compound of the instant invention may also be administered with an immunologic-enhancing drug such as levamisole, Isoprinosine, and zadaxin.

Thus, the scope of the instant invention encompasses the use of the instantly claimed compounds in combination with a second compound selected from: 1) PI3k inhibitor, 2) Akt inhibitor, 3) TNF inhibitor such as Inflixamab, Humira, Etanercept 4) an estrogen receptor modulator, 5) an androgen receptor modulator, 6) retinoid receptor modulator, 7) a cytotoxic agent, 8) an antiproliferative agent, 9) a prenyl-protein transferase inhibitor, 10) an HMG-CoA reductase inhibitor, 11) an HIV protease inhibitor, 12) a reverse transcriptase inhibitor, 13) an angiogenesis inhibitor, 14) an inhibitor of inherent multidrug resistance, 15) an anti-emetic agent, 16) an agent useful in the treatment of anemia, 17) agent useful in the treatment of neutropenia, and 18) an immunologic-enhancing drug in certain cases.

Also included in the scope of the claims is a method of treating cancer that comprises administering a therapeutically effective amount of one or more inositol compounds of the invention or derivative thereof described above in combination with radiation therapy and/or in combination with a compound selected from: 1) PI3k inhibitor, 2) Akt inhibitor, 3)TNF inhibitor such as Inflixamab, Humira, Etanercept 4) an estrogen receptor modulator, 5) an androgen receptor modulator, 6) retinoid receptor modulator, 7) a cytotoxic agent, 8) an antiproliferative agent, 9) a prenyl-protein transferase inhibitor, 10) an HMG-CoA reductase inhibitor, 11) an HIV protease inhibitor, 12) a reverse transcriptase inhibitor, 13) an angiogenesis inhibitor, 14) an inhibitor of inherent multidrug resistance, 15) an anti-emetic agent, 16) an agent useful in the treatment of anemia, 17) agent useful in the treatment of neutropenia, and 18) an immunologic-enhancing drug.

When a composition according to this invention is administered into a human subject, the daily dosage will normally be determined by the proscribing physician with the dosage generally varying according to the age, weight, and response of the individual patient, as well as the severity of the patients symptom's In one exemplary application, in addition to amounts set forth above, a suitable amount of an inhibitor of Akt/PKB is administered to a mammal undergoing treatment for cancer. Administration occurs in an amount of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0.01 mg to about 1000 mg of inhibitor of Akt/PKB. Preferably, the dosage comprises from about 1 mg to about 1000 mg of inhibitor of Akt/PK B.

In addition to the above, the compounds of the invention can be used in combinations with monoclonal antibodies for autoimmune condition treatments such as Adalimumab and certolizumab. Still further the compounds of the invention can be used in combinations with various active agents currently in use for chronic, active hepatitis, in particular, without limitation, pegylated interferon, Ribavarin (copegus, reberol), rebetron, Inteferons, epivir-HBV, inteferon alpha/alpha 2 plus ribavarin combination.

All patents, publications and pending patent applications identified are hereby incorporated by reference.

The compounds of the invention can be also be used in the treatment of or as a synergistic inhibitor of autoimmune diseases mediated by defective or overactive signaling pathways: More particularly, the compounds of the invention can be used in treating patients with Achlorhydra Autoimmune Active Chronic Hepatitis. Addison's Disease, Alopecia, Areata, Amyotrophic Lateral Sclerosis (ACS, Lou Gehrig's Disease), Ankylosing Spondylitis, Anti-GBM Nephritis or anti-TBM Nephritis, Antiphospholipid Syndrome, Aplastic Anemia, Rheumatoid Arthritis, Asthma, Atopic Allergy, Atopic Dermatitis, Autoimmune Inner Ear Disease (AIED), Autoimmune Lymphoproliferative Syndrome (ALPS), Balo Disease, Behcet's Disease, Berger's Disease, (IgA Nephropathy), Bullous Pemphigoid, cardiomyopathy, Celiac Disease, Chronic Fatigue Immune Dysfunction Syndrome (CFIDS), Churg Strauss Syndrome, Cicatricial Pemphigoid, Cogan's Syndrome, Cold Agglutunin Disease, Colitis, Cranial Arteritis, CREST Syndrome, Crohn's Disease, Cushing's Syndrome, Dego's Disease, Dermatitis, Dermatomyositis, Devic Disease, Type 1 Diabetes, Type 2 Diabetes, Dressler's Syndrome, Discoid Lupus, Eczema, Essential Mixed cryoglobulinemia, Eosinophilic, Fasciitis, Epidermolysis Bullosa Acquisita, Evan's Syndrome, Fibromyalgia, Fibromyositis, Fibrosing Alveolitis, Gastritis, Giant Cell Artertis, Glomerulonephritis, Goodpasture's Disease, Grave's Disease, Guillan-Barre Syndrome, Hashimoto's Thyroiditis, Hemolytic Anemia, Henoch-Schonlein Purpura, Hepatitis, Hughes Syndrome, Idiopathic Adrenal Atrophy, Idiopathic Pulmonary Fibrosis, Idiopathic Thrombocytopenia Purpura, Inflammatory Demylinating Polyneuropathy, Irritable Bowel Syndrome, Kawasaki's Disease, Lichen Planus, Lou Gehrig's Disease, Lupoid Hepatitis, Lupus, Lyme Disease, Meniere's Disease, Mixed Connective Tissue Disease, Multiple Myeloma, Multiple Sclerosis, Myasthenia Gravis, Myositis, Ocular Cicatricial Pemphigoid, Osteoporosis, Pars Planitis, Pemphigus Vulgaris, Polyglandular Autoimmune Syndromes, Polymyalgia Rheumatica (PMR), Polymyositis, Primary Biliary Cirrhois, Primary Sclerosing Cholangitis, Psoriasis, Raynaud's Phenomenon, Reiter's Syndrome, Rheumatic Fever, Rheumatoid Arthritis, Sarcoidosis, Seleritis, Scleroderma, Sjogren's Syndrome, Sticky Blood Syndrome, Still's Disease, Stiff Man Syndrome, Sydenham Chorea, Systemic Lupus Erythrmatosis (SLE), Takayasu's Arteritis, Temporal Arteritis, Ulcerative Colitis, Vasculitis, Vitiligo, Wegener's Granulomatosis, and Wilson'sSyndrome.

The invention claimed is:

1. A method of treating a cancer, comprising
administering an effective amount of a D-chiro-inositol compound to a subject in need thereof, thereby treating the cancer, wherein the cancer comprises ovarian, pancreatic, or breast cancer; and
wherein the D-chiro-inositol compound is selected from the group consisting of:
D-chiro-inositol 1,2,3,4-tetraphosphate,
D-chiro-inositol 1,2,3,5-tetraphosphate,
D-chiro-inositol 1,2,4,5-tetraphosphate,
D-chiro-inositol 1,2,4,6-tetraphosphate,
D-chiro-inositol 1,2,5,6-tetraphosphate,
D-chiro-inositol 1,3,4,5-tetraphosphate,
D-chiro-inositol 1,3,4,6-tetraphosphate,
D-chiro-inositol 1,3,5,6-tetraphosphate,
D-chiro-inositol 1,4,5,6-tetraphosphate,
D-chiro-inositol 2,3,4,5-tetraphosphate,
D-chiro-inositol 2,3,4,6-tetraphosphate,
D-chiro-inositol 2,3,5,6-tetraphosphate,
D-chiro-inositol 2,4,5,6-tetraphosphate,
D-chiro-inositol 3,4,5,6-tetraphosphate,
D-chiro-inositol 1,2,3,4,5-pentaphosphate,
D-chiro-inositol 1,2,3,4,6-pentaphosphate,
D-chiro-inositol 1,2,3,5,6-pentaphosphate,
D-chiro-inositol 1,2,4,5,6-pentaphosphate,
D-chiro-inositol 1,3,4,5,6-pentaphosphate,
D-chiro-inositol 2,3,4,5,6-pentaphosphate,
D-chiro-inositol 1,2,3,4,5,6-hexaphosphate,
D-chiro-inositol 1,2,3,4,5-pentaphosphate-6-pyrophosphate,
D-chiro-inositol 1,2,3,4,6-pentaphosphate-5-pyrophosphate,
D-chiro-inositol 1,2,3,5,6-pentaphosphate-4-pyrophosphate,
D-chiro-inositol 1,2,4,5,6-pentaphosphate-3-pyrophosphate,
D-chiro-inositol 1,3,4,5,6-pentaphosphate-2-pyrophosphate,
D-chiro-inositol 2,3,5,6-pentaphosphate-1-pyrophosphate,
D-chiro-inositol 1,2,3-triphosphate-4,5-dipyrophosphate,
D-chiro-inositol 1,2,3-triphosphate-4,6-dipyrophosphate,
D-chiro-inositol 1,2,3-triphosphate-5,6-dipyrophosphate,
D-chiro-inositol 1,2,4-triphosphate-3,5-dipyrophosphate,
D-chiro-inositol 1,2,4-triphosphate-3,6-dipyrophosphate,
D-chiro-inositol 1,2,4-triphosphate-5,6-dipyrophosphate,
D-chiro-inositol 1,2,5-triphosphate-3,4-dipyrophosphate,
D-chiro-inositol 1,2,5-triphosphate-3,6-dipyrophosphate,
D-chiro-inositol 1,2,5-triphosphate-4,6-dipyrophosphate,
D-chiro-inositol 1,2,6-triphosphate-3,4-dipyrophosphate,
D-chiro-inositol 1,2,6-triphosphate-3,5-dipyrophosphate,
D-chiro-inositol 1,2,6-triphosphate-4,5-dipyrophosphate,
D-chiro-inositol 1,3,4-triphosphate-2,5-dipyrophosphate,
D-chiro-inositol 1,3,4-triphosphate-2,6-dipyrophosphate,
D-chiro-inositol 1,3,4-triphosphate-5,6-dipyrophosphate,
D-chiro-inositol 1,3,5-triphosphate-2,4-dipyrophosphate,
D-chiro-inositol 1,3,5-triphosphate-2,6-dipyrophosphate,
D-chiro-inositol 1,3,5-triphosphate-4,6-dipyrophosphate,
D-chiro-inositol 1,3,6-triphosphate-2,4-dipyrophosphate,
D-chiro-inositol 1,3,6-triphosphate-2,5-dipyrophosphate,
D-chiro-inositol 1,3,6-triphosphate-4,5-dipyrophosphate,
D-chiro-inositol 1,4,5-triphosphate-2,3-dipyrophosphate,
D-chiro-inositol 1,4,5-triphosphate-2,6-dipyrophosphate,
D-chiro-inositol 1,4,5-triphosphate-3,6-dipyrophosphate,
D-chiro-inositol 1,4,6-triphosphate-2,3-dipyrophosphate,
D-chiro-inositol 1,4,6-triphosphate-2,5-dipyrophosphate,
D-chiro-inositol 1,4,6-triphosphate-3,5-dipyrophosphate,
D-chiro-inositol 1,5,6-triphosphate-2,3-dipyrophosphate,
D-chiro-inositol 1,5,6-triphosphate-2,4-dipyrophosphate,
D-chiro-inositol 1,5,6-triphosphate-3,4-dipyrophosphate,
D-chiro-inositol 2,3,4-triphosphate-1,5-dipyrophosphate,
D-chiro-inositol 2,3,4-triphosphate-1,6-dipyrophosphate,
D-chiro-inositol 2,3,4-triphosphate-5,6-dipyrophosphate,
D-chiro-inositol 2,3,5-triphosphate-1,4-dipyrophosphate,
D-chiro-inositol 2,3,5-triphosphate-1,6-dipyrophosphate,
D-chiro-inositol 2,3,5-triphosphate-4,6-dipyrophosphate,
D-chiro-inositol 2,3,6-triphosphate-1,4-dipyrophosphate,
D-chiro-inositol 2,3,6-triphosphate-1,5-dipyrophosphate,
D-chiro-inositol 2,3,6-triphosphate-4,5-dipyrophosphate,
D-chiro-inositol 2,4,5-triphosphate-1,3-dipyrophosphate,
D-chiro-inositol 2,4,5-triphosphate-1,6-dipyrophosphate,
D-chiro-inositol 2,4,5-triphosphate-3,6-dipyrophosphate,
D-chiro-inositol 2,4,6-triphosphate-1,3-dipyrophosphate,
D-chiro-inositol 2,4,6-triphosphate-1,5-dipyrophosphate,
D-chiro-inositol 2,4,6-triphosphate-3,5-dipyrophosphate,
D-chiro-inositol 2,5,6-triphosphate-1,3-dipyrophosphate,
D-chiro-inositol 2,5,6-triphosphate-1,4-dipyrophosphate,
D-chiro-inositol 2,5,6-triphosphate-3,4-dipyrophosphate,
D-chiro-inositol 3,4,5-triphosphate-1,2-dipyrophosphate,
D-chiro-inositol 3,4,5-triphosphate-1,6-dipyrophosphate,
D-chiro-inositol 3,4,5-triphosphate-2,6-dipyrophosphate,
D-chiro-inositol 3,5,6-triphosphate-1,2-dipyrophosphate,
D-chiro-inositol 3,5,6-triphosphate-1,4-dipyrophosphate,
D-chiro-inositol 3,5,6-triphosphate-2,4-dipyrophosphate,
D-chiro-inositol 4,5,6-triphosphate-1,2-dipyrophosphate,
D-chiro-inositol 4,5,6-triphosphate-1,3-dipyrophosphate,
D-chiro-inositol 4,5,6-triphosphate-2,3-dipyrophosphate,
D-chiro-inositol 1-phosphate-2,3,4-tripyrophosphate,
D-chiro-inositol 1-phosphate-2,3,5-tripyrophosphate,
D-chiro-inositol 1-phosphate-2,3,6-tripyrophosphate,
D-chiro-inositol 1-phosphate-2,4,5-tripyrophosphate,
D-chiro-inositol 1-phosphate-2,4,6-tripyrophosphate,
D-chiro-inositol 1-phosphate-2,5,6-tripyrophosphate,
D-chiro-inositol 1-phosphate-3,4,5-tripyrophosphate,
D-chiro-inositol 1-phosphate-3,4,6-tripyrophosphate,
D-chiro-inositol 1-phosphate-3,5,6-tripyrophosphate,
D-chiro-inositol 1-phosphate-4,5,6-tripyrophosphate,
D-chiro-inositol 2-phosphate-1,3,4-tripyrophosphate,
D-chiro-inositol 2-phosphate-1,3,5-tripyrophosphate,
D-chiro-inositol 2-phosphate-1,3,6-tripyrophosphate,
D-chiro-inositol 2-phosphate-1,4,5-tripyrophosphate,
D-chiro-inositol 2-phosphate-1,4,6-tripyrophosphate,
D-chiro-inositol 2-phosphate-1,5,6-tripyrophosphate,
D-chiro-inositol 2-phosphate-3,4,5-tripyrophosphate,
D-chiro-inositol 2-phosphate-3,4,6-tripyrophosphate,
D-chiro-inositol 2-phosphate-3,5,6-tripyrophosphate,
D-chiro-inositol 2-phosphate-4,5,6-tripyrophosphate,
D-chiro-inositol 3-phosphate-1,2,4-tripyrophosphate,
D-chiro-inositol 3-phosphate-1,2,5-tripyrophosphate,
D-chiro-inositol 3-phosphate-1,2,6-tripyrophosphate,
D-chiro-inositol 3-phosphate-1,4,5-tripyrophosphate,
D-chiro-inositol 3-phosphate-1,4,6-tripyrophosphate,
D-chiro-inositol 3-phosphate-1,5,6-tripyrophosphate, and
D-chiro-inositol 3-phosphate-4,5,6-tripyrophosphate,
wherein the D-chiro-inositol compound is linked via a covalent bond to a folic acid molecule.

2. The method of claim 1, wherein the D-chiro-inositol compound is selected from the group consisting of:
D-chiro-inositol 1,2,3,4-tetraphosphate,
D-chiro-inositol 1,2,3,5-tetraphosphate,
D-chiro-inositol 1,2,4,5-tetraphosphate,
D-chiro-inositol 1,2,4,6-tetraphosphate, D-chiro-inositol 1,2,5,6-tetraphosphate,
D-chiro-inositol 1,3,4,5-tetraphosphate,
D-chiro-inositol 1,3,4,6-tetraphosphate,
D-chiro-inositol 1,3,5,6-tetraphosphate,
D-chiro-inositol 1,4,5,6-tetraphosphate,
D-chiro-inositol 2,3,4,5-tetraphosphate,
D-chiro-inositol 2,3,4,6-tetraphosphate,
D-chiro-inositol 2,3,5,6-tetraphosphate,
D-chiro-inositol 2,4,5,6-tetraphosphate, and
D-chiro-inositol 3,4,5,6-tetraphosphate.

3. The method of claim 1, wherein the D-chiro-inositol compound is selected from the group consisting of:
D-chiro-inositol 1,2,3,4,5-pentaphosphate,
D-chiro-inositol 1,2,3,4,6-pentaphosphate,
D-chiro-inositol 1,2,3,5,6-pentaphosphate,
D-chiro-inositol 1,2,4,5,6-pentaphosphate,
D-chiro-inositol 1,3,4,5,6-pentaphosphate, and
D-chiro-inositol 2,3,4,5,6-pentaphosphate.

4. The method of claim 1, wherein the D-chiro-inositol compound is D-chiro-inositol 1,2,3,4,5,6-hexaphosphate.

5. The method of claim 1, wherein the D-chiro-inositol compound is selected from the group consisting of:
D-chiro-inositol 1,2,3,4,5-pentaphosphate-6-pyrophosphate,
D-chiro-inositol 1,2,3,4,6-pentaphosphate-5-pyrophosphate,
D-chiro-inositol 1,2,3,5,6-pentaphosphate-4-pyrophosphate,
D-chiro-inositol 1,2,4,5,6-pentaphosphate-3-pyrophosphate,
D-chiro-inositol 1,3,4,5,6-pentaphosphate-2-pyrophosphate,
D-chiro-inositol 2,3 5,6-pentaphosphate-1-pyrophosphate,
D-chiro-inositol 1,2,3-triphosphate-4,5-dipyrophosphate,
D-chiro-inositol 1,2,3-triphosphate-4,6-dipyrophosphate,
D-chiro-inositol 1,2,3-triphosphate-5,6-dipyrophosphate,
D-chiro-inositol 1,2,4-triphosphate-3,5-dipyrophosphate,
D-chiro-inositol 1,2,4-triphosphate-3,6-dipyrophosphate,
D-chiro-inositol 1,2,4-triphosphate-5,6-dipyrophosphate,
D-chiro-inositol 1,2,5-triphosphate-3,4-dipyrophosphate,
D-chiro-inositol 1,2,5-triphosphate-3,6-dipyrophosphate,
D-chiro-inositol 1,2,5-triphosphate-4,6-dipyrophosphate,
D-chiro-inositol 1,2,6-triphosphate-3,4-dipyrophosphate,
D-chiro-inositol 1,2,6-triphosphate-3,5-dipyrophosphate,
D-chiro-inositol 1,2,6-triphosphate-4,5-dipyrophosphate,
D-chiro-inositol 1,3,4-triphosphate-2,5-dipyrophosphate,
D-chiro-inositol 1,3,4-triphosphate-2,6-dipyrophosphate,
D-chiro-inositol 1,3,4-triphosphate-5,6-dipyrophosphate,
D-chiro-inositol 1,3,5-triphosphate-2,4-dipyrophosphate,
D-chiro-inositol 1,3,5-triphosphate-2,6-dipyrophosphate,
D-chiro-inositol 1,3,5-triphosphate-4,6-dipyrophosphate,
D-chiro-inositol 1,3,6-triphosphate-2,4-dipyrophosphate,
D-chiro-inositol 1,3,6-triphosphate-2,5-dipyrophosphate,
D-chiro-inositol 1,3,6-triphosphate-4,5-dipyrophosphate,
D-chiro-inositol 1,4,5-triphosphate-2,3-dipyrophosphate,
D-chiro-inositol 1,4,5-triphosphate-2,6-dipyrophosphate,
D-chiro-inositol 1,4,5-triphosphate-3,6-dipyrophosphate,
D-chiro-inositol 1,4,6-triphosphate-2,3-dipyrophosphate,
D-chiro-inositol 1,4,6-triphosphate-2,5-dipyrophosphate,
D-chiro-inositol 1,4,6-triphosphate-3,5-dipyrophosphate,
D-chiro-inositol 1,5,6-triphosphate-2,3-dipyrophosphate,
D-chiro-inositol 1,5,6-triphosphate-2,4-dipyrophosphate,
D-chiro-inositol 1,5,6-triphosphate-3,4-dipyrophosphate,
D-chiro-inositol 2,3,4-triphosphate-1,5-dipyrophosphate,
D-chiro-inositol 2,3,4-triphosphate-1,6-dipyrophosphate,
D-chiro-inositol 2,3,4-triphosphate-5,6-dipyrophosphate,
D-chiro-inositol 2,3,5-triphosphate-1,4-dipyrophosphate,
D-chiro-inositol 2,3,5-triphosphate-1,6-dipyrophosphate,
D-chiro-inositol 2,3,5-triphosphate-4,6-dipyrophosphate,
D-chiro-inositol 2,3,6-triphosphate-1,4-dipyrophosphate,
D-chiro-inositol 2,3,6-triphosphate-1,5-dipyrophosphate,
D-chiro-inositol 2,3,6-triphosphate-4,5-dipyrophosphate,
D-chiro-inositol 2,4,5-triphosphate-1,3-dipyrophosphate,
D-chiro-inositol 2,4,5-triphosphate-1,6-dipyrophosphate,
D-chiro-inositol 2,4,5-triphosphate-3,6-dipyrophosphate,
D-chiro-inositol 2,4,6-triphosphate-1,3-dipyrophosphate,
D-chiro-inositol 2,4,6-triphosphate-1,5-dipyrophosphate,
D-chiro-inositol 2,4,6-triphosphate-3,5-dipyrophosphate,
D-chiro-inositol 2,5,6-triphosphate-1,3-dipyrophosphate,
D-chiro-inositol 2,5,6-triphosphate-1,4-dipyrophosphate,
D-chiro-inositol 2,5,6-triphosphate-3,4-dipyrophosphate,
D-chiro-inositol 3,4,5-triphosphate-1,2-dipyrophosphate,
D-chiro-inositol 3,4,5-triphosphate-1,6-dipyrophosphate,
D-chiro-inositol 3,4,5-triphosphate-2,6-dipyrophosphate,
D-chiro-inositol 3,5,6-triphosphate-1,2-dipyrophosphate,
D-chiro-inositol 3,5,6-triphosphate-1,4-dipyrophosphate,
D-chiro-inositol 3,5,6-triphosphate-2,4-dipyrophosphate,
D-chiro-inositol 4,5,6-triphosphate-1,2-dipyrophosphate,
D-chiro-inositol 4,5,6-triphosphate-1,3-dipyrophosphate, and
D-chiro-inositol 4,5,6-triphosphate-2,3-dipyrophosphate.

6. The method of claim 1, wherein the D-chiro-inositol compound is selected from the group consisting of:
D-chiro-inositol 1-phosphate-2,3,4-tripyrophosphate,
D-chiro-inositol 1-phosphate-2,3,5-tripyrophosphate,
D-chiro-inositol 1-phosphate-2,3,6-tripyrophosphate,
D-chiro-inositol 1-phosphate-2,4,5-tripyrophosphate,
D-chiro-inositol 1-phosphate-2,4,6-tripyrophosphate,
D-chiro-inositol 1-phosphate-2,5,6-tripyrophosphate,
D-chiro-inositol 1-phosphate-3,4,5-tripyrophosphate,
D-chiro-inositol 1-phosphate-3,4,6-tripyrophosphate,
D-chiro-inositol 1-phosphate-3,5,6-tripyrophosphate,
D-chiro-inositol 1-phosphate-4,5,6-tripyrophosphate,
D-chiro-inositol 2-phosphate-1,3,4-tripyrophosphate,
D-chiro-inositol 2-phosphate-1,3,5-tripyrophosphate,
D-chiro-inositol 2-phosphate-1,3,6-tripyrophosphate,
D-chiro-inositol 2-phosphate-1,4,5-tripyrophosphate,
D-chiro-inositol 2-phosphate-1,4,6-tripyrophosphate,
D-chiro-inositol 2-phosphate-1,5,6-tripyrophosphate,
D-chiro-inositol 2-phosphate-3,4,5-tripyrophosphate,
D-chiro-inositol 2-phosphate-3,4,6-tripyrophosphate,
D-chiro-inositol 2-phosphate-3,5,6-tripyrophosphate,
D-chiro-inositol 2-phosphate-4,5,6-tripyrophosphate,
D-chiro-inositol 3-phosphate-1,2,4-tripyrophosphate,
D-chiro-inositol 3-phosphate-1,2,5-tripyrophosphate,
D-chiro-inositol 3-phosphate-1,2,6-tripyrophosphate,
D-chiro-inositol 3-phosphate-1,4,5-tripyrophosphate,
D-chiro-inositol 3-phosphate-1,4,6-tripyrophosphate,
D-chiro-inositol 3-phosphate-1,5,6-tripyrophosphate, and
D-chiro-inositol 3-phosphate-4,5,6-tripyrophosphate.

7. The method of claim 1, wherein the cancer is ovarian cancer.

8. The method of claim 1, wherein the cancer is pancreatic cancer.

9. The method of claim 1, wherein the cancer is breast cancer.

* * * * *